United States Patent [19]
Fowler et al.

[11] Patent Number: 5,487,989
[45] Date of Patent: Jan. 30, 1996

[54] ETHANOL PRODUCTION BY RECOMBINANT HOSTS

[75] Inventors: David E. Fowler; Philip G. Horton; Arie Ben-Bassat, all of Gainesville, Fla.

[73] Assignee: Bioenergy International, L.C., Gainesville, Fla.

[21] Appl. No.: 946,290

[22] Filed: Sep. 17, 1992

Related U.S. Application Data

[63] Continuation-in-part of Ser. No. 846,344, Mar. 6, 1992, which is a continuation-in-part of Ser. No. 670,821, Mar. 18, 1991, abandoned, and a continuation-in-part of Ser. No. 624,277, Dec. 7, 1990, abandoned, each 352,062, May 15, 1989, Pat. No. 5,000,000 is a continuation-in-part of Ser. No. 239,099, Aug. 31, 1988, abandoned.

[51] Int. Cl.⁶ .............................. C12N 1/21; C12N 9/42; C12P 7/10; C12P 7/14
[52] U.S. Cl. .................. 435/165; 435/209; 435/252.3; 435/852; 435/162
[58] Field of Search ................................ 435/165, 852, 435/252.3

[56] References Cited

U.S. PATENT DOCUMENTS 4,321,328  3/1982  Hoge ........................................ 435/165

OTHER PUBLICATIONS

Al–Zaag, J. Biotechnol. 12:79–86 (1989).
Mes–Hartree et al., Can. Bioenergy R. & D. Seminar (Proc.), 5th, 1984, pp. 469–472, Elsevier Appl. Sci, London.
Ohta et al., Appl. Env. Microbiol. 57:2810–2815 (1991).
Grepinet et al., J. Bacteriol. 170:4576–4581 (1988).
Wong et al., Bio/Technology 6:713–719 (1988).
Biely, Trends Biotechnol. 3:286–290 (1985).
Wood et al., Appl. Env. Microbiol. 58:12103–2110 (1992).

*Primary Examiner*—Robert A. Wax
*Assistant Examiner*—Eric Grimes
*Attorney, Agent, or Firm*—Foley & Lardner

[57] ABSTRACT

Novel plasmids comprising genes which code for the alcohol dehydrogenase and pyruvate decarboxylase are described. Also described are recombinant hosts which have been transformed with genes coding for alcohol dehydrogenase and pyruvate. By virtue of their transformation with these genes, the recombinant hosts are capable of producing significant amounts of ethanol as a fermentation product. Also disclosed are methods for increasing the growth of recombinant hosts and methods for reducing the accumulation of undesirable metabolic products in the growth medium of these hosts. Also disclosed are recombinant host capable of producing significant amounts of ethanol as a fermentation product of oligosaccharides and plasmids comprising genes encoding polysaccharases, in addition to the genes described above which code for the alcohol dehydrogenase and pyruvate decarboxylase. Further, methods are described for producing ethanol from oligomeric feedstock using the recombinant hosts described above. Also provided is a method for enhancing the production of functional proteins in a recombinant host comprising overexpressing an adhB gene in the host. Further provided are process designs for fermenting oligosaccharide-containing biomass to ethanol.

39 Claims, 20 Drawing Sheets

SYMBOLS: ■, pLOI295; ●, pLOI308-2; ○, pLOI308-5;
▲, pLOI308-10; □, STRAIN TC4 LACKING A PLASMID

SYMBOLS: ▲, AEROBIC GROWTH CONDITIONS;
●, ANAEROBIC GROWTH CONDITIONS ic Experiment
ETHANOL PRODUCTION BY RECOMBINANT HOSTS The present invention was made with government support provided, through the Florida Agricultural Experiment Station, under USDA Alcohol Fuels Program grants Nos. 86CRCR12134, 88-37233-3987 and 90-37233-5372 and under DOE Office of Basic Energy grant FG05- 86ER13574. The federal government has certain rights in the present invention. This is a continuation-in-part of application Ser. No. 07/846,344, filed Mar. 6, 1992 (now pending), which is a continuation-in-part of Ser. No. 07/670,821, filed Mar. 18, 1991 (now abandoned), and Ser. No. 07/624,277, filed Dec. 7, 1990 (now abandoned), both of which are continuations-in-part of application Ser. No. 07/352,062, filed May 15, 1989 (now U.S. Pat. No. 5,000,000), itself a continuation-in-part of application Ser. No. 07/239,099, filed Aug. 31, 1988 (now abandoned). The respective contents of these patent documents is hereby incorporated by reference.

BACKGROUND OF THE INVENTION

During glycolysis, cells convert simple sugars like glucose into pyruvic acid, with a net production of ATP and NADH. In the absence of a functioning electron transport system for oxidative phosphorylation, at least 95% of the pyruvic acid is consumed in short pathways which regenerate $NAD^+$, an obligate requirement for continued glycolysis and ATP production. The waste products of these $NAD^+$ regeneration systems are commonly referred to as fermentation products.

Microorganisms are particularly diverse in the array of fermentation products which are produced by different genera. These products include organic acids, such as lactate, acetate, succinate and butyrate, as well as neutral products such as ethanol, butanol, acetone and butanediol. Indeed, the diversity of fermentation products from bacteria has led to their use as a primary determinant in taxonomy. See, for example, BERGEY'S MANUAL OF SYSTEMATIC BACTERIOLOGY, Williams & Wilkins Co., Baltimore (1984) (hereafter "Bergey's Manual").

End products of fermentation share several fundamental features. They are relatively nontoxic under the conditions in which they are initially produced but become more toxic upon accumulation. They are more reduced than pyruvate because their immediate precursors have served as terminal electron acceptors during glycolysis. The microbial production of these fermentation products forms the basis for our oldest and most economically successful applications of biotechnology and includes dairy products, meats, beverages and fuels. In recent years, many advances have been made in the field of biotechnology as a result of new technologies which enable researchers to selectively alter the genetic makeup of some microorganisms.

The bacterium *Escherichia coli* is an important vehicle for the cloning and modification of genes for biotechnology, and is one of the most important hosts for the production of recombinant products. In recent years, the range of hosts used for recombinant DNA research has been extended to include a variety of bacteria, yeasts, fungi, and eukaryotic cells. The invention described here relates to the use of recombinant DNA technology to elicit the production of specific useful products by a modified host.

The DNA used to modify the host of the present invention can be isolated from *Zymomonas mobilis*, a bacterium which commonly is found in plant saps and in honey. *Z. mobilis* has long served as an inoculum for palm wines and for the fermentation of Agave sap to produce *pulque*, an alcohol-containing Mexican beverage. The microbe also is used in the production of fuel ethanol, and reportedly is capable of ethanol-production rates which are substantially higher than that of yeasts.

Although *Z. mobilis* is nutritionally simple and capable of synthesizing amino acids, nucleotides and vitamins, the range of sugars metabolized by this organism is very limited and normally consists of glucose, fructose and sucrose. Substrate level phosphorylation from the fermentation of these sugars is the sole source of energy for biosynthesis and homeostasis. *Zymomonas mobilis* is incapable of growth even in rich medium such as nutrient broth without a fermentable sugar.

*Z. mobilis* is an obligatively fermentative bacterium which lacks a functional system for oxidative phosphorylation. Like the yeast *Saccharomyces cerevisiae*, *Z. mobilis* produces ethanol and carbon dioxide as principal fermentation products. *Z. mobilis* produces ethanol by a short pathway which requires only two enzymatic activities: pyruvate decarboxylase and alcohol dehydrogenase. Pyruvate decarboxylase is the key enzyme in this pathway which diverts the flow of pyruvate to ethanol. Pyruvate decarboxylase catalyzes the nonoxidative decarboxylation of pyruvate to produce acetaldehyde and carbon dioxide. Two alcohol dehydrogenase isozymes are present in this organism and catalyze the reduction of acetaldehyde to ethanol during fermentation, accompanied by the oxidation of NADH to $NAD^+$. Although bacterial alcohol dehydrogenases are common in many organisms, few bacteria have pyruvate decarboxylase. Attempts to modify *Z. mobilis* to enhance its commercial utility as an ethanol producer have met with very limited success.

Most fuel ethanol is currently produced from hexose sugars in corn starch or cane syrup utilizing *S. cerevisiae* or *Z. mobilis*. But such sugars are relatively expensive sources of biomass sugars and have competing value as foods. Starch and sugars represent only a fraction of the total carbohydrates in plants. The dominant forms of plant carbohydrate in stems, leaves, hulls, husks, cobs and the like are the structural wall polymers, cellulose and hemicellulose. Hydrolysis of these polymers releases a mixture of neutral sugars which include glucose, xylose, mannose, galactose, and arabinose. No single organism has been found in nature which can rapidly and efficiently metabolize all of these sugars into ethanol or any other single product of value.

The genes coding for alcohol dehydrogenase II and pyruvate decarboxylase in *Z. mobilis* have been separately cloned, characterized, and expressed in *E. coli*. See Bräu & Sahm [1986a] Arch. Microbiol. 144: 296–301, [1986b] Arch. Microbiol. 146: 105–10; Conway et al. [1987a] J. Bacteriol. 169: 949–54; Conway et al. [1987b] J. Bacteriol. 169: 2591–97; Neale et al. [1987] Nucleic Acid. Res. 15: 1753–61; Ingram & Conway [1988] Appl. Environ. Microbiol. 54: 397–404; Ingram et al. [1987] Appl. Environ. Microbiol. 53: 2420–25.

Bräu and Sahm [1986a], supra, first demonstrated that ethanol production could be increased in recombinant *E. coli* by the over-expression of *Z. mobilis* pyruvate decarboxylase although very low ethanol concentrations were produced. Subsequent studies extended this work by using two other enteric bacteria, *Erwinia chrysanthemi* and *Klebsiella planticola*, and thereby achieved higher levels of ethanol from hexoses, pentoses, and sugar mixtures. See Tolan & Finn [1987] Appl. Environ. Microbiol. 53: 2033–38, 2039–44.

When a feedstock of simple sugars is available, therefore, the aforementioned microbes generally are useful. Nevertheless, the majority of the world's cheap, renewable source of biomass is not found as monosaccharides but rather in the form of lignocellulose, which is primarily a mixture of cellulose, hemicellulose, and lignin. Cellulose is a homopolymer of glucose, while hemicellulose is a more complex heteropolymer comprised not only of xylose, which is its primary constituent, but also of significant amounts of arabinose, mannose, glucose and galactose. It has been estimated that microbial conversion of the sugar residues present in waste paper and yard trash from U.S. landfills could provide over ten billion gallons of ethanol. While microorganisms such as those discussed above can ferment efficiently the monomeric sugars which make up the cellulosic and hemicellulosic polymers present in lignocellulose, the development of improved methods for the saccharification of lignocellulose remains a major research goal.

Current methods of saccharifying lignocellulose include acidic and enzymatic hydrolyses. Acid hydrolysis usually requires heat and presents several drawbacks, however, including the use of energy, the production of acidic waste, and the formation of toxic compounds which can hinder subsequent microbial fermentations. Enzymatic hydrolysis thus presents a desirable alternative. For example, enzymes can be added directly to the medium containing the lignocellulosic material.

Genetic-engineering approaches for the addition of saccharifying traits to microorganisms for the production of ethanol or lactic acid have been directed at the secretion of high enzyme levels into the medium. That is, the art has concerned itself with modifying microorganisms already possessing the requisite proteins for transporting cellularly-produced enzymes into the fermentation medium, where those enzymes can then act on the polysaccharide substrate to yield mono- and oligosaccharides. This approach has been taken because the art has perceived difficulty in successfully modifying organisms lacking the requisite ability to transport such proteins.

SUMMARY OF THE INVENTION

It is therefore an object of the present invention to provide microorganisms that are capable of effectively diverting pyruvate to ethanol during growth under both aerobic and anaerobic conditions.

It is also an object of the present invention to increase the growth of recombinant hosts and to reduce accumulation of undesirable metabolic products in the growth medium of these hosts.

It is yet another object of the present invention to provide recombinant hosts that produce sufficient intracellular levels of polysaccharase enzyme(s) to effect the breakdown of glucose or xylose oligomers to products which the same hosts can ferment to ethanol.

In achieving these and other objects, there is provided, in accordance with the first major domain of the present invention, a recombinant host, other than *Escherichia coli*, comprising heterologous DNA coding for production of alcohol dehydrogenase and pyruvate decarboxylase in the host. The host expresses the DNA at a sufficient functional level so as to facilitate the production of ethanol as a primary fermentation product of the host.

One advantageous embodiment employs the Z. mobilis genes coding for alcohol dehydrogenase and pyruvate decarboxylase in the recombinant hosts. Other aspects of the first domain include plasmids comprising genes coding for alcohol dehydrogenase and pyruvate decarboxylase, which plasmids are useful for providing the inventive recombinant hosts.

In the second major domain of this invention, the recombinant host, in addition to comprising the DNA coding for alcohol dehydrogenase and pyruvate decarboxylase, further comprises DNA coding for proteins which enable the host to transport and metabolize an oligosaccharide. The host expresses the DNA at a level such that the host produces ethanol as a primary fermentation product from the metabolism of the oligosaccharide. Preferred hosts of this domain include enteric bacteria such as Erwinia and Klebsiella. Other preferred hosts will metabolize a di- and/or trisaccharide comprising $C_5$ and/or $C_6$ sugar monomers such as glucose, xylose and maltose.

In the third major domain of this invention, a recombinant host as described above further comprises the DNA necessary to produce one or more polysaccharases. The production of a polysaccharase by the host, and the subsequent release of that polysaccharase into the medium, will reduce the amount of commercial enzyme necessary to degrade the feedstock into fermentable monosaccharides and oligosaccharides.

The polysaccharase DNA can be native to the host, although more often the DNA will be foreign, i.e., heterologous. Advantageous polysaccharases include cellulolytic, xylanolytic and starch-degrading enzymes. The polysaccharase can be at least partially secreted by the host, or it can be accumulated substantially intracellularly for subsequent release. Advantageously, intracellularly-accumulated enzymes which are thermostable, can be released when desired by heat-induced lysis. Combinations of enzymes can be encoded by the heterologous DNA, some of which are secreted, and some of which are accumulated.

Other modifications can be made to enhance the ethanol production of the foregoing hosts. For example, the host can further comprise an additional heterologous DNA segment, the expression product of which is a protein involved in the transport of mono- and/or oligosaccharides into the recombinant host. Likewise, additional genes from the glycolytic pathway can be incorporated into the host. In such ways, an enhanced rate of ethanol production can be achieved.

Also, methods for producing ethanol using all of the foregoing hosts are provided. Further, methods are provided for treating an oligosaccharide feedstock to convert the oligosaccharide into ethanol, and into simpler oligosaccharides and/or saccharide monomers. Yet another aspect provides a method for reducing the accumulation of acidic metabolic products in a growth medium by employing the inventive transformed hosts to produce ethanol in the medium. Still another aspect provides a method for enhancing the production of functional proteins in a recombinant host comprising overexpressing an adhB gene, such as that found in Z. mobilis, in the host. Another aspect of this invention includes process designs for fermenting oligosaccharide-containing biomass to ethanol.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

(FIG. 8A) or 60° C. (FIG. 8B) in Luria broth (pH 6.0) containing 4% birchwood xylan.

FIG. 10A illustrates the growth and FIG. 10B illustrates the ethanol production.

FIG. 11A illustrates the ethanol production from glucose (100 g/liter) by strain M5A1(pLOI555), strain P2 containing integrated pet genes, and strain B1 containing integrated pet genes. FIG. 11B illustrates the ethanol production from cellobiose (100 g/liter) fermentation by strain P2.

DETAILED DESCRIPTION OF THE INVENTION

I. Conventional Carbohydrate Metabolism

Figure 1:
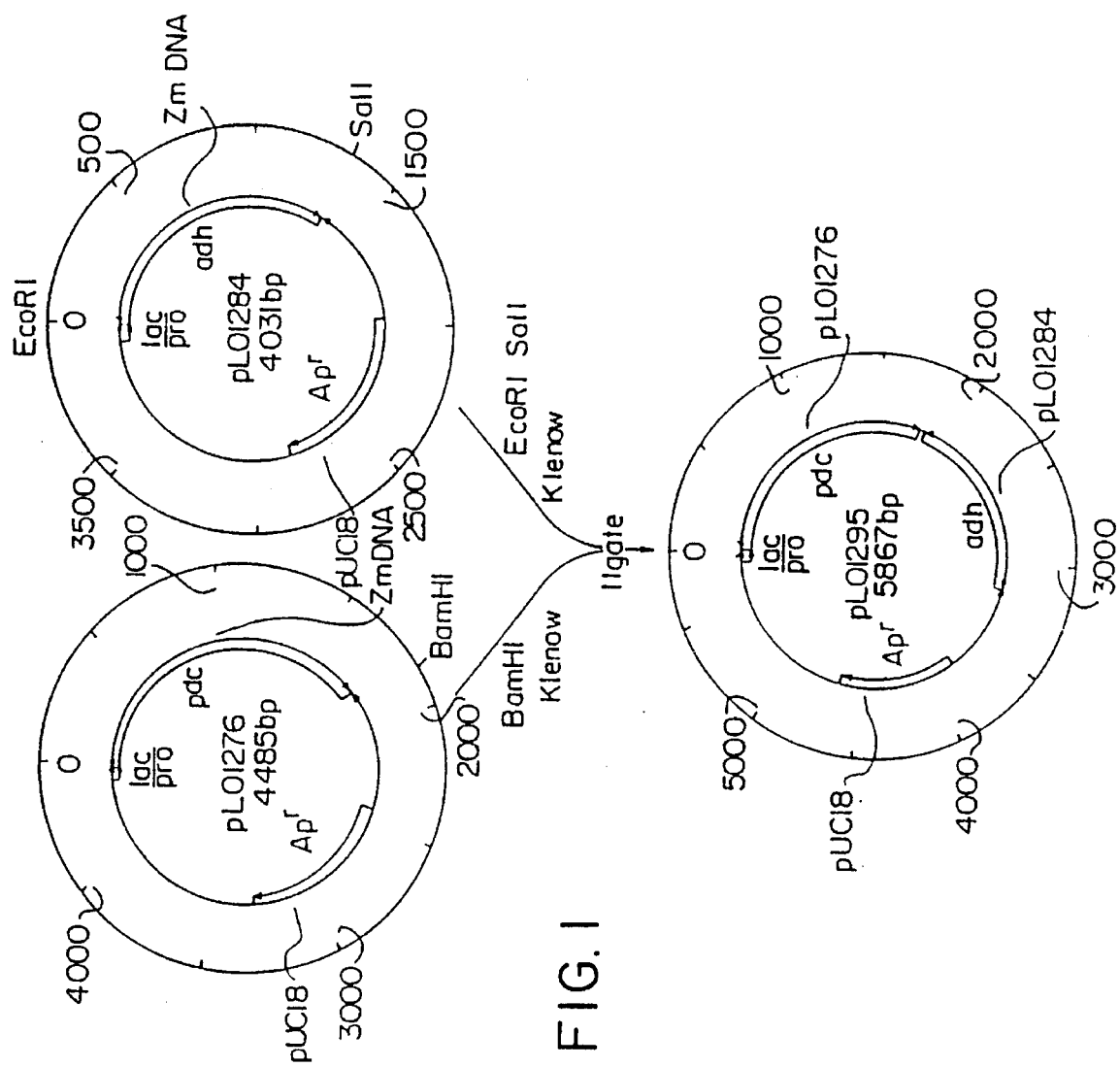
FIG. 1 illustrates the construction of pLOI295 containing genes encoding pyruvate decarboxylase and alcohol dehydrogenase II from *Z. mobilis*. Abbreviations: RI, EcoRI; H, HindIII; B, BamHI; t, terminator; adh, *Z. mobilis* alcohol dehydrogenase II; pdc, *Z. mobilis* pyruvate decarboxylase; cat, chloramphenicol acyltransferase; Ap, β-lactamase; Zm Pro frags, fragments of *Z. mobilis* DNA which exhibit promoter activity; ColE1, replication origin derived from pBR322; oriV, replication origin derived from RSF1010; $P_{lac}$, lac promoter; $P_{Zm}$, promoter from *Z. mobilis*; $P_?$, cryptic promoter on vector; Kb, kilobases.
Figure 2:
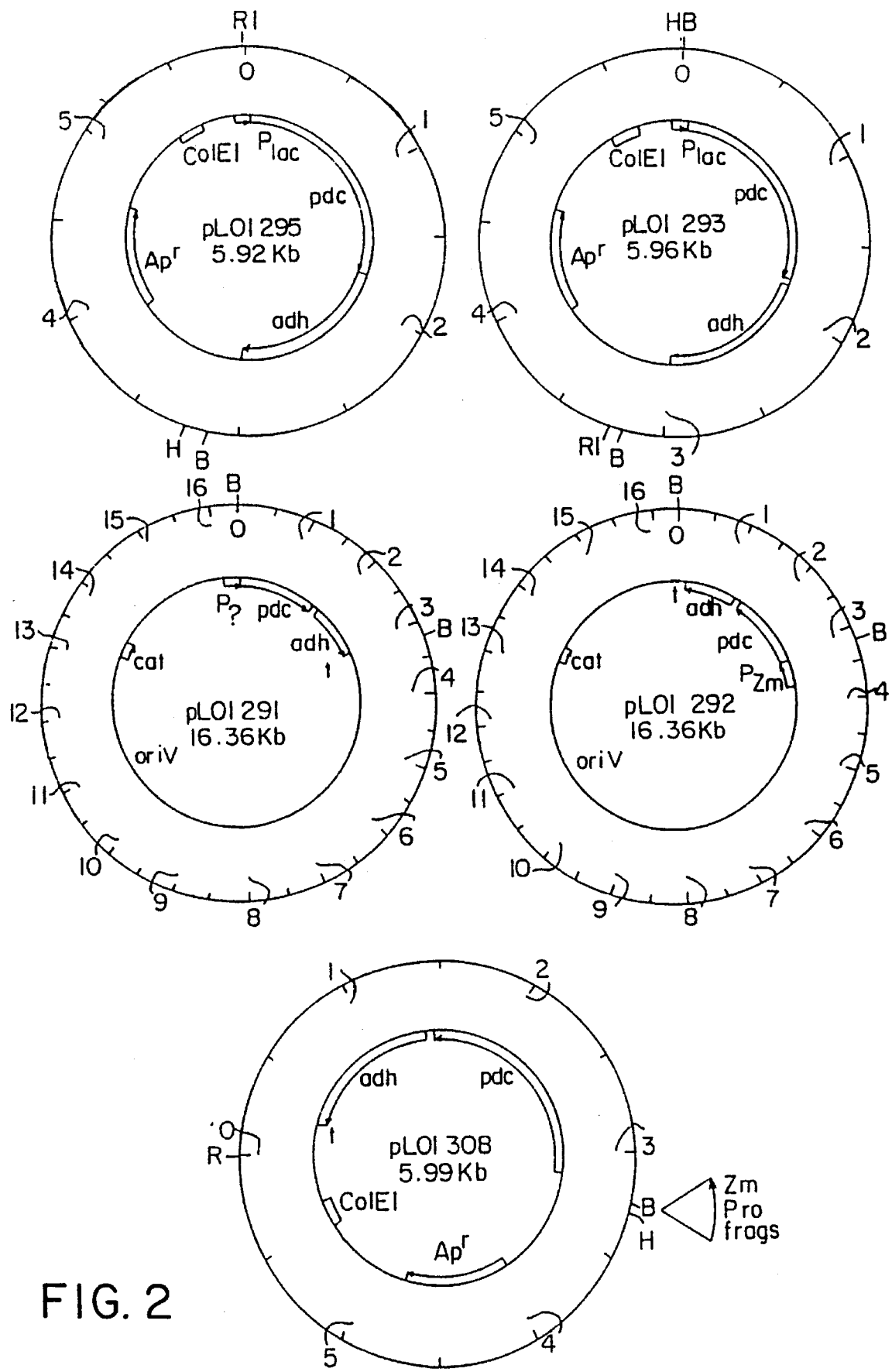
FIG. 2 illustrates several plasmids containing the genes encoding pyruvate decarboxylase and alcohol dehydrogenase II from *Z. mobilis*.

In most animals and plants as well as bacteria, yeasts and fungi, glucose is degraded initially by an anaerobic pathway prior to either oxidative or fermentative metabolism. The most common such pathway, termed glycolysis, refers to the series of enzymatic steps whereby the six-carbon glucose molecule is broken down, via multiple intermediates, into two molecules of the three carbon compound, pyruvate. During this process, two molecules of $NAD^+$ are reduced to form NADH. The net reaction in this transformation of glucose into pyruvate is:

glucose+2 $P_i$+2 ADP+2 $NAD^+ \rightarrow$ 2 pyruvate+ 2 ATP+2 NADH+2 $H^+$ For glycolysis to continue, the $NAD^+$ consumed by glycolysis must be regenerated by the oxidation of NADH. During oxidative metabolism, NADH typically is oxidized by donating hydrogen equivalents via a series of steps to oxygen and thereby forms water. Most organisms contain additional anaerobic pathways, however, which allow glycolysis to continue in the absence of compounds like oxygen. Such anaerobic processes are termed fermentation, and homolactic acid fermentation is perhaps one of the most common of these pathways occurring in many bacteria and in animals. In homolactic fermentation, glucose ultimately is converted to two molecules of the three carbon acid, lactic acid. NADH is oxidized by donating hydrogen equivalents to pyruvate and thus produces lactic acid. The net reaction for the regeneration of $NAD^+$ by lactic acid fermentation is:

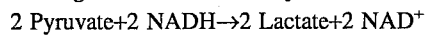
2 Pyruvate+2 NADH$\rightarrow$2 Lactate+2 $NAD^+$

As mentioned previously, ethanologenic organisms like *Z. mobilis* and *S. cerevisiae* are capable of a second (alcoholic) type of fermentation whereby glucose is metabolized to two molecules of ethanol and two molecules of $CO_2$. Alcoholic fermentation differs from lactic acid fermentation in the steps used for the regeneration of $NAD^+$. Two different enzymatic steps are required for alcoholic fermentation. Pyruvate decarboxylase cleaves pyruvate into acetaldehyde and carbon dioxide. Alcohol dehydrogenase serves to regenerate $NAD^+$ by transferring hydrogen equivalents from NADH to acetaldehyde, thereby producing ethanol. The reactions for the regeneration of $NAD^+$ by alcoholic fermentation are:

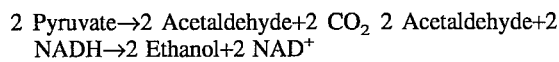
2 Pyruvate$\rightarrow$2 Acetaldehyde+2 $CO_2$  2 Acetaldehyde+2 NADH$\rightarrow$2 Ethanol+2 $NAD^+$ The net reaction for alcoholic fermentation is:

2 Pyruvate+2 NADH$\rightarrow$2 Ethanol+2 $CO_2$+2 $NAD^+$

DNA that encodes each of these enzymes, respectively, had been cloned, and *Z. mobilis* pyruvate decarboxylase had been expressed recombinantly. See, for example, Bräu &

Sahm [1986a], supra. But it was highly uncertain whether the glycolytic pathway in organisms that do not produce ethanol as a primary metabolite ("non-ethanologenic organisms") could be diverted extensively at the pyruvate stage, even if such organisms could be modified somehow to express both of the additional enzymes required for alcoholic fermentation.

To the contrary, there was an expectation in the art that such a diversion might starve the recombinant host for pyruvate and its normal products. See Bräu & Sahm [1986a, b], supra. There also was a possibility that diversion of carbon from glycolysis to ethanol production in otherwise non-ethanologenic organisms would upset NAD/NADH ratios crucial to interrelated energy-generation and biosynthetic pathways.

II. Fermentation Pursuant to the Present Invention

It has been discovered, however, that organisms which carry out glycolysis or some variant thereof can be engineered, in accordance with the present invention, to divert as much as 95% of the carbon flow from glycolysis, at the pyruvate stage, to what in essence is a synthetic pathway comprised of the enzymes encoded by heterologous pyruvate decarboxylase (pdc) and alcohol dehydrogenase (adh) genes. The result is an engineered organism which produces ethanol as its primary fermentation product. That is, the ethanol produced exceeds 50% of the total fermentation product.

It also has been discovered that hosts can be selected for such heterologous expression which, by virtue of their native ability to transport and metabolize oligosaccharides, can ferment more complex feedstocks. (In this context, "oligosaccharide" denotes a molecule comprised of two or more saccharide monomers, including but not limited to the disaccharides cellobiose, maltobiose and xylobiose, trisaccharides like cellotriose and xylotriose, and long-chain polysacharrides such as cellulose, hemicellulose, starch, glycogen, pectin and inulin.) The capabilities of a host thus selected and transformed can be augmented, moreover, by expression in the same host of one or more genes coding for a polysaccharase, i.e., an enzyme that catalyzes the breakdown to smaller oligosaccharides and/or saccharide monomers of complex oligosaccharides.

(A) GENETICALLY ENGINEERING AN ARTIFICIAL ETHANOLOGENIC PATHWAY: An important aspect of the present invention is an operon that directs cells to produce ethanol. Exemplary of such an operon is a construct of the present invention, designated a "pet operon," which comprises *Z. mobilis* genes coding for alcohol dehydrogenase II and pyruvate decarboxylase activities, respectively, together with appropriate regulatory sequences, for example, promoters, inducers, operators, ribosomal binding sites and transcriptional terminators. Thus, the dependence upon native alcohol dehydrogenase activity for ethanol production in previous recombinant systems is eliminated by combining *Z. mobilis* genes encoding alcohol dehydrogenase II and pyruvate decarboxylase to form a pet operon. Moreover, significant amounts of ethanol can be produced, in recombinants containing the pet operon, under both aerobic and anaerobic conditions.

To impart to a microorganism the ability to produce polysaccharases, such as xylanases and cellulases, a ethanologenic operon of the present invention can be modified by adding the gene(s) which code for the desired enzyme(s). Alternatively, one or more polysaccharase-encoding genes can be incorporated into a plasmid which is used to transform a host organism already engineered with an operon that directs ethanol production, as described above. (This aspect of the present invention is described in more detail in Section II(E) below.) By yet another alternative approach, the host to be transformed with the ethanologenic operon is selected for its native ability to express a polysaccharase. Yet another approach is to add the polysaccharase genes into the chromosome by integration.

The approach of combining, in a single construct, the genes that encode a metabolic pathway is generalized readily to a variety of situations where genes from different loci can be brought together to create an artificial operon. The creation of a pet operon thus is but one example of the applications envisaged for the present invention. For example, genes coding for alcohol dehydrogenase activity from a variety of organisms could be combined with other genes coding for pyruvate decarboxylase activity in order to create an operon coding for the desired pathway. Operons coding for other pathways also could be created. It also is apparent that, for the above-discussed ethanologenic pathway, it is not necessary that the genes coding for alcohol dehydrogenase and pyruvate decarboxylase activities be under common control; they could be under separate control, even in different plasmids or in different locations on the chromosome. Likewise, gene(s) encoding polysaccharases could be under common or separate control, or located in different plasmids or at different chromosomal positions.

Another aspect of the present invention concerns the use of recombinant ethanol-producing hosts for the efficient production of recombinant peptides or proteins; that is, the recombinant cells can be transformed further with genes coding for useful products other than polysaccharases. (These additional genes could be plasmid-borne or incorporated into the chromosome.) More specifically, genes that encode the necessary ethanologenic enzymes generally are expressed at high levels and dominate carbon flow from pyruvate and NADH oxidation during anaerobic growth. Under these conditions, the flow of pyruvate carbon skeletons can be diverted from the production of organic acids to the production of ethanol as the principal fermentation product.

In this way, the extent of acidification per unit of cell protein is minimized by the production of ethanol rather than of organic acids. Oxygen transfer is frequently a major limitation during the growth of dense cultures of microorganisms, and it is this limitation which results in acid production and pH drift of the growth medium. In recombinants expressing an ethanologenic operon within the present invention, by contrast, the heterologous, ethanologenic enzymes divert part of the pyruvate from glycolysis to acetaldehyde and reoxidize NADH to produce ethanol, a less damaging product of metabolism. Thus, strains containing both functional respiratory chains for oxidative phosphorylation and ethanol production enzymes can be grown to even higher cell densities because of the operation of both systems during the regeneration of $NAD^+$ and a reduction in acidic waste products. Such inherent flexibility results in less stringent process-control requirements, as well as increased volumetric yields of recombinant products.

The accumulation of organic acids which otherwise occurs is regarded as a consequence of fermentation during anaerobic growth. But appreciable quantities of acetate may be produced even under aerobic conditions, e.g., during rapid agitation. Thus, the production of acetate may be progressive from the earliest stages of growth and not limited to the later stages, when cell density is high and anaerobic conditions prevail. Acid production from glucose, even under aerobic conditions, serves to limit growth in broth and on solid medium, as demonstrated by the increased final cell density in medium supplemented with phosphate buffer.

Accordingly, ethanol-producing transformants within the present invention also are superior hosts for production of recombinant products, even under anaerobic conditions, with minimal acid production. Many recombinant proteins and peptides contain cysteine or disulfide bridges, and proper folding or reactions of these is an essential feature to form the active enzyme. Since formation of disulfide bonds is promoted by oxygen, synthesis of such proteins under anaerobic conditions provides less opportunity for improper folding prior to isolation and folding under controlled conditions, thus resulting in greater recovery of biologically active product.

The use of adhB in these constructs may be of particular advantage. AdhB encodes a stress protein (An et al. [1991] FEBS LETTERS 282:205–208). Stress proteins have been shown to aid in the proper folding of heterologous proteins allowing the retention of biological function. Lee et al. [1992] J. Biol. Chem. 267:2849–2852. Accordingly the use of adhB could enhance the production of functional proteins in recombinant organisms.

Under aerobic conditions in *E. coli*, pyruvate from glycolysis is primarily metabolized by the pyruvate dehydrogenase complex and by lactate dehydrogenase, with excess acetyl coenzyme A being converted to acetate. See Gottschalk, BACTERIAL METABOLISM, pp. 210–80 (Springer-Verlag 1986). The apparent $K_m$ values for these two enzymes are 0.4 and 7.2 mM, respectively. The apparent $K_m$ for *Z. mobilis* pyruvate decarboxylase is equal to (pyruvate dehydrogenase) or lower than (lactate dehydrogenase) those for the two *E. coli* enzymes, thereby facilitating acetaldehyde production. $NAD^+$ regeneration under aerobic conditions results primarily from biosynthesis and from the NADH oxidase (coupled to the electron transport system) with an apparent $K_m$ of 50 μM. The apparent $K_m$ for *Z. mobilis* alcohol dehydrogenase II is over four-fold lower than that for *E. coli* $NAD^+$ oxidase, allowing the *Z. mobilis* enzyme to compete effectively for endogenous pools of NADH for the reduction of acetaldehyde to ethanol. Accordingly, the properties of the *Z. mobilis* ethanologenic enzymes and their relatively high levels of expression are well suited for the diversion of carbon flow into ethanol under aerobic conditions.

Under anaerobic conditions in *E. coli*, pyruvate from glycolysis is primarily metabolized by lactate dehydrogenase and pyruvate formate lyase. The apparent $K_m$ values for these two enzymes are 18-fold and 5-fold higher, respectively, than that for *Z. mobilis* pyruvate decarboxylase. Similarly, the apparent $K_m$'s for the principal enzymes involved in $NAD^+$ regeneration in *E. coli* also are considerably higher than those for *Z. mobilis* alcohol dehydrogenase II. Thus, the ethanologenic enzymes from *Z. mobilis* are quite competitive for carbon (pyruvate) and reducing potential (NADH) with the normal fermentative enzymes and oxidative phosphorylation in *E. coli*, allowing the efficient channeling of glycolytic products into ethanol.

It has been discovered that lactose and all of the major sugars present in cellulose and hemicellulose (namely, glucose, xylose, arabinose, galactose and mannose) can be converted to ethanol, in accordance with the present invention, by recombinant hosts that express genes encoding ethanologenic enzymes, such as those comprising the above-discussed ethanol pathway of *Z. mobilis*.

A variety of factors should be considered in selecting host strains suitable for ethanol production pursuant to the present invention. These factors include substrate range and environmental hardiness, such as sugar tolerance, salt tolerance, ethanol tolerance, tolerance to low pH, and thermal tolerance. As described below, for example, *E. coli* strain ATCC 9637 (Waksman strain W) displays superior characteristics in terms of environmental hardiness, although ethanol production from glucose was lower than with other strains. Strain ATCC 9637 was selected primarily for its unique ability to utilize sucrose. Advantageously, this characteristic of ATCC 9637 makes this strain useful in the fermentation of beet sugar, cane sugar, and other feedstocks with sucrose. ATCC 11303 (Luria strain B) and ATCC 15244 (Kepes strain ML300) containing pLOI297 produced the highest levels of ethanol and exhibited acceptable levels of environmental hardiness. Plasmids were quite stable in these two constructs and they were selected as the best candidates for further development of ethanol production. Both constructs expressed the high levels of *Z. mobilis* pyruvate decarboxylase which are required for efficient ethanol production. See Ingram et al. [1987].

All major sugar components of plant biomass were converted to ethanol by the recombinant *E. coli* containing the ethanol pathway from *Z. mobilis*. The conversion efficiency of glucose and xylose into ethanol exceeded that which has been previously reported for *S. cerevisiae*, see Lovitt et al. [1988] CRC Crit. Rev. Biotechnol. 7: 107–186, and for pentose-fermenting yeasts systems. See Beck [1989] Biotechnol. Bioeng. Symp. 17: 617–627; Jeffries et al. [1988] Biotechnol. Bioeng. 31: 502–506; Skoog et al. [1988] Enzyme Microbiol. Technol. 10:66–79; Slininger et al. [1985] Biotechnol. Lett. 7:431–436). Xylose was converted to ethanol by recombinant *E. coli* with a higher efficiency than glucose by *S. cerevisiae*, as reported by Lovitt et al., supra. The unusually high ethanol yields with xylose (over 100% of theoretical) might be attributed to ethanol derived from the catabolism of complex nutrients. Many amino acids and complex medium components are catabolized to glycolytic intermediates or to pyruvate directly. This pyruvate could then be converted to ethanol.

According to the present invention, pdc and adh genes can be transformed into a variety of different hosts and expressed using a variety of promoters. It is well within the skill of a person trained in this field to use the descriptions provided herein to make these transformations. For example, pdc and adh genes can be readily inserted into plasmids which have different host ranges. Plasmids which are constructed to replicate in *E. coli* and another target organism are typically called "shuttle vectors," since they are able to replicate in two or more hosts. These plasmids are readily available and easily used. Most frequent combinations include shuttles between *E. coli* and other bacteria, *E. coli* and yeasts, and *E. coli* and animal cells. These vectors are available from catalogs and are well known to those skilled in the art.

*Z. mobilis* pdc and adh genes have been inserted and expressed in Xanthomonas, Klebsiella and Erwinia. Similar success in other organisms also can be achieved readily. Although some straightforward modification of the promoter, for example, may be needed to produce the optimal construct, success is highly predictable based upon biochemical properties and current knowledge of expression of soluble cytoplasmic proteins. Foreign genes expressing enzymatic activity needed to redirect pyruvate metabolism, in accordance with the present invention, can even be integrated into the chromosome and expressed without the need for a plasmid. See Section II(C), infra. For example, a pet construct which lacks a promoter can be integrated into the *E. coli* chromosome immediately behind the promoter for the pyruvate formate lyase gene. Analogous integration into pfl or other genes is possible in most organisms, requiring only a fragment of the target gene to direct the site of integration by homologous recombination. Target genes other than pfl also could be used for integration. Since pet-expressing constructs are easily identified on indicator plates, this approach is widely feasible for the rapid and efficient construction of other organisms for ethanol production.

A great many texts are available which describe procedures for expressing foreign genes. Also, catalogs list vectors which can be used for various organisms. Cloning vectors for gram-negative bacteria, gram-positive bacteria, vectors with broad host range capability, fungal cloning vectors, insect cloning vectors, animal cell cloning vectors, and plant cell cloning vectors are all well known to those skilled in the art. Catalogs from which these cloning vectors can be ordered and are readily available and well known to those skilled in the art. See, for example, Marino [1989] BioPharm 2: 18–33; VECTORS: A SURVEY OF MOLECULAR CLONING VECTORS AND THEIR USES (Butterworths 1988).

The skilled practitioner also has access to alternative pdc and adh genes, and to other such genes which can be identified by use of the aforementioned Z. mobilis genes as probes or, more preferably, by observing activity on indicator plates. For purposes of this invention, it does not matter whether the alcohol dehydrogenase activity is provided from a gene isolated from a horse, yeast, human, insect, or other bacterial gene. Since expression of alcohol dehydrogenase activity can be observed directly on aldehyde indicator plates, sequence information would not be needed for the isolation of additional genes encoding proteins which exhibit this enzymatic activity. Indeed, many alcohol dehydrogenase genes are already well known to those skilled in the art, as evidenced by the recitation of 252 adh genes in the Genbank database as of March 1991 (IntelliGenetics Inc., 700 E. El Camino Drive, Mountain View, Calif. 94040).

Z. mobilis contains two genes encoding functional alcohol dehydrogenase genes, and one of these (adhB) is related evolutionarily to a butanol dehydrogenase from *Clostridium acetobutylicum*, propanediol oxidoreductase from *E. coli*, and ADHIV alcohol dehydrogenase from Saccharomyces. All have been cloned and sequenced. The second alcohol dehydrogenase gene from Z. mobilis, adhA, is a zinc alcohol dehydrogenase which also has been cloned and sequenced. Based upon comparisons of primary structure deduced from sequences which are readily available, the adhA gene is deemed related evolutionarily to the typical alcohol dehydrogenases described in animals, plants, and the dominant adh gene in yeasts. The adhA gene and other alcohol dehydrogenase genes can be substituted for the original adhB gene exemplified herein.

By the same token, for purposes of this invention it does not matter whether the pyruvate decarboxylase activity is provided by a gene from Z. mobilis or by a gene which encodes the needed enzymatic activity but which comes from corn, yeast or some other organism. The evolution of life forms from common ancestry is now well accepted and has been demonstrated in splendid detail by the methods of molecular genetics. Not only can organisms be arranged in phylogenetic trees based upon macro-characteristics, but the ancestral genes which have evolved for specific functions have been retained throughout evolution with conservation of features required for such functions. This high level of conservation enables those skilled in the art to isolate functionally equivalent, genetically related enzymes from other organisms using primary information from one or more members of an enzyme family. The enzymes of glycolysis are some of the best examples of this since such enzymes have been so well studied.

Indeed, just such an approach has been used successfully to clone the pyruvate decarboxylase gene from maize, using information on the Z. mobilis pdc and the pdc of *S. cerevisiae* to design a DNA probe. See Kelly [1989] Plant Molecular Biology 13: 213–22. Alternative strategies could have used the entire genes as probes. Since the synthesis of a protein with pyruvate decarboxylase activity (pyruvate converted to acetaldehyde plus carbon dioxide) can be observed directly on aldehyde indicator plates, sequence information would not be needed to locate other genes, although sequence information has been used to isolate the corn gene. Many other pyruvate decarboxylase genes which provide a functional equivalent can be isolated from other organisms. These other genes would be suitable replacements for the Z. mobilis pdc, just as several alcohol dehydrogenases have proven suitable. Further in that regard, the GenBank database listed at least 5 pdc genes as of March 1991.

As a further improvement, a recombinant host within the present invention can be transformed with genes encoding key components of the glucose transport in Z. mobilis, namely, the genes coding for Z. mobilis glucokinase (glk) and for glucose-facilitated diffusion protein (glf). In particular, glk and glf can be combined in an artificial operon, along the lines described above for an ethanologenic operon such as pet, and transformed into a recombinant already containing the latter operon. Expression of the glk/glf operon would result in an increase in trans-membrane glucose flux and, hence, in an increased rate of ethanol production. Likewise, genes encoding key components of the transport of oligosaccharides in other hosts, or genes encoding key components in the glycolytic pathway, also can be used to further transform hosts in accordance with this invention. Such transformation with genes encoding rate-limiting steps in flux can be expected to increase the rate of ethanol production and boost the levels of glycolytic intermediates as a source of skeletons for biosynthesis.

(B) FERMENTATION PARAMETERS: Pursuant to the present invention, heterologous ethanologenic genes are expressed at levels that facilitate the production of ethanol as a fermentation product by the recombinant host. By inserting such genes into an appropriate non-ethanologenic organism, as described above, the transformed host is enabled to produce significant amounts of ethanol from oligosaccharides like cellobiose, cellotriose, xylobiose and xylotriose. As discussed below, ethanol concentrations on the order of 1M, and up to 1.5M can be obtained from recombinant hosts according to the present invention.

(C) CHROMOSOMAL INTEGRATION OF FOREIGN GENES: Chromosomal integration of foreign genes can offer several advantages over plasmid-based constructions, the latter having many limitations for commercial processes. Plasmid-based constructions are inherently less stable than chromosomal genes and serve as an environmental hazard, a reservoir for transmission of heterologous traits. Instability often is exacerbated by the addition of multiple plasmids. Nevertheless, plasmid-based constructions can be useful for initial experiments involving expression of heterologous genes, such as genes encoding cellulases, since they can be used to readily transform host cells. But to facilitate screening of the resulting protein (e.g., a cellulase), it is often desirable to eliminate the need for a plasmid carrying ethanol-producing genes by chromosomal integration in accordance with this invention.

Ethanologenic genes have been integrated chromosomally in *E. coli* B, see Ohta et al. [1991] Appl. Environ. Microbiol. 57: 893–900. In general, this is accomplished by purification of a DNA fragment containing (1) the desired genes upstream from a chloramphenicol gene and (2) a fragment of homologous DNA from the target organism. This DNA can be ligated to form circles without replicons and used for transformation. Thus, the pfl gene can be targeted in the case of *E. coli,* and short, random Sau3A fragments can be ligated in Klebsiella to promote homologous recombination.

Initial selections of recombinants can be made on 20 mg chloramphenicol ("Cm")/liter plates to allow growth after single copy integration. These constructs may be obtained at a very low frequency. Ethanologenic genes initially may be expressed at low levels, insufficient to permit efficient ethanol fermentation. Higher level expression may be achieved as a single step by selection on plates containing 600 to 1000 mg Cm/liter. Such strains have proven very stable and it is anticipated that the same approach will be successful for more optimal strains of Klebsiella and Erwinia. Preliminary testing of a few wild strains indicates that electroporation improves plasmid delivery and may reduce the effort required to achieve integrations. (See Example 16 below.)

(D) HOST SELECTION: The range of organisms suitable for modification to express heterologous pdc and adh genes, as described above, includes, inter alia, eukaryotic cells, such as animal cells, insect cells, fungal cells, and yeasts which are not naturally ethanologenic, and non-ethanologenic bacteria. In addition to *E. coli,* for example, other enteric bacteria of the genera Erwinia, like *E. chrysanthemi,* and Klebsiella, like *K. planticola* and *K. oxytoca,* are particularly attractive hosts because they can metabolize a variety of sugars, including pentoses. Advantageous hosts can also be selected from the broader category of gram-negative bacteria, such as species of the genus Xanthomonas, and from the gram-positive bacteria, such as members of the genera Bacillus, Clostridium and Cellulomonas. Appropriate transformation methodology is available for each of these different types of hosts.

Certain organisms among the aforementioned microbes also meet the criteria for selection of a host to ferment oligosaccharide(s) to ethanol in accordance with the present invention. More specifically, a host can be selected in this regard because it produces (1) the proteins necessary to transport an oligosaccharide into the cell and (2) intracellular (cytoplasmic) levels of enzymes which metabolize those oligosaccharides. Microbes mentioned previously that meet these criteria include enteric bacteria like *E. chrysanthemi* and other Erwinia, and Klebsiella species such as *K. oxytoca,* which naturally produces a β-xylosidase, and *K. planticola.* Certain *E. coli* also satisfy the criteria because they transport and metabolize cellobiose, maltose and/or maltotriose. See, for example, Hall et al. [1987] J. Bacteriol. 169: 2713–17.

Hosts can be selected, in satisfaction of criteria (1) and (2) above, from the broader categories of gram-negative bacteria, such as Xanthomonas species, and gram-positive bacteria, including members of the genera Bacillus, such as *B. pumilus, B. subtilis* and *B. coagulans;* Clostridium, for example, *Cl. acetobutylicum, Cl. aerotolerans, Cl. thermocellum, Cl. thermohydrosulfuricum* and *Cl. thermosaccharolyticum;* Cellulomonas species like *C. uda;* and *butyrivibrio fibrisolvens.* Similarly acceptable are various yeasts, exemplified by species of Cryptococcus like *Cr. albidus,* species of Monilia, *Pichia stipitis* and *Pullularia pullulans;* and other oligosaccharide-metabolizing bacteria, including but not limited to *Bacteroides succinogenes,* Thermoanaerobacter species like *T. ethanolicus,* Thermoanaerobium species such as *T. brockii,* Thermobacteroides species like *T. acetoethylicus,* and species of the genera Ruminococcus (for example, *R. flavefaciens*), Thermonospora (such as *T. fusca*) and Acetivibrio (for example, *A. cellulolyticus*). Again, suitable transformation techniques are available for these different hosts.

The literature relating to microbes which meet the subject criteria is reflected, for example, in Biely [1985] Trends in Biotech. 3: 286–90, in Robsen et al. [1989] Enzyme Microb. Technol. 11: 626–44, and in Bèguin [1990] Ann. Rev. Microbiol. 44: 219–48, the respective contents of which are hereby incorporated by reference. Those skilled in this art will appreciate that many other hosts will be suitable for use in the present invention. Thus, suitable hosts can be identified by screening to determine whether the tested microbe transports and metabolizes oligosaccharides. Screening in this vein could be accomplished in various ways. For example, microorganisms could be screened to determine which grow on suitable oligosaccharide substrates, the screen being designed to select for those microorganisms that do not transport only monomers into the cell. See, for example, Hall et al. [1987], supra. Alternatively, microorganisms could be assayed for appropriate intracellular enzyme activity, e.g., β-xylosidase activity.

Exemplary of a selection regimen suitable for use in accordance with the present invention is one where minimal medium containing pectin is employed to isolate a soft-rot Erwinia strain from decaying plant materials. See Starr, "The Genus Erwinia," in Vol. II THE PROKARYOTES 1260–71 (Springer-Verlag 1981). Isolates which cause pitting in calcium stabilized pectin can be characterized further to confirm identity. See Bergey's Manual, Volume 1, at pages 469–76.

Suitable candidate strains of Klebsiella, abundant in pulp and paper waste (Huntley et al. [1976] J. Water Pollution Control Federation 48: 1766–1771; Knittel et al. [1977] Appl. Environ. Microbiol. 34: 557–63), can be obtained, for example, from waste streams of processing plants in Perry and Palatka, Fla. The presence of high numbers of Klebsiella in such waste may promote selection for particularly useful strains with optimal characteristics such as resistance to toxic chemicals and the ability to utilize oligosaccharides. Strains can be selected initially by growth on coliform-specific medium, see Seidler, "The Genus Klebsiella (Non-medical Aspects)," in II THE PROKARYOTES 1166–72, and further identified by indole-production, Voges-Proskauer reaction, citrate, etc. See Bergey's Manual, Volume 1, at pages 461–65.

Isolates of Klebsiella and Erwinia can be compared for their ability to degrade carboxymethyl cellulose, xylan-blue, methyl-umbelliferyl β-D-glucopyranoside, methyl-umbelliferyl cellobioside, methyl-umbelliferyl xyloside, and methyl-umbelliferyl arabinoside as model substrates for endoglucanse, xylanase, β-glucosidase, cellobiohydrolase, xylosidase and arabinosidase, respectively, on plates buffered at pH 6.0 (30° C.). Strains also should be screened for their ability to metabolize monosaccharides (hexoses and pentoses) as well as cellobiose, cellotriose, xylobiose and xylotriose. Disaccharides and trisaccharide levels can be tested in overnight tube cultures by means of thin layer chromatography to monitor utilization of saccharides during overnight incubation. Xylosidases can be generated from birchwood xylan (Sigma) by treatment with *C. thermocellum* xylanase.

Growth of promising strains can be further screened for ethanol tolerance, salt tolerance, and temperature tolerance in a manner essentially similar to that used for the selection of *E. coli* B. See Alterhum et al., [1989] Appl. Environ. Microbiol. 55: 1943–48; Beall et al., Biotechnol. & Bioeng. [1991] 38: 296–303. Although most isolates can be frozen in liquid nitrogen for storage, the three most promising strains from each group can be selected for further development. Stored strains may prove useful in future studies as sources of new polysaccharase genes.

Optimal strains should retain the ability to efficiently metabolize all constituents of lignocellulose (disaccharides, trisaccharides and monosaccharides), to grow in ethanol concentrations above 440 g/liter, to tolerate salt levels of 0.3 molar, to tolerate acetate levels of 0.2 molar, and to tolerate temperatures of 40° C. and to produce high levels of enzymes useful for cellulose, hemicellulose and pectin depolymerization with minimal protease activity. Some strains may also contain native xylanases or cellulases. After integration of foreign genes for alcohol production, optimal constructions should produce ethanol from all saccharides tested with greater than 90% of theoretical yield while retaining the useful traits above.

Additional studies can be done to evaluate overall pH and temperature optima of secreted cellulases and to determine thermal stability. This information can be helpful in designing optimal conditions for combined hydrolysis and fermentation processes.

(E) EXPRESSION OF HETEROLOGOUS POLYSACCHARASES: As described above, a preferred embodiment of the present invention contemplates production of recombinants which express heterologous polysaccharases, thereby reducing the need for commercial enzymes in the context of fermenting oligosaccharides. Exemplary polysaccharases include cellulolytic enzymes, hemicellulytic enzymes, xylanolytic enzymes and starch-degrading enzymes.

In one advantageous embodiment, the polysaccharase is thermostable. In this regard, for example, genes encoding thermophilic proteins from *Clostridium thermocellum* (celA, B, C and D) can be expressed individually at high levels as cytoplasmic products. Recombinantly reproduced enzymes are recovered by harvesting cells at the end of fermentation and then releasing the thermostable enzymes from those cells by heating, for example, to 60° C., a temperature at which they exhibit near maximal activity and good stability. Thereafter, the enzymes are allowed to act on a complex polysaccharide substrate for a predetermined period, e.g., on the order of twelve hours. Modifications which eliminate the signal portions of selected genes greatly enhance the activities which are produced in *E. coli,* and may have a similar effect in Klebsiella and Erwinia.

The celD gene is particularly preferred for use in this context, and celD-transformed recombinants within the present invention are suitable for the fermentation of a substrate like SOLKA-FLOC, a powdered cellulose product derived by mechanical comminution of purified wood pulp. As shown in Example 18 and FIG. 14 below, prehydrolysis of substrate with the celD-encoded enzyme can reduce the requirement for commercial cellulases to approximately ⅕ in relation to recombinants which lack celD. This approach of using enzymes, heterologously expressed and accumulated intracellularly, to "jump-start" saccharification of a complex substrate can be generalized, in accordance with the present invention, to any ethanologenic recombinant that is further transformed with a polysaccharase-encoding gene, the expression product of which can be recovered for the purpose of breaking down complex oligosaccharides (cellulose, hemicellulose, starch, glycogen, pectin, inulin, etc.). See Examples 17–19 below.

Thus, for example, cells from a previous fermentation can be used as a source of enzymes for each subsequent fermentation. Also, enzyme secretion is not required and, instead, the process takes advantage of intracellular accumulation to facilitate harvesting of enzymes. The highest level of recombinant enzyme is present initially rather than accumulating slowly during growth and fermentation. Furthermore, there is reduced risk of microbial contamination since oligosaccharide utilization is uncommon among microorganisms and, hence, fewer contaminating microflora are to compete for these sugars.

In another preferred embodiment, an ethanologenic recombinant as described above expresses a polysaccharase that is at least partially secreted from the host and catalyzes hydrolysis of a complex oligosaccharide extracellularly. Such a gene product could supplement the activity of one or more commercial enzymes, such as the products of cenA (endoglucanase) and cex (exoglucanase), conventionally supplied during saccharification and ethanol production. Illustrative of polysaccharase-encoding genes which could be used in this matter are the cellulase genes of *Cellulomonas fimi*, which are partially secreted (about 50% to 60%) when transformed into Klebsiella or Erwinia. In a laboratory strain of Erwinia transformed with the cex gene, for example, over 50% of the heterologous expression product is secreted into the broth.

The efficiency of such secretion should be increased by fusion to signal sequences for pullulanase in Klebsiella and for a pectate lyase in Erwinia, respectively. See Murooka [1990] Ferment. Technol. Ind. Appl. 40–45; Pugsley et al. [1990] Ann. Rev. Genetics 24: 67–90; He et al. [1991] Proc. Nat'l Acad. Sci. USA 88: 1079–83; Saarilahti et al. [1990] Gene 90: 9–14.

Of particular interest is an ethanologenic transformant within the present invention that expresses both a thermostable gene product in addition to a gene product which is secreted. Such a transformant would provide (1) via lysis, enzymatic activity for use in a pre-treatment to break cellulose or another complex substrate into simpler oligosaccharides and monosaccharides, and (2) via secretion, enzymes for continued depolymerization during fermentation.

Heterologous genes coupled with mutations or genetic modifications that overexpress native traits will prove useful under particular circumstances. For example, mutageneses and selection can be carried out to increase the level of expression of native endoglucanases in Erwinia strains. In some cases these are repressed by high concentrations of glucose. Selection for depressed mutants on glucose-CMC plates can be used to identify strains which have lost this control, some of which may over-produce these enzymes.

The skilled artisan will appreciate that many different polysaccharases can be employed in accordance with this aspect of the present invention. By the same token, a wide range of transforming vectors are available for use in accordance with this aspect of the present invention. Some routine experimentation may be necessary to achieve the optimal match of host and vector. For example, RSF1010-based vectors can be constructed, see Conway et al. [1987c] Appl. Environ. Microbiol. 53: 235– 41, and are preferred to the extent that their broad host range should allow introduction of heterologous genes into many gram-negative bacterial host, including all Erwinia and Klebsiella isolates, with selection for tetracycline resistance. By contrast, pUC-based plasmids may prove unstable in some Erwinia strains and, to that extent, would be less preferred.

Among other polysaccharase genes suitably used in the present invention are those that encode one of the cellulolytic activities listed below:

| Type of Enzyme | Substrate | | | | |
|---|---|---|---|---|---|
| | Crystalline cellulose | Carboxylate Cellulose (CMC) | Amorphous Cellulose | Cellotetrose | Cellobiose |
| Endoglucanase | − | + | + | + | − |
| Cellobiohydrolase | + | +/− | + | + | − |
| β-Glucosidase | − | − | − | + | + |

An endoglucanase hydrolyses β-1,4-glycosidic linkages randomly. It does not attack cellobiose but hydrolyzes cellodextrins, phosphoric-acid-swollen cellulose and substituted celluloses like CMC and HEC (hydroxyethyl cellulose). Some endoglucanases also act on crystalline cellulose.

By contrast, a cellobiohydrolase acts on cellulose and, in particular, splits off cellobiose units from the non-reducing end of the chain. Cellobiohydrolase hydrolyses cellodextrins but not cellobiose. β-Glucosidase hydrolyses cellobiose and cellooligosaccharides to glucose, but does not attack cellulose or higher cellodextrins.

In addition to the cellulase-encoding genes from *C. thermocellum* mentioned above, other genes that code for cellulolytic activity have been characterized. See, for example, Bèguin [1990] Ann. Rev. Microbiol. 44: 219–48, the contents of which are hereby incorporated by reference. Moreover, such genes are readily available, for example, through GenBank database, which contained listings of 13 endoglucanases, 3 cellobiohydrolases, and 3 β-glucosidases, inter alia, as of March 1991.

By the same token, genes that code for a xylanolytic enzyme can be used as described above, pursuant to the present invention. Of particular interest in this regard are genes encoding a xylanolytic enzyme selected from the group of endo-1,4-β-xylanase, β-xylosidase, α-glucuronidase, α-L-arabinofuranosidase, acetylesterase and acetylxylanesterase. Exemplary of this group are the respective expression products of the *C. thermocellum* xynZ gene and the *Butyrivibrio fibrisolvens* xylB gene, both expressed in ethanologenic transformants described below (see Example 17). Again, genes for such xylanases are readily available as reflected in GenBank's entries for 7 endo-1,4-β-xylanases, 5 β-xylosidases and 1 α-L-arabinofuranosidase as of March 1991.

Similarly, genes can be used in the present invention that code for enzymes involved in the breakdown of starch. Illustrative enzymes of this sort are listed below, along with biological source and other characterizing information:

| Enzyme | Type | Source | Amount | Activity |
|---|---|---|---|---|
| α-Amylase | Liquefying | *Bacillus subtilis*[a] | 0.06% wt of starch | Decreases viscosity (Cleaves 1–4, pH 5.5, 70° C.) |
| | | *B. licheniformis* | 0.06% wt of starch | Decrease viscosity (92° C.) |
| | | Barley malt | 0.5–1.0 wt of grain | Decreases viscosity (60° C.) |
| β-Amylase | Saccharifying | Barley malt[b] | 2.0% wt of grain | Generates maltose (Cleaves 1–6, pH 5.3, 60° C.) |
| Glucoamylase | Saccharifying | *Aspergillus niger*[b] | 0.18% wt of starch (1.7 L/ton) | Generates glucose (Cleaves 1–6, pH 5.0, 60° C.) |
| Pullulanase | Saccharifying | *B. acidopullulyticus* | 0.2% wt of starch (2.0 kg/ton) | Cleaves 1–6, pH 5.0, 60° C. |

[a]Endoamylase
[b]Exoamylase

Enzymes involved in starch breakdown are exemplified below by a *B. stearothermophilus* α-amylase and a *T. brockii* pullulanase. Such genes are likewise readily available, as reflected by GenBank's entries, as of March 1991, for 190 α-amylases, 3 β-amylases, 8 glucoamylases, and 3 pullulanases. Other polysaccharases such as β-glucanase, arabinosidase, mannanase, pectin hydrolase, and pectate lyase also are available readily through GenBank or from literature which teaches the cloning of such genes.

Bacillus polysaccharase genes often are expressed well in *E. coli* and, hence, should be suitable for use in enteric bacteria generally, pursuant to the present invention. Indeed, members of the Bacillaceae secrete a wide variety of such enzymes, including amylases, β-glucanases and hemicellulases, and a number of species secrete cellulases, including strains of *B. subtilis, B. polymyxa, B. licheniformis* and *B. cereus*. See Bèguin [1990], supra, and Robson et al. [1989] Enzyme Microb. Technol. 11: 626–44, the contents of which are hereby incorporated by reference. If a signal sequence associated with a heterologous polysaccharase gene proves non-functional in the host of choice, such as Klebsiella or Erwinia, it is a routine expedient to replace this signal by gene fusion to a signal sequence from the host in the event that, as described above, secretion of heterologous enzyme is desired.

Strains of *Bacillus stearothermophilus* are a source of genes encoding thermostable hydrolase and other activities, such as endogluconase (CMCase and nitrophenyl-cellobiosidase activities), which can be exploited to advantage in the present invention. Many genes of this type have been characterized, and are available through GenBank or from the relevant literature. See also Bèguin [1990], supra.

(F) SELECTION AND TRANSFORMATION OF HOSTS: To select strains as potential hosts for heterologous polysaccharase genes, recombinant strains within the present invention which contain integrated genes for alcohol production can be tested in fermentations using SOLKA-FLOC as the cellulosic substrate, together with a commercial cellulase for hydrolyzing the cellulose. A dose-response curve can be generated for ethanol production and rate of conversion as functions of dilution of commercial enzyme preparation. The industrial cellulase preparations (e.g., SPEZYME, MULTIFECT AND CYTOLASE [Genencor]) can be used in these experiments, for example, using pH-controlled fermentations at 35° C. and pH 6.0.

Addition of a heterologous polysaccharase then can be accomplished in the manner illustrated in Examples 17–19. For example, polysaccharase genes which are selected as particularly advantageous can be integrated using homologous recombination. Tetracycline (5 mg/liter) can be used for selection of initial recombinants and higher levels will be used to select mutants with elevated expression of useful genes. Fusaric acid selection can be used to inactivate the tetracycline resistance (tet) gene so that multiple enzymes can be added sequentially by the same protocol. These constructs can be evaluated for utility in the single stage and multistage cellulose fermentation processes.

A preferred route to developing ethanologenic, gram-positive organisms, such as a *B. subtilis* or a Cellulomonas strain, involves chemical mutagenesis coupled with screening of colonies by the use of antibodies against *Z. mobilis* pyruvate decarboxylase, thereby to detect increases in expression. Clones thus identified for displaying higher expression are studied to determine the mechanism(s) responsible for the phenotype. Such mutants may prove useful per se and, in addition, should serve well for the expression of other heterologous proteins in an organism which is generally regarded as safe (GRAS).

In transforming ethanologenic hosts with heterologous cellulase genes, thereby to achieve high intracellular concentrations of active enzyme, some additional, routine genetic manipulation or screening may be required, depending upon the host and cellulase selected. For example, proteases secreted by a host may present a barrier to heterologous expression in accordance with the present invention. Several approaches can be used, such as indicator plates for proteinase activities and selection for higher levels of target enzyme, to obtain mutants in which this problem has been minimized.

Moreover, there often is a price to pay, in terms of growth rate and efficiency, for the production of any heterologous protein, including a polysaccharase. This "gene burden" can be minimized by testing multiple constructions of particularly useful genes. The site of integration also may affect the apparent "gene burden" and, therefore, can be a variable for testing in accordance with the present invention.

The constructs prepared along these lines then can be used in cellulose fermentation trials, as illustrated in Example 18 below, to evaluate effectiveness in combination with commercial enzymes and for efficiency of fermentation. Thus, one can test the ability of cellulases that are secreted by the transformed host to replace commercial cellulases in single-stage processes where commercial cellulases are added at the time of inoculation with ethanol-producing, cellulase-secreting recombinants. The utility of thermophilic cellulases can be tested by adding ethanologenic cells containing these enzymes from a prior fermentation to cellulose suspensions at 60° C. Incubation can be continued for a period of time, such as 12 hours, under optimized conditions for the particular enzyme. The temperature and pH can be lowered in most cases to provide optimal conditions for a commercial enzyme, such as SPEZYME, MULTIFECT and CYTOLASE, and incubation continued for 12 hours. After lowering the temperature to 35° C., and raising the pH to 6.0, broth can be inoculated with recombinant ethanologen. Ethanol yields and rates can then be determined. Many variations of this approach can be used to accommodate the specific requirements of individual enzymes for optimal activity.

The molecular genetic methods to be used are well-documented. See, for example, Maniatis et al., MOLECULAR CLONING: A LABORATORY MANUAL (Cold Spring Harbor Laboratory, 1989); Ausubel et al., CURRENT PROTOCOLS AND MOLECULAR GENETICS (John Wiley & Sons, 1987). Fermentations can be conducted at the pH levels described above and in the Examples. Ethanol can be measured by gas-liquid chromatography, as described by Goel et al. [1984] Biotechnol. Lett. 3:177–182, and Dombek et al. [1985] Appl. Environ. Microbiol. 51:197–200. Monomeric sugars can be determined colorimetrically and by HPLC. See Ashwell [1966] Methods Enzymol. 8:93–95; Wood et al. [1988] Methods Enzymol. 160. Oligosaccharides can be analyzed by HPLC and thin-layer chromatography. Cultures can be grown in either complex media such as Luria broth or in mineral salts. See Starr, Vol. II THE PROKARYOTES 1166–1172, 1260–1271 (Springer-Verlag, 1981); Mizutani et al. [1986] Biotechnol. Bioeng. 28: 204–09. Organisms can be maintained on solid medium containing 1.5% agar, and stocks can be stored in glycerol at −70° C.

Cellulase enzymes can be assayed essentially as described by Curry et al. [1988] Appl. Environ. Microbiol. 54: 476–484, and by Gripenet et al. [1988] J. Bacteriol. 170: 4576–4581. Exoglucanase activity can be determined using p-nitrophenylcellobioside as a model substrate. Carboxymethyl cellulase (endogluconase) activity can be measured as the release of reducing sugar. Cellulase activity also can be assayed by the conventional approach of measuring the release of reducing sugars from filter paper. Methyl-umbelliferyl derivatives, CMC and pectate can be used to prepare indicator plates for qualitative comparisons, thereby to identify strains which are high-level producers of an enzyme hydrolyzing any of these substrates.

(G) IMPROVING ALCOHOL TOLERANCE AND PRODUCTION OF TRANSFORMANTS: Maximum levels of ethanol produced with ethanologenic recombinants of the present invention can exceed 1M, for example. Ethanol production can exceed 1.5M for fermentation of lactose by an *E. coli* transformant, KO11, which is deposited as ATCC 55124. Enhanced alcohol tolerance in the ethanologenic recombinants of the present inventions therefore is particularly useful. Changes affecting membrane lipids and/or stress proteins are likely bases for such improvements. The *Z. mobilis* adhB, a component of a preferred ethanologenic operon (pet) within the present invention, also has been identified as a prominent *Z. mobilis* stress protein, responsive both to temperature and to alcohol. See Haejung et al. [1991] J. Bacteriol. 173: 5975–82. Other *Z. mobilis* genes which encode a stress protein should be useful in the same context. To the end of obtaining such genes, genes such as those found in *E. coli* which express major stress proteins, as reported by Johnson et al., [1989] J. Bacteriol. 171: 1590–96, Ang et al. [1989] J. Bacteriol. 171: 2748–55, Lipinska et al. [1988] Nucleic Acids Res. 16: 7545–61, and Fayet et al. [1986] Mol. Gen. Genet. 202: 435–45, can be used as probes to isolate corresponding genes from *Z. mobilis*.

It is likely that lipid-synthesis genes also will prove useful for ethanol tolerance. Other genes useful for ethanol tolerance can be selected by transforming libraries directly into ethanologens and enriching by serial passages in fermentation broth in which excess sugar levels are maintained to allow further growth of ethanol-resistant organisms after ethanol levels exceed the tolerance of the original inoculum. Chemostat approaches may also be particularly good for these selections.

Gene libraries of the highly ethanol resistant *Lactobacillus homohiochii* and *L. heterohiochii*, see Ingram [1990] Critical Rev. Biotechnol. 9: 305–19, also can be tested in these enrichments. Since these microbes effect spoilage in sake, they tolerate alcohol levels on the order of 15% v/v (over 2.5M). By this approach, therefore, recombinant strains can be developed which should be capable routinely of producing ethanol levels of at least 80 grams per liter.

Further still, the glycolytic enzymes of *Z. mobilis* may be used to enhance ethanologenic recombinants of the present invention. That is, the expression of one or more of the 13 genes that encode those glycolytic enzymes should increase glycolytic flux and, hence, the rate of ethanol production.

(H) PROCESS DESIGN: Numerous fermentation processes can be constructed, in accordance with this description, to implement the present invention. Some ethanol conversion processes employ simultaneous saccharification and fermentation (SSF), whereby both the enzymatic break down of biomass and the fermentation of the resulting sugars are combined in one process. The reaction conditions in which the enzymes function, therefore, must be compatible with the reaction conditions in which the fermentation organisms function. Such a requirement for reaction conditions, however, has attendant drawbacks.

It is well known, for example, that enzymes can suffer from "feedback inhibition" such that the rate of their activity is inversely proportional to the concentration of sugar in the reactor. That is, if the concentration of soluble oligosaccharides and/or monosaccharides in the reactor becomes too high, additional enzymatic production of the corresponding oligosaccharides and/or monosaccharides is significantly reduced or stopped altogether. Similarly, if the concentration of alcohol produced in the fermentation reaction is too high, the activity of the fermenting organisms is reduced or stopped altogether. Thus, the time for complete simultaneous saccharification and fermentation can be prohibitively high. Indeed, it is typical in these reaction systems for full enzymatic hydrolysis to take anywhere from about five to ten days.

Advantageously, however, it has been discovered that a significant improvement in efficiency can be obtained by utilizing a process having at least two stages: a saccharification stage, where biomass is contacted with polysaccharase to break down the oligosaccharides therein into simpler oligosaccharides and/or monosaccharides, and a subsequent fermentation stage in which the simpler oligosaccharides and/or monosaccharides are fermented to ethanol. As discussed below, the two stages advantageously will be conducted separately since the optimum conditions for carrying out each stage differ significantly.

Typical examples of biomass which may be used in this process include, for example, municipal solid waste, waste paper, pulp and paper sludge, pulped fibers, pulped wood, agricultural waste, sugar cane bagasse, corn stalks, corn cobs, rice hulls and other natural sources of biomass. Prior to the saccharification stage, such biomass generally will be pretreated by one or a combination of several known pretreatment methods including grinding, milling, pulping, acid and/or steam pretreatment. The use of a dilute acid serves to solubilize the hemicellulose present in the biomass and reduce the hemicellulose content of the biomass. The hemicellulose content of the biomass, which depends upon the particular type of biomass, typically is within the range of from about 1% to about 50%. For example, sugar cane bagasse typically comprises about 33% hemicellulose.

If the hemicellulose content of the pretreated biomass is above about 20%, the pretreated biomass preferably is washed to remove some of the higher molecular weight sugars present therein. If the hemicellulose content is below about 10% by weight, washing is not economical and, therefore, not performed. Washing the pretreated biomass permits the lignin to be separated more readily from the biomass, thereby exposing cellulose to more aggressive enzymatic attack in the saccharification stage. Various known methods can be employed to wash the biomass. Conventional vacuum belt washers, employing countercurrent operation, are preferred to minimize the amount of wash water needed. Other known washing methods include vacuum filtration and screw pressing with a washing stage. Use of the various washing techniques depends on the concentration of hemicellulose, the cost of washing and the desired concentration of hemicellulose in the resulting sugar solution which is to be provided to the saccharification stage.

The desirability of washing also depends upon the type of pretreatment employed. For example, if the biomass is simply ground or milled, washing is not required. Washing typically is required when the biomass is pretreated with an acid that solubilizes the hemicellulose.

In a preferred embodiment, the biomass is treated for a period of from about 20 to about 40 minutes with dilute acid at a pH of from about 1 to about 2 and at temperature of from about 140° C. to about 150° C.

For the saccharification stage, many different types of reactor vessels can be employed. Suitable reactors include conventional batch and fed batch reactors. Preferably, a fed batch reactor is used so that biomass can be continually added to maintain the desired percent solids concentration. Typically, there will be a high solids concentration in the reactor and thus a reactor providing a high degree of agitation also is preferred. There are a variety of methods known in the art which effect agitation including, for example, turbine impellers, axial flow turbines, ribbon mixers, side turbine pumps, vertical turbine pumps, and the like.

In the saccharification or "enzyme" reactor, the biomass generally is subjected to enzymatic hydrolysis at the maximum solids concentration permitted by the particular type of mixing mechanism employed, although optimum levels at less than the maximum concentration may be learned by practice of the invention. Skilled artisans will appreciate that the maximum solids concentration is a function of the biomass utilized, with different types of biomass having different properties. For example, waste paper biomass tends to be hygroscopic and viscous whereas bagasse is not. The solids concentration can vary from about 5% to about 20% by weight, and preferably is within the range of from about 7% to about 15% by weight.

In addition to the biomass, saccharifying enzymes also are added to the reactor. The enzymes may be obtained separately, or prepared as part as the overall process in a manner as discussed above, e.g., using thermostable enzymes accumulated in the fermenting microorganisms. Suitable enzymes, which include those described above, are those which are capable of effectively breaking down the biomass into oligosaccharides and/or monosaccharides. Also, water may be added to the reactor to achieve the desired solids concentration.

Saccharification generally is carried out at a temperature within the range of from about 40° C. to about 60° C.

Preferably, the temperature is within the range of from about 50° C. to about 60° C., and more preferably within the range of from about 50° C. to about 55° C. Such temperatures favor the enzymatic breakdown of the biomass. The pH of the reactor can be from about 3.5 to about 6.0, and preferably is from about 4.5 to about 5.0.

As discussed above, in the enzyme reactor feedback inhibition can decrease enzymatic production of soluble oligosaccharides and/or monosaccharides as the concentration of the corresponding oligosaccharides and/or monosaccharides increases. Thus, it is preferable that a solution of oligosaccharides and/or monosaccharides be continuously withdrawn from the enzyme reactor. Further, the concentration of solids in the enzyme reactor decreases as enzymatic hydrolysis of biomass progresses and thus, it also is preferable to continuously add biomass to the reactor. By continuously adding and withdrawing feed and product streams from the reactor, therefore, the concentration of oligosaccharides and/or monosaccharides in reactor can be maintained within a desired range. For this reason, therefore, a fed batch reactor is preferred over a conventional batch reactor. Typically, the concentration of oligosaccharides and/or monosaccharides in reactor is within the range of from about 1% to about 3% by weight. If the concentration exceeds about 5%, enzymatic hydrolysis of the biomass may be significantly inhibited.

The sugar solution containing oligosaccharides and/or monosaccharides obtained from the enzyme reactor can be added to the fermentor directly, although generally it is preferred that the solution undergo one or more treatments before the oligosaccharides and/or monosaccharides finally reach the fermenting reactor. Typically, such treatment(s) will be separation processes, for example filtration, ultrafiltration, centrifugation and reverse osmosis treatments, which can carry out the objectives, inter alia, of (1) providing to the fermentor a solution having a high concentration of the oligosaccharides and/or monosaccharides and (2) recycling useable materials when possible or desirable. Skilled artisans readily will recognize many types of separations or treatments which can be used to achieve the same objectives.

The solution/slurry obtained directly from the enzyme reactor will contain suspended solids, enzymes and soluble sugars. Appropriate filters include those which separate gross solids from gross liquids, for example, a stationary screen such as a DSM screen, or a cartridge or vacuum filter. The solids obtained from the initial filtering may be discarded, treated further and/or returned to the enzyme reactor, and the solution containing the oligosaccharides and/or monosaccharides can then be sent to the fermentor or treated further.

One such further treatment comprises ultrafiltration. Typically, an ultrafiltration unit comprises an ultrafiltration membrane which separates molecules having a molecular weight above a predetermined value from those having a molecular weight below that value. Such membranes can be referred to as upper molecular weight cut-off ultrafiltration membranes. Any molecular weight cut-off membrane may be used in the present invention as long as it enables separation of the dilute suspended solids and soluble fraction of higher molecular weight oligosaccharides from the lower molecular weight oligosaccharides and/or monosaccharides. Typical molecular weight cut-offs are within the range of about 5,000 to about 30,000, and preferably within the range of about 24,000 to about 26,000. However, other molecular weight cut-offs may be used.

The ultrafiltration unit yields two solutions. The first or "product" solution, which comprises predominantly molecules having a molecular weight below the cut-off, including preferably most of the oligosaccharides and/or monosaccharides, is sent to the fermentor or treated further before being sent to the fermentor. The second solution, which comprises predominantly molecules having a molecular weight above the cut-off, can be discarded, treated further and/or returned to the enzyme reactor.

Another such further treatment includes reverse osmosis, in which water is separated from the solution to yield a first stream comprising predominantly water and a second stream comprising the oligosaccharides and/or monosaccharides from the enzyme reactor. The first stream comprising predominantly water can be discarded, treated further and/or returned to the enzyme reactor to help maintain a relatively constant solids concentration therein. The second stream comprising the oligosaccharides and/or monosaccharides can then be sent to the fermentor or treated further before being sent to the fermentor.

Before entering the fermentor, the temperature and pH of the solution comprising the oligosaccharides and/or monosaccharides can be adjusted in accordance with the desired operating conditions of fermentor. The optimum temperature and pH can depend upon the particular microorganism used for fermentation. Typically, fermentation is carried out at a temperature within the range of from about 25° C. to about 40° C. preferably within the range of from about 30° C. to about 35° C. The optimum pH can vary from about 4.5 or lower for some microorganisms such as some yeasts, up to about 6.0 to about 6.7 or higher for other microorganisms, such as the recombinant organisms described above. Determining the optimum pH for any given microorganism is well within the routine skill of the skilled artisan.

In the fermentor, any fermenting microorganism may be employed in the fermentor as long as it is capable of fermenting monosaccharides and/or oliosaccharides to ethanol. For example, any of the recombinant microorganisms discussed above may be used. Typical fermentations using those microorganisms yield a product solution of about 4% to about 5% by weight alcohol. Also, other known microorganisms may be used, for example conventional yeasts, many of which are capable of fermenting glucose at high ethanol concentrations. Such yeasts may permit a more efficient production of ethanol. For example, using such yeasts, alcohol yields within the range of from about 8% to about 10% by weight may be realized. Yeasts which also are capable of fermenting oligosaccharides can be used. Moreover, compatible combinations of microorganisms may be used.

Nutrients also may be added to the fermentor to aid in growth of the microorganisms. Typical nutrients, which are well known to skilled artisans, include minimum nutrient broth, yeast extract, corn steep liquors and the like. Likewise, additional enzymes can be added to the fermentor to provide further production of lower oligosaccharides and monosaccharides therein. Alternatively, as discussed above, such enzymes can be produced in situ by the fermenting microorganism. Where conventional yeast is used as the fermenting organism, it may be especially desirable to make a substantial addition of enzymes, such as those discussed above, which are capable of converting oligosaccharides into glucose independent of the concentration of alcohol in fermentor. The glucose then is fermented by the conventional yeast.

The fermentor typically is an anaerobic fermentor which may be continuous, batch fed, or simple batch. Carbon dioxide, which is byproduct of fermentation, can be removed continuously from the fermentor. If a continuous or batch fed fermentor is used, then optionally, on a continual basis, fluid (beer) having an ethanol concentration of from about 0.5% to about 5% or higher, and typically from about 1% to about 2%, can be drawn off from the fermentor and treated to recover ethanol, for example, by evaporation and/or distillation. The beer removed from the evaporator will have an ethanol concentration on the order of less than about 0.5%, i.e., generally about 0.3%, and thus can be returned to the fermentor. In this way, the alcohol concentration in the fermentor can be kept within a desired range to maximize the ethanol production, i.e., below the concentration at which ethanol production will decrease or cease. The ethanol concentration above which the fermenting organisms will decrease or cease production will depend upon the particular microorganism used.

The processes of this invention will be illustrated below with reference to the configurations of FIGS. 19 and 20. These configurations are solely for illustration purposes and should not be construed in any way as limitations of the invention. Indeed, skilled artisans readily will recognize other configurations which can be used in accordance with this invention.

Figure 19:
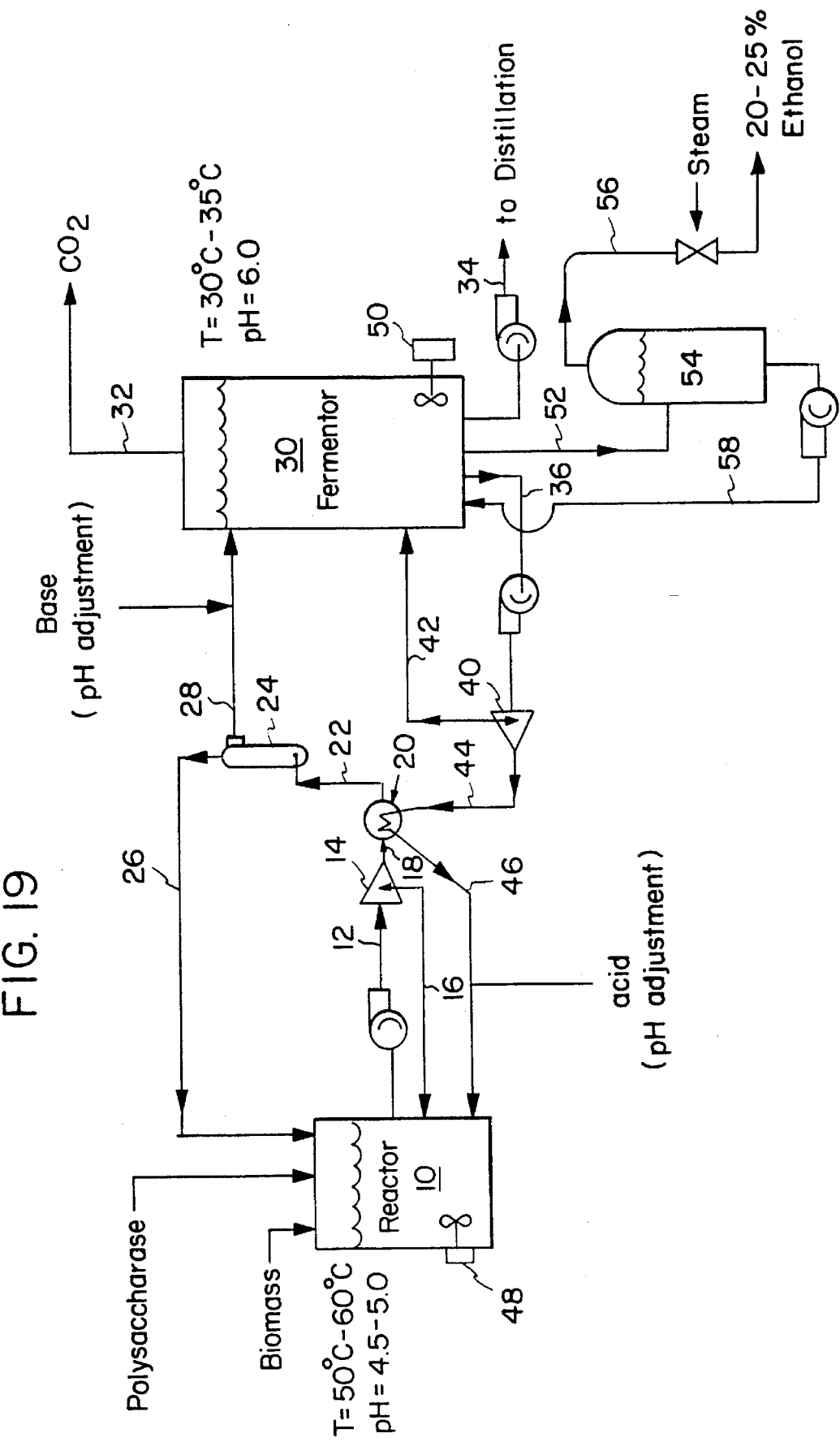
FIG. 19 comprises a schematic illustration of a fermentation process according to the invention.

FIG. 19 illustrates that there can be some recycling of materials from the fermentation stage to the saccharification stage. Further, since the recycled materials will be at the fermentation stage temperature, e.g., from about 30° C. to about 35° C. those materials advantageously may be used in a heat exchanger to cool the higher temperature effluent from the saccharification stage before it is introduced into the fermentation stage.

With reference now to FIG. 19, polysaccharase and pretreated biomass are provided to the enzyme reactor where the starting oligosaccharides in the biomass are broken down into simpler oligosaccharides and/or monosaccharides. The enzyme reactor 10 is maintained at a temperature of from about 50° C. to about 60° C. and a pH of from about 4.5 to about 5.0. A mixture of solids and liquid is drawn from enzyme reactor 10 through conduit 12 and into a solid/liquid separator 14, where the solid and liquid are separated, for example, by centrifugation or filtration.

The separated solids are returned to the enzyme reactor 10 through conduit 16. The effluent from the separator is then passed through conduit 18 to heat exchanger 20, where it is cooled to about 30° C. to about 35° C. The effluent is then passed through conduit 22 to membrane separator 24 which separates large molecular weight polysaccharases, which are then returned via conduit 26 to the enzyme reactor 10. The membrane filter, for example, can be an ultrafilter such as the CARRE filter by DuPont®, that has a removal rating of from about $10^{-3}$ to about $10^{-4}$ microns. Alternatively, the membrane separator 24 can be eliminated and the effluent introduced directly into fermentor 30. The remaining sugar solution, which comprises oligosaccharides and/or monosaccharides, is then transferred via conduit 28 to the fermentor 30. Prior to entering the fermentor, however, the pH of the sugar solution can be adjusted to favor the optimum parameter of the fermenting microorganism, for example, by adding acid or base.

Carbon dioxide is drawn off from the fermentor through conduit 32. Effluent is drawn from the fermentor through line 34 to a distillation column (not shown) for distillation of ethanol. Mash is drawn from the fermentor and passed through line 36 into a solid liquid separator 40 (e.g., a centrifuge). Microorganisms which are separated in the separator 40 are returned to the fermentor through conduit 42. Effluent from the separator 40 is supplied to heat exchanger 20 to cool the effluent from the solid/liquid separator 14. After leaving the heat exchanger 20, the pH of the effluent is adjusted to favor the optimum conditions for saccharification, e.g., to from about 4.5 to about 5.0, and then the effluent is introduced to the enzyme reactor 10. Both the enzyme reactor 10 and the fermentor 30 can be provided with mixers 48 and 50, which can be any conventional type.

Optionally, on a continual basis, fluid (beer) having an ethanol concentration of from about 0.5% to about 5%, and typically from about 1% to about 2%, can be drawn off from fermentor 30 through conduit 52 and fed into evaporator vessel 54, where ethanol and water are evaporated and taken off through line 56 to another distillation stage (not shown). The concentration of ethanol in line 56 can be from about 20% to about 25%. The beer removed from evaporator 54 and returned to the fermentor 30 through line 58 will have an ethanol concentration on the order of less than about 0.5%, i.e., generally about 0.3%. In this way, the ethanol concentration in the fermentor can be maintained at a relatively low level, thereby maintaining a high rate of ethanol production in the fermentor.

Likewise, the effluent which is returned to the reactor 10 through conduits 36, 44 and 46 will have a lower ethanol concentration and thus provide less inhibition for the reactions in the reactor. Such a continuous process can be driven by the continual addition of biomass to the reactor 10. It may be desirable, however, to discharge the contents of the reactor 10 and the fermentor 30 on a periodic basis in order to discharge built-up solids and lessen the possibility of contamination.

Figure 20:
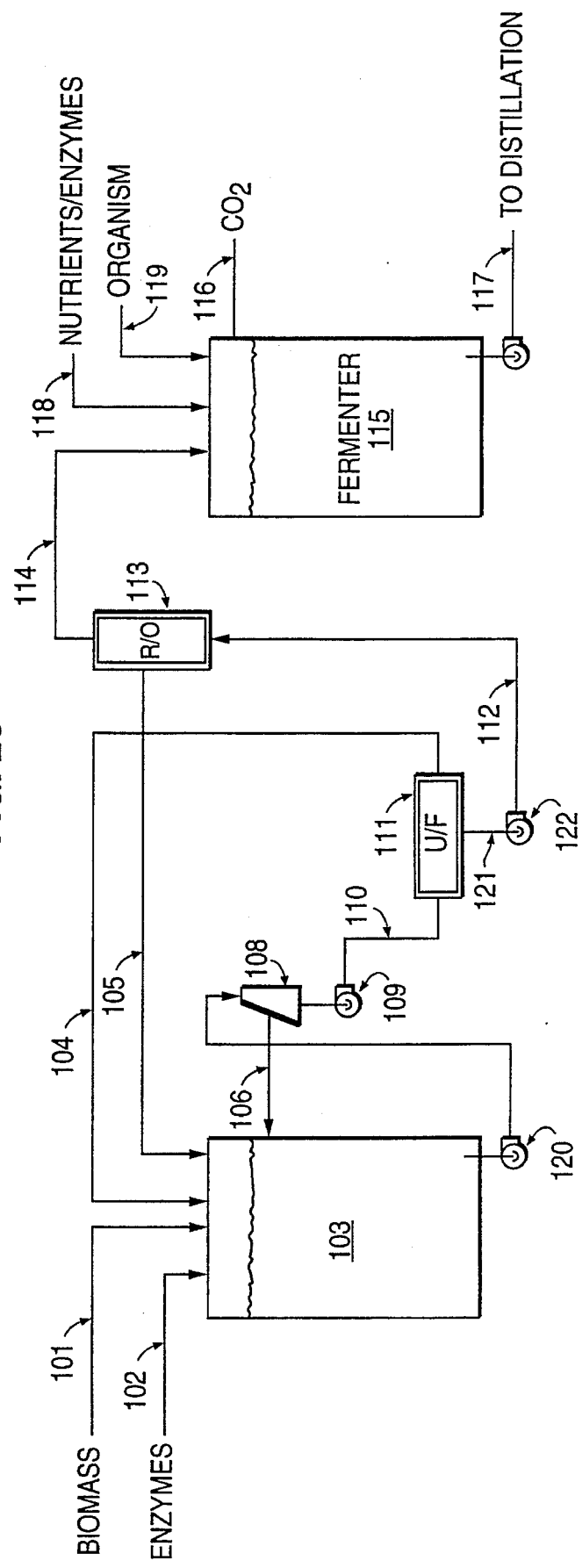
FIG. 20 comprises a schematic illustration of a fermentation process according to the invention.

FIG. 20 illustrates another possible configuration in accordance with this invention. In this configuration, biomass and enzymes are added to reactor 103 through conduits 101 and 102, respectively. A product stream comprising oligosaccharides and/or monosaccharides can be continuously withdrawn from fed batch reactor, e.g., by pump 120, which pumps the solution through conduit 107 to solid-liquid separator 108.

Solid-liquid separator 108 is depicted as a stationary screen, but may comprise any separator, for example centrifuge, filters, cartridge filters, vacuum filters, and the like. Solids which are separated by the screen 108 are recycled to reactor 103 through conduit 106. The liquid stream that passes through the screen, which may comprise dilute suspended solids, soluble sugars and enzymes, then is pumped via pump 109 through conduit 110 to an ultrafiltration unit 111, which preferably has an upper molecular weight cut-off of about 25,000. The ultrafiltration unit yields a first, i.e., product solution, and a second solution.

The ultrafiltration product solution, which comprises predominantly molecules having a molecular weight below about 25,000 including at least some of the oligosaccharides and/or monosaccharides in the solution obtained from separator screen 108, is withdrawn from ultrafiltration unit 111 by pump 122 through conduit 121. This product solution has a concentration of oligosaccharides and/or monosaccharides approximately equal to the concentration of oligosaccharides and/or monosaccharides in the enzyme reactor 103. The second solution, comprising predominantly molecules having a molecular weight above about 25,000, is recycled to reactor 103 through conduit 104. Of course, ultrafilters having a different upper molecular weight cut-off may be used.

This "ultrafiltration recycle loop," which includes separator 108 and ultrafiltration unit 111, thus maintains the concentration of oligosaccharides and/or monosaccharides in the reactor 103 within acceptable ranges so as to minimize feedback inhibition. Skilled artisans readily will recognize other configurations which will maintain the concentration of oligosaccharides and/or monosaccharides in the reactor 103 within acceptable ranges.

Pump 122 withdraws the ultrafiltration product solution from ultrafiltration unit 111 and feeds the solution through conduit 112 to reverse osmosis unit 113. The reverse osmosis unit 113, which concentrates the solution of oligosaccharides and/or monosaccharides by removal of water, provides two streams, i.e., a first stream 105 comprising predominantly water and a second stream 114 comprising the oligosaccharides and/or monosaccharides. It is preferable to concentrate the oligosaccharides and/or monosaccharides in solution prior to fermentation in order to maximize the concentration of the alcohol produced. The reverse osmosis membrane, which is more selective than the ultrafilter in that water will pass through the reverse osmosis membrane whereas sugars will not, thus allows such concentration of oligosaccharides and/or monosaccharides in solution. The first stream comprising water optionally then can be recycled to reactor 103 through conduit 105 to maintain the desired solids concentration, or used elsewhere. Those skilled in the art will recognize that the solids content in reactor also can be maintained by controlling the moisture content of feed biomass.

The second stream 114 comprising the oligosaccharides and/or monosaccharides typically comprises a higher concentration of oligosaccharides and/or monosaccharides than the solution entering reverse osmosis unit 113. The second stream 114 then can be added to fermentor 115 along with the fermenting microorganisms 119 and, optionally, additional nutrients and/or enzymes. From the fermentor, carbon dioxide is withdrawn through conduit 116 and a product stream is drawn off through conduit 117 to evaporation and/or distillation.

To obtain even higher concentrations of oligosaccharides and/or monosaccharides, the second stream can be recycled to the reverse osmosis unit 113, or sent to another or multiple reverse osmosis units. Typically, the concentration of sugar in the second stream 114, when compared to that in incoming stream 112, varies within the range of from about 2:1 to about 10:1, depending on the type of reverse osmosis unit used. Therefore, the concentration of sugar in rejected stream 114 likely can be anywhere within the range of from about 6% to about 24% by weight.

Skilled artisans will appreciate that the particular composition of oligosaccharides and/or monosaccharides in the second stream depends on the particular type of biomass used. Nevertheless, surprisingly it has been found that for at least some, if not all, forms of biomass, the second stream from the reverse osmosis unit typically comprises a high percentage of glucose, as well as other sugars such as xylose, and cellobiose and other oligosaccharides. Indeed, one might predict that oligosaccharides would be more prevalent because they are formed in the enzyme reactor before monosaccharides are formed. Also, feedback inhibition should decrease the rate of production of glucose and/or oligosaccharides as the concentration of each of these increases. While not intending to be bound by any theory, the present inventors hypothesize that the high concentration of glucose results because enzymes may be attached to cellobiose and higher oligosaccharides when subjected to ultrafiltration described above. If so, then such larger aggregate molecules may be separated from the lower molecular weight products such as glucose by the upper molecular weight cut-off ultrafiltration membrane.

Thus, the fermentation process discussed above can provide an efficient method of fermenting biomass to ethanol.

Those skilled in the art will recognize that many other additional steps and/or stages can be added to the fermentation process. For example, there can be biomass pretreatment stages, initial stages in which recombinant host cells that express and intracellularly accumulate polysaccharases are heated to lyse the cells and release the polysaccharase, and multiple fermentation stages, together with additional separations and recycling of solids and effluents along the way.

III. EXAMPLES

The present invention is further described by reference to the following illustrative examples, which should not be construed as limiting. All percentages are by weight and all solvent mixture proportions are by volume unless otherwise noted. Other methodological aspects of the examples are discussed below:

Organisms and growth conditions: *Escherichia coli* TC4, see Conway et al. [1987a], and plasmid-containing derivatives thereof were used. Plasmids containing the *Z. mobilis* pyruvate decarboxylase gene (pLOI276) and alcohol dehydrogenase B gene (pLOI284) have been described by Conway et al. [1987b].

Strains and growth conditions: Plasmids pUC18 and pUC19 have been described previously, see Yanisch-Perron et al. [1985] Gene 33: 103–19), as has pLOI204 and pLOI295. See Conway et al. [1987b]; Ingram et al. [1987]. The construction and properties of pLOI292, pLOI291, pLOI297, pLOI308, pLOI308-2, pLOI308-5 and pLOI308-10 are described below.

Cultures were grown at 37° C. in Luria broth, see Luria & M. Delbruck [1943] Genetics 28: 491–511, which contained 50 grams of glucose per liter. Cells for enzyme analyses and inocula for fermentation studies were grown in tubes (13× 100 mm) containing 3 ml of broth at 37° C. in a tube rotator. Overnight cultures were diluted 100-fold into fresh medium. Aerobic cultures (50 ml of broth in 250 ml flasks) were shaken in a reciprocating water bath (120 oscillations per minute). Anaerobic cultures were grown in stoppered serum bottles (100 ml of broth in 130 ml bottles) with gyrator agitation (150 rpm) in a 37° C. incubator. Anaerobic cultures were vented with a 25-gauge needle to allow escape of gaseous fermentation products.

Growth was monitored spectrophotometrically with a Spectronic 70 spectrophotometer (Bausch & Lomb, Inc. Rochester, N.Y.) at 550 nm. Disposable culture tubes (10× 75 mm) were used as cuvettes. One absorbance unit under our conditions contained approximately 0.25 mg of cellular protein per ml. Growth was measured at $A_{550}$.

*Escherichia coli* hosts containing the plasmids of the subject invention have been deposited with the American Type Culture Collection (ATCC), 12301 Parklawn Drive, Rockville, Md. 20852 USA. The cultures have been assigned these accession numbers by the repository:

| Culture | Accession number | Deposit date |
| --- | --- | --- |
| *E. coli* pLOI308-10 | ATCC 67983 | May 15, 1989 |
| TC4(pLOI292) | ATCC 68237 | February 23, 1990 |
| TC4(pLOI308-11) | ATCC 68238 | February 23, 1990 |
| TC4(pLOI297) | ATCC 68239 | February 23, 1990 |
| TC4(pLOI295) | ATCC 68240 | February 23, 1990 |
| *E. coli* pLOI510 | ATCC 68484 | |
| *K. oxytoca* M5A1 (pLOI555) | ATCC 68564 | March 14, 1991 |

The subject cultures have been deposited under conditions that assure that access to the cultures will be available during the pendency of this patent application to one determined by the U.S. Commissioner of Patents and Trademarks to be entitled thereto under 37 CFR 1.14 and 35 USC 122. The deposits are available as required by foreign patent laws in countries where counterparts of the subject application or its progeny are filed. But it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms. That is, they will be stored with all the care necessary to keep them viable and uncontaminated for a period of at least five years after the most recent request for the furnishing of a sample of a deposit, and in any case, for a period of at least thirty years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Genetic techniques: Transformations, plasmid constructions, DNA digestions and analyses were carried out as previously described. Recombinants were selected on solid media (1.5% agar) containing 2 grams of glucose per liter and appropriate antibiotics. Recombinants containing functional ethanologenic genes from Z. mobilis were identified as oversized colonies growing on Luria agar plates which included glucose, and identification was confirmed by the observations of poor growth on Luria agar plates lacking glucose and of alcohol dehydrogenase expression on aldehyde indicator medium.

Enzyme assays: Cells were disrupted, heat-inactivated, and assayed for pyruvate decarboxylase activity (thermostable) as described previously. See Conway et al. [1987b]. Cells were prepared and assayed for alcohol dehydrogenase II activity in the direction of ethanol oxidation as described previously, except that cells were washed and disrupted in 30 mM potassium phosphate buffer to which solid ferrous ammonium sulfate (final concentration, 0.5mM) and sodium ascorbate (1 mM) had been freshly added. See Neale et al. [1986] Eur. J. Biochem. 154: 119–24. This modification, combined with the immediate assaying of alcohol dehydrogenase activity without storage, resulted in a much higher specific activity than that previously reported. For the purpose of calculating ethanol-production efficiency, cell mass was measured in terms of protein content per culture, using the Folin phenol reagent method of Lowry et al., J. Biol. Chem. 193: 265–75.

Analysis of fermentation products: Fermentation products were determined in clarified broth with a Millipore/Waters high-performance liquid chromatograph (Millipore Corporation Bedford, Mass.) equipped with a refractive index monitor and an electronic integrator. Separations were performed on an Aminex HPX-87H column (300 by 7.8 mm) purchased from Bio-Rad Laboratories, Richmond, Calif., at 65° C. at a flow rate of 0.25 ml/min (100 µl injection volume). Peaks were identified by using authentic standards. The two peaks eluting before glucose and the later unknown peak eluting at 45.4 to 45.8 minutes are components of uninoculated medium.

Example 1. Strain Construction

The sizes of the structural genes coding for pyruvate decarboxylase and alcohol dehydrogenase II are 1.7 and 1.1 kilobases, respectively, and these genes encode proteins with molecular weights of 60,000 and 40,100. These genes are each located on derivatives of pUC18 under the control of the lac promoter (FIG. 1). The two genes were combined by inserting the promoterless 1.4 kilobase fragment generated by restriction endonucleases EcoRI and SalI from pLOI284 (alcohol dehydrogenase) into the BamHI site downstream from the pyruvate decarboxylase gene in pLOI276. These clones were selected for resistance to ampicillin and for the presence and expression of alcohol dehydrogenase activity on a newly developed pararosaniline-ethanol indicator plate which detects the production of aldehydes. Clones containing the indicated construction, pLOI295, grew poorly on the surface of Luria agar plates (aerobic) in the absence of added glucose but grew to much higher densities than the plasmid-free strain and strains containing pLOI276 or pLOI284 on agar plates containing 2% glucose.

Recombinants containing the pet operon were readily detected as larger, more opaque colonies on Luria agar plates (aerobic) containing glucose. This difference in colony size and opacity has proven to be a useful marker for the identification of recombinants which contain plasmids expressing both alcohol dehydrogenase and pyruvate decarboxylate genes.

The complete base sequence of pLOI295 is known. The open reading frame for the gene coding for pyruvate decarboxylase begins 163 bases downstream from the lac promoter and ends with two stop codons 85 bases upstream from the open reading frame of the gene coding for alcohol dehydrogenase II. Both genes include sequences which resemble ribosome-binding sites immediately upstream from each open reading frame. The gene encoding alcohol dehydrogenase II contains a single stop codon followed by a palindromic sequence of 13 base pairs which serves as a transcriptional terminator.

Example 2—Expression of Z. mobilis Genes in E. coli

Both pyruvate decarboxylase and alcohol dehydrogenase II genes were expressed at high levels in E. coli under the control of the lac promoter singly (pLOI276 and pLOI284, respectively) and jointly. Pyruvate decarboxylase is not present in wild-type E. coli, but an inducible alcohol dehydrogenase is present at low concentrations. During growth of E. coli in the presence of glucose, the specific activities of the Z. mobilis enzymes declined by approximately 50%, which is consistent with glucose repression of the lac promoter. The specific activity of pyruvate decarboxylase, coded for by the proximal gene in the pet operon, was threefold higher in pLOI295 than in pLOI276. The specific activity of the product of the alcohol dehydrogenase II gene, the distal gene in the pet operon, was expressed in pLOI295 at twice the level in pLOI284.

Example 3—Fermentation of Glucose by Recombinant Strains

Figure 3A:
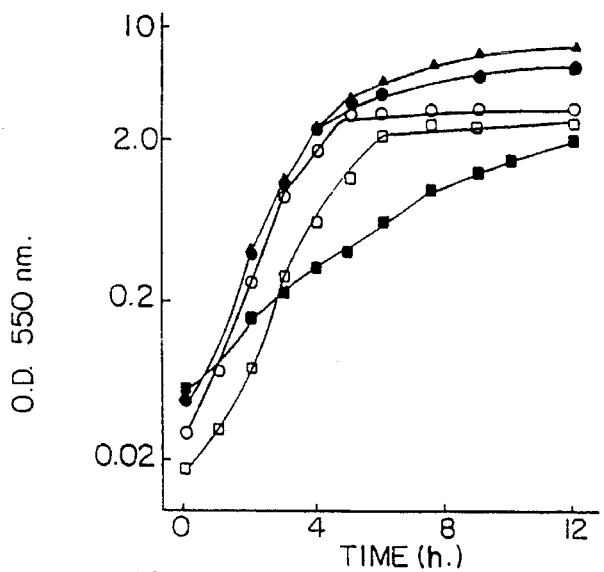
FIG. 3 illustrates growth and acid production by strain TC4 and recombinants containing plasmids encoding ethanologenic enzymes.
Figure 3B:
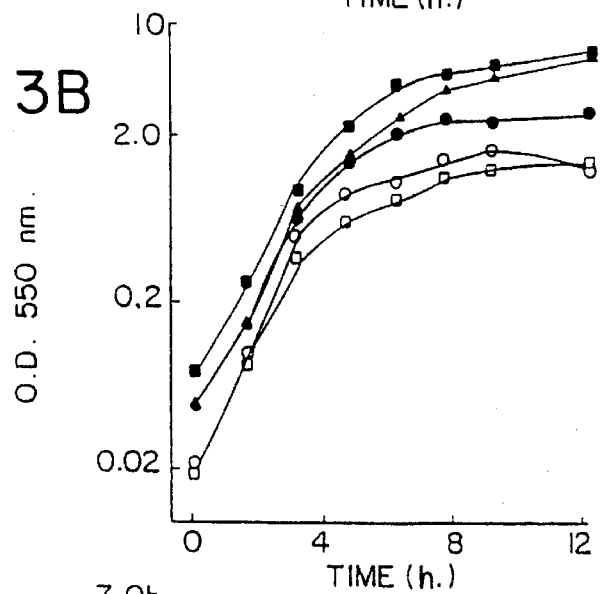
Figure 3C:
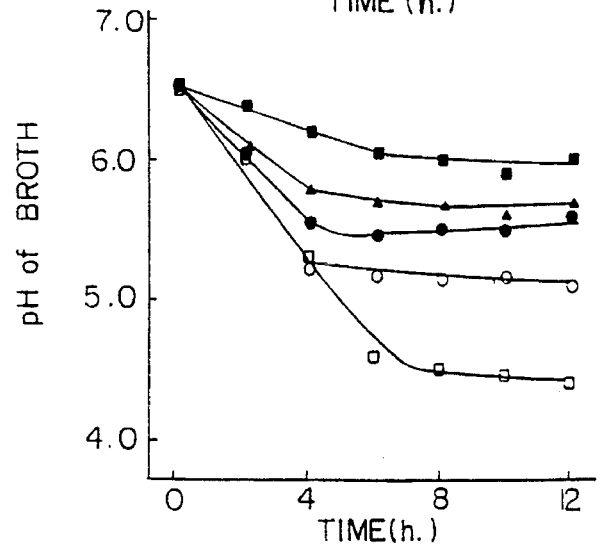

Expression of the pet operon in E. coli resulted in the production of ethanol as the primary fermentation product during anaerobic growth. The parent strain produced succinate (1.5 mM), lactate (18 mM), and acetate (7 mM) as major fermentation products (FIG. 3A). An identical fermentation profile was observed in cells containing pLOI284, which carries the alcohol dehydrogenase II gene (FIG. 3C). With pLOI276 carrying the gene coding for pyruvate decarboxylase, an ethanol peak is clearly evident (18 mM), equivalent to one-third of the accumulated fermentation products. This higher level of ethanol results from the combined activities of the pyruvate decarboxylase from Z. mobilis and the native E. coli alcohol dehydrogenase. With pLOI295 containing the pet operon (both pyruvate decarboxylase and alcohol dehydrogenase II genes from Z. mobilis), E. coli produced large amounts of ethanol (750 mM; 4.3%, vol/vol), which represented over 95% of the fermentation products.

The high levels of alcohol dehydrogenase and pyruvate decarboxylase produced in cells containing the pet operon dominated NADH oxidation in E. coli. Thus, the fermentation of this organism was converted to the equivalent of those of S. cerevisiae and Z. mobilis. During normal fermentative growth, pyruvate is converted to acetyl coenzyme A by the pyruvate dehydrogenase complex, to oxaloacetate (and on to succinate) by phosphoenolpyruvate carboxylase, to formate and acetyl coenzyme by pyruvate formate lyase, and to lactate by lactate dehydrogenase. This last pathway is the dominant route for the regeneration of $NAD^+$ in unmodified strains of E. coli. But the $K_m$s for bacterial lactate dehydrogenases are quite high, ranging from 10 to 1,000 mM (Garvie, E. I. [1980] "Bacterial lactate dehydrogenases," Microbiol Rev 44:106–139; Tarmy, E. M., and N. O. Kaplan [1968] "Kinetics of Escherichia coli B D-lactate dehydrogenase and evidence for pyruvate controlled change in conformation," J. Biol. Chem. 243:2587–2596). The $K_m$ of the pyruvate decarboxylase from Z. mobilis is 0.4 mM (Bringer-Meyer, S., K. -L. Schimz, and H. Sahm [1986] "Pyruvate decarboxylase from Zymomonas mobilis: Isolation and partial characterization," Arch. Microbiol. 146:105–110). The abundance of this enzyme, coupled with the lower $K_m$, effectively diverts the flow of pyruvate from glycolysis into ethanol.

High cell densities are also achieved during mixed growth conditions with moderate agitation or stirring of culture vessels in which gas exchange is not restricted. Under these conditions, a final pH of 6.3 or above was observed, depending upon the extent of aeration.

Example 4—Plasmid Constructions and Expression of Z. mobilis Ethanologenic Enzymes in E. coli Plasmid pLOI295 contains the Z. mobilis genes encoding pyruvate decarboxylase and alcohol dehydrogenase II under the control of the lac promoter. This construction is referred to as the pet operon and used as the source of ethanologenic genes for the construction of additional plasmids with alternative promoters. The EcoRI-SalI fragment from pLOI295 containing the ethanologenic genes was treated with the Klenow fragment of DNA polymerase to produce blunt ends. This blunt-ended DNA fragment was inserted into the SmaI site of pUC19 with the pdc gene immediately downstream from the lac promoter. The resulting plasmid, denoted pLOI293, contained the pet genes flanked by BamHI sites. Plasmids pLOI291 and pLOI292 (opposite orientations) were constructed by inserting the BamHI fragment containing the genes encoding the ethanologenic enzymes into the expression vector pLOI204. The BamHI fragment includes the ribosome-binding site, complete sequences for both genes, and a transcriptional terminator distal to adhB. In pLOI292, the two genes are expressed under the control of the Z. mobilis promoter contained in the original expression vector.

Plasmid pLOI308 was constructed to remove the pet genes from the control of the lac promoter but to retain the upstream BamHI site for the insertion of alternative promoters. Partial digestion of pLOI293 with BamHI and Klenow treatment were used to remove the BamHI site distal to the adhB gene. The ethanologenic genes were removed from this plasmid as a promoterless BamHI (immediately proximal to pdc)-EcoRI (distal to adhB) fragment, which was directionally inserted into the BamHI and EcoRI sites of pUC18 to produce pLOI308. This plasmid expressed low levels of adhB on aldehyde indicator plates but did not exhibit the large-colony phenotype associated with the other functional pet plasmids pLOI295, pLOI291, and pLOI292.

Chromosomal DNA from Z. mobilis was partially digested with Sau3A such that most of the DNA appeared to be less than 4 kilobases long. This unfractionated DNA was used as a source of promoter fragments and was ligated into the dephosphorylated BamHI site of pLOI308. Ampicillin-resistant recombinants with a well-expressed pet operon were identified as large colonies on Luria agar plates containing glucose. Three of the recombinant strains, pLOI308-2, pLOI308-5, and pLOI308-10, were selected for study. The Z. mobilis DNA fragments with promoter activity in these plasmids were 6, 2, and 2 kilobases long, respectively.

Table 1 summarizes the activities of pyruvate decarboxylase and alcohol dehydrogenase in overnight cultures of the recombinant E. coli. The activities of pyruvate decarboxylase ranged from 0.37 IU/mg of cell protein in strain TC4(pLOI291) to 8.23 IU in TC4(pLOI295). In terms of pyruvate decarboxylase activity, the recombinant strains of TC4 can be ordered as follows (highest to lowest): pLOI295>pLOI308-10>pLOI308-2>pLOI308-5>pLOI292>pLOI291.

TABLE 1

Expression of ethanologenic enzymes from Z. mobilis in E. coli

| Plasmid | Pyruvate decarboxylase | | Alcohol dehydrogenase | |
|---|---|---|---|---|
| | Sp act[a] | % Cell protein[b] | Sp act[a] | % Cell protein[c] |
| pLOI291 | 0.37 | 0.4 | 0.21 | 0.02 |
| pLOI292 | 0.48 | 0.5 | 0.30 | 0.03 |
| pLOI308-2 | 2.26 | 2.3 | 1.54 | 0.21 |
| pLOI308-5 | 1.11 | 1.1 | 0.76 | 0.10 |
| pLOI308-10 | 6.5 | 6.5 | 2.51 | 0.34 |
| pLOI295 | 8.2 | 8.2 | 9.65 | 1.4 |
| None | 0 | 0 | 0.08 | |

[a]Expressed as micromolecules of substrate utilized per minute per milligram of total cellular protein.
[b]Calculated assuming a specific activity of 100 for the pure enzyme.
[c]Calculated assuming a specific activity of 710 for the pure enzyme after subtraction of native alcohol dehydrogenase activity.

Alcohol dehydrogenase activities in the recombinant strains followed the same trend in terms of expression from different plasmids as did pyruvate decarboxylase. The alcohol dehydrogenase activities measured represent a combination of the native enzyme from E. coli and the Z. mobilis enzyme. The level observed in strain TC4 lacking a plasmid was relatively small in comparison to those observed in strains carrying plasmids with the Z. mobilis gene. The activities of the Z. mobilis enzyme (corrected for native E. coli alcohol dehydrogenase) ranged from 0.13 IU/mg of cell protein from strain TC4(pLOI291) to 9.6 IU in TC4(pLOI295).

Example 5—Growth of Recombinant Strains Containing the Ethanologenic Enzymes From Z. mobilis Shifting the catabolism of glucose to the production of ethanol also affected growth yield and pH drift of the growth medium. Although fermentation products are relatively nontoxic, they may accumulate to toxic levels during fermentation. During anaerobic growth in bottles containing Luria broth containing 10% glucose, the plasmid-free strain and the strain carrying pLOI284 (carrying the gene coding for alcohol dehydrogenase II) achieved a final density of 0.25 mg of cell protein per ml after 48 hr, with a final pH of 4.4. The cell density increased by twofold in the strain carrying pLOI276 (carrying the gene coding for pyruvate decarboxylase), with a final pH of 4.5. The final cell density of the strain carrying pLOI295 (pet operon) was 2.5 mg/ml, 10-fold higher than that of the control strain. The final pH was 4.7. At a density of 2.5 mg of cell protein per ml, magnesium appears to be limiting, and a 1.5-fold further increase in cell density is readily achieved by the addition of 0.5 mM magnesium sulfate.

The growth of the recombinant strains was examined under both aerobic and anaerobic conditions (FIG. 3). Under aerobic conditions (FIGS. 3A and Table 2), strain TC4 grew with a generation time of approximately 30 min during the most rapid phase of growth. Strain TC4 carrying the derivatives of pLOI308 exhibited equivalent maximal rates of growth, with generation times between 26 and 30 min. Strain TC4(pLOI295) grew poorly under these conditions (generation time, 71 min) and was accompanied by partial lysis. Strains TC4(pLOI291) and TC4(pLOI292) grew at intermediate rates, each with a generation time of 46 min.

TABLE 2

Maximal generation times, final cell densities, and final pHs of the broth during aerobic and anaerobic growth.

| Growth Condition | Plasmid | Cell density[a] (mg of protein/ml) | Generation time (min) | pH[a] Final |
|---|---|---|---|---|
| Aerobic | None | 0.7 | 29 | 4.4 |
| | pLOI291 | 0.7 | 46 | 5.3 |
| | pLOI292 | 1.3 | 46 | 5.1 |
| | pLOI295 | 1.1 | 71 | 5.7 |
| | pLOI308-2 | 1.7 | 27 | 5.5 |
| | pLOI308-5 | 0.8 | 30 | 5.0 |
| | pLOI308-10 | 2.5 | 26 | 5.0 |
| Anaerobic | None | 0.3 | 32 | 4.4 |
| | pLOI291 | 0.4 | 40 | 4.5 |
| | pLOI292 | 1.0 | 48 | 5.0 |
| | pLOI295 | 2.1 | 39 | 4.7 |
| | pLOI308-2 | 0.8 | 42 | 5.7 |
| | pLOI308-5 | 0.4 | 38 | 4.9 |
| | pLOI308-10 | 2.2 | 41 | 5.2 |

[a]Measured after 24 hr of growth.

Under anaerobic conditions (FIG. 3B and Table 2), the generation time for strain TC4 lacking a plasmid was 32 min, considerably shorter than that for the recombinant strains containing the ethanologenic enzymes. All of the recombinants exhibited similar maximal rates of growth, with generation times between 38 and 41 min, except for TC4(pLOI292), which grew somewhat more slowly, with a generation time of 48 min.

All of the recombinants except TC4(pLOI295) grew after 12 hr under anaerobic and aerobic growth conditions to cell densities equivalent to or higher than those of strain TC4 lacking a plasmid (FIGS. 3A and B). Table 2 summarizes the final cell densities of strain TC4 and the recombinants after 24 hr of growth. Under aerobic conditions, strain TC4 containing pLOI308-10 reached the highest cell density, followed by TC4 containing pLOI308-2, pLOI292, pLOI295 (with some lysis apparent), and pLOI308-5.

Under anaerobic conditions, the final cell densities of strain TC4 containing pLOI308-10 and pLOI295 were roughly equivalent, followed by those of TC4 containing pLOI292, pLOI308-2, pLOI308-5, and pLOI291.

Figure 4:
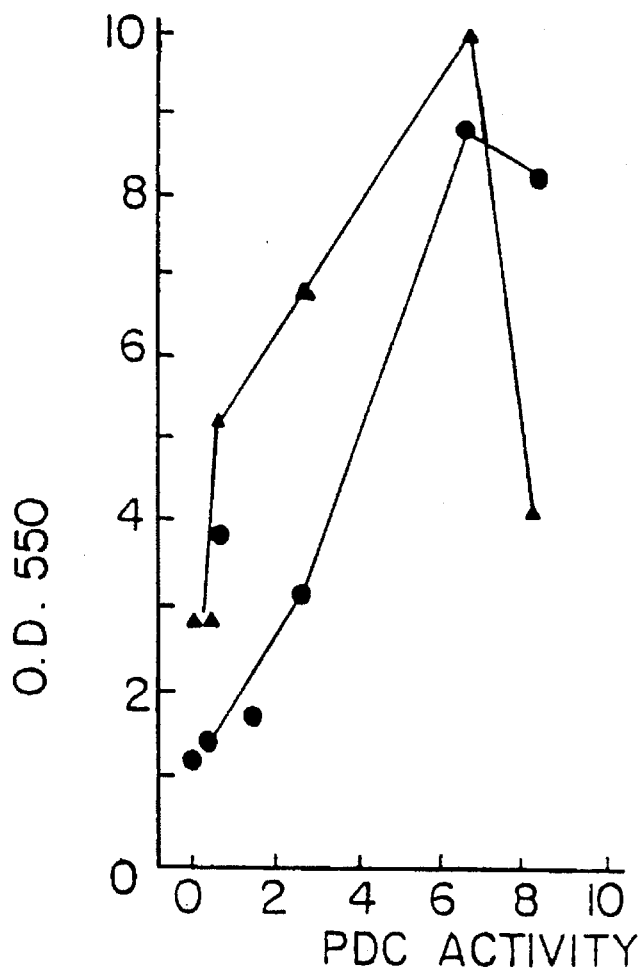
FIG. 4 illustrates the relationship between pyruvate decarboxylase activity in recombinants and the extent of growth. Cell mass after 24 hours of growth is expressed as the optical density at 550 nm (O.D. 550).
Figure 5:
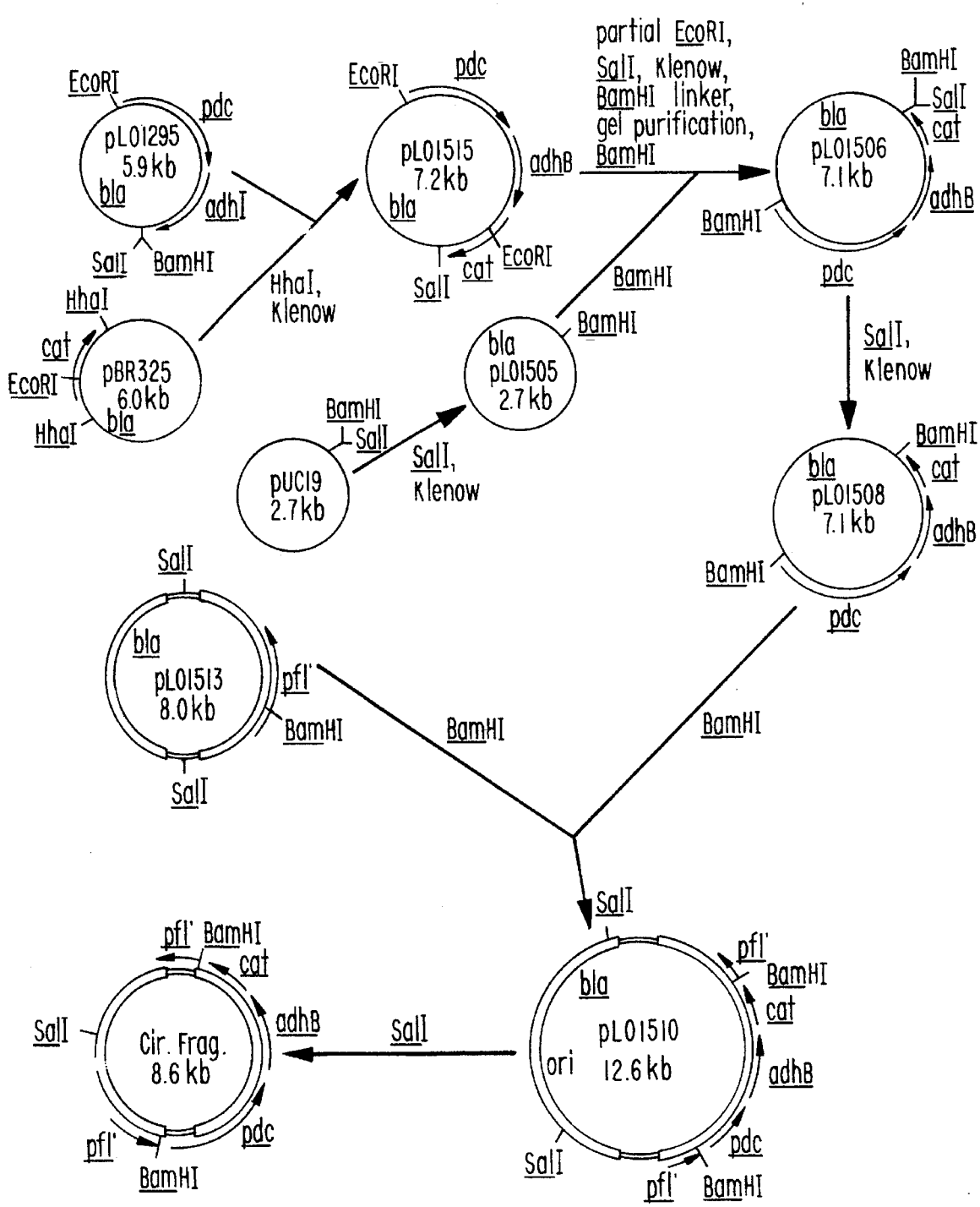
FIG. 5 illustrates the construction of pLOI510.

FIG. 4 shows the relationship between the level of pyruvate decarboxylase activity in cells and the final cell density after 24 hr of growth. Since the synthesis of pyruvate decarboxylase is coupled to that of alcohol dehydrogenase II in these recombinants, this plot represents the effects of the alternative Z. mobilis system for $NAD^+$ regeneration on final cell density. From these data, it is clear that the expression of the Z. mobilis pathway for the production of ethanol increases final cell density under both anaerobic and aerobic conditions. In strain TC4(pLOI308-10), the levels of expression of pyruvate decarboxylase (6.5 IU) and alcohol dehydrogenase II (2.5 IU) were nearly optimal for both anaerobic and aerobic growth. The level of expression of ethanologenic enzymes in strain TC4(pLOI295) appears to be excessive, resulting in diminished cell growth accompanied by partial lysis under aerobic conditions and slightly reduced growth under anaerobic conditions.

The increased growth of strain TC4(pLOI295) under anaerobic conditions with little apparent lysis in contrast to the poor growth and lysis during growth in rapidly shaken flasks suggested that a highly aerobic environment may be damaging to this construction. Lysis in this recombinant was dramatically reduced and the final cell density was increased during growth in shaken flasks when the speed of oscillation was decreased by one-third.

Example 6—Effects Of Ethanologenic Enzymes on the Acidification of Broth During Growth FIG. 3C shows a plot of the changes in the pH of the broth during anaerobic growth. The pH fell rapidly during the first 6 hr of growth of strain TC4 lacking a plasmid but declined more slowly in derivatives containing the ethanologenic enzymes. Acidification during the initial 12 hr was reduced to the greatest extent in strain TC4 containing pLOI295, followed by TC4 containing pLOI308-10, pLOI308-2, and pLOI308-5. Data for strains TC4(pLOI291) and TC4(pLOI292) are not shown but lie below and above those for TC4(pLOI308-5), respectively. Although the recombinants reached a higher final cell density, the pH of the broth from the recombinants grown under both anaerobic and aerobic conditions for 24 hr was less acidic than that of the broth from strain TC4 lacking ethanologenic enzymes (Table 2).

The reduced rate and extent of acidification in recombinants accompanied by increased cell growth suggested that the fall in pH was a major factor limiting growth even under highly aerobic conditions. This hypothesis was supported by an 85% increase in the final cell density of strain TC4 (lacking a plasmid) grown in medium supplemented with a 1/10 volume of 1M sodium phosphate buffer (pH 7.0). Lower levels of buffer addition resulted in intermediate levels of growth.

Example 7—Effects of Ethanologenic Enzymes on Fermentation Products

Table 3 summarizes the analyses of fermentation products made by strain TC4 and the recombinants after 24 hr of growth under aerobic and anaerobic conditions. Under aerobic conditions, acetate was the primary fermentation product that accumulated during the growth of strain TC4 lacking a plasmid in rich medium, with no detectable ethanol. The amount of acetate produced was drastically reduced in strains containing the ethanologenic enzymes from *Z. mobilis,* and ethanol appeared as the major fermentation product. Strain TC4 containing pLOI308-10 produced the most ethanol, followed by TC4 containing pLOI295, pLOI308-2, pLOI292, pLOI308-5, and pLOI291. Under these aerobic conditions, small amounts of lactate were also produced (0.6 to 1.2 mM) by all of these strains. Only strain TC4 containing pLOI308-10 accumulated appreciable amounts of succinate, although this product still represented only 1% of the total fermentation products, with 94% being ethanol.

TABLE 3

Comparison of fermentation products during aerobic and anaerobic growth

| Growth Condition | Plasmid | Fermentation product [mM (SD)] | | | |
|---|---|---|---|---|---|
| | | Succinate | Lactate | Acetate | Ethanol |
| Aerobic | None | 0.2 (0.1) | 0.6 (0.2) | 55 (2) | Tr |
| | pLOI308-2 | Tr | 1.2 (0.3) | 22 (2) | 98 (3) |
| | pLOI308-5 | Tr | 0.9 (0.2) | 43 (3) | 15 (2) |
| | pLOI308-10 | 4.9 (0.5) | 1.0 (0.2) | 17 (2) | 337 (21) |
| | pLOI295 | Tr | 1.1 (0.4) | 13 (1) | 114 (10) |
| | pLOI291 | Tr | 0.6 (0.2) | 34 (3) | 7 (1) |
| | pLOI292 | Tr | 1.3 (0.2) | 30 (1.5) | 24 (1) |
| Anaerobic | None | 0.9 (0.1) | 22 (1) | 7 (0.3) | 0.4 (0.2) |
| | pLOI308-2 | 0.8 (0.1) | 7 (0.5) | 4 (0.3) | 71 (5) |
| | pLOI308-5 | 0.3 (0.1) | 18 (2) | 6 (1) | 16 (2) |
| | pLOI308-10 | 5.0 (0.4) | 10 (1) | 1.2 (0.2) | 482 (23) |
| | pLOI295 | 2.2 (0.20) | 6 (1) | 3 (0.3) | 90 (2) |
| | pLOI291 | 1.0 (0.1) | 15 (0.5) | 7 (0.2) | 4 (0.5) |
| | pLOI292 | 2.3 (0.2) | 9 (0.7) | 7.2 (0.3) | 21 (1) |

Under anaerobic conditions, lactate was the principal fermentation product that accumulated during 24 hr of growth of strain TC4 lacking a plasmid in rich medium containing glucose, with lesser amounts of acetate, succinate, and ethanol being present. Lactate production was dramatically reduced in strains containing the ethanologenic enzymes and was accompanied by the production of substantial quantities of ethanol. Strain TC4(pLOI308-10) produced the largest amount of ethanol, and this product alone represented 97% of the total soluble fermentation products. The trend of ethanol production among the organisms tested was the same as that during aerobic growth. All organisms except TC4(pLOI308-10) actually produced less total ethanol after 24 hr under anaerobic conditions than under aerobic conditions. It is likely that this lower level of accumulated ethanol was caused by the reduction in total cell mass produced under these anaerobic conditions, thus reducing the volumetric rate of ethanol production.

The extent of ethanol production under anaerobic and aerobic conditions (Table 3) was directly related to the level of expression of the *Z. mobilis* ethanologenic genes (Table 1). Ethanol production appeared to be optimal in strain TC4(pLOI308-10), with a pyruvate decarboxylase activity of 6 IU and alcohol dehydrogenase II activity of 2.5 IU.

Derivatives of *E. coli* TC4 containing plasmids which express the ethanologenic enzymes from *Z. mobilis* grew to higher cell densities than did the parent organism lacking a plasmid. The increase in the final cell density, the extent to which ethanol accumulated in the medium, and the reduction in the rate of acidification of the culture broth during growth all correlated with the level of expression of *Z. mobilis* ethanologenic enzymes. Heterologous promoters were used to express the genes in all constructions except pLOI295 (lac) to minimize potential problems associated with transcriptional regulation. The level of expression nearest to optimal for growth and ethanol production was provided by pLOI308-10 (6.5 IU of pyruvate decarboxylase and 2.5 IU of alcohol dehydrogenase II per mg of total cellular protein). This level of expression in *E. coli* is considerably higher than that present in *Z. mobilis* CP4, which contains only the ethanol pathway for the regeneration of $NAD^+$.

The level of expression of ethanologenic enzymes appeared to be excessive in strain TC4(pLOI295) (approximately 17% of the soluble cellular protein). This high level of expression was accompanied by partial cell lysis, slower growth, and a reduction in ethanol production under aerobic conditions. These effects were reduced by slower agitation and by growth under anaerobic conditions. The apparent damage and partial lysis that occurred during highly aerobic growth may have been related to the depletion of NADH by a combination of the high levels of *Z. mobilis* alcohol dehydrogenase II and the native NADH oxidase (coupled to the electron transport system).

The production of ethanol as a major product does not appear to adversely affect the growth rate of *E. coli* TC4. Strains containing derivatives of pLOI308 (ColE1 replicon) expressing the pet operon and producing ethanol grew as rapidly as did the parent organism under aerobic conditions with glucose and reached higher final cell densities than did the parent organism. Strains containing pLOI291 or pLOI292 with the RSF1010 replicon grew more slowly under aerobic conditions. Since these two constructions expressed lower levels of the ethanologenic enzymes and produced less ethanol than did pLOI308-10, the reasons for the slower growth can be attributed to properties of the vector rather than to the expression of the pet operon.

Example 8. Preparation of Additional Strains

Additional *E. coli* strains were tested in order to identify bacteria with superior characteristics for use as an ethanol producing microbe. The following *E. coli* strains were evaluated: ATCC 8677, ATCC 8739, ATCC 9637, ATCC 11303, ATCC 11775, ATCC 14948, ATCC 15244, and ATCC 23227. These were grown in a shaking water bath at 30° C. in Luria broth (Luria, S. E. and M. Delbruck [1943] Genetics 28:491–511) containing tryptone (10 g/liter), yeast extract (5 g/liter), sodium chloride (5 g/liter), and a fermentable sugar. Glucose and lactose were added at concentrations of 100 g/liter and xylose at a concentration of 80 g/liter unless indicated otherwise. Sugars were autoclaved separately (121° C., 15 min), double strength in distilled water. Xylose (Sigma Chemical Co., St. Louis, Mo.) solutions were acidic and were neutralized with sodium hydroxide prior to autoclaving; failure to neutralize resulted in extensive browning and decomposition. Similar fermentation results were obtained with sugars which were autoclaved or filter-sterilized. Survival in broth and on plates of recombinant strains containing genes encoding the enzymes of the ethanol pathway required the presence of a fermentable sugar. Where indicated, tetracycline was added at a final concentration of 10 mg/liter.

Example 9—Environmental Hardiness of Additional Strains

Prior to the introduction of plasmids for ethanol production, the growth of the previously-identified 8 different strains of *E. coli* were compared for environmental hardiness. Strains were tested for their resistance to sodium chloride, sugars, low pH, and ethanol. Concentrations of sodium chloride and sugars in Table 4 include that present in the original medium. The original pH of the medium was 6.8; this was adjusted to lower values with HCl where indicated. Acidified media were sterilized by filtration. Ethanol was added to autoclaved medium after cooling. Sugars were autoclaved separately. Overnight cultures grown in each respective sugar in the absence of test agent were diluted 60-fold into 13×75 mm culture tubes containing 3 ml of test media. Growth was measured as O.D. at 550 nm after 48 hours. An O.D. of 1.0 is equivalent to 0.25 mg/ml of cell protein and 0.33 mg of cell dry weight. In tests of environmental hardiness, a final O.D. below 0.2 reflected less than two doublings and was considered negligible.

Table 4 summarizes these results in medium containing glucose. Similar results were obtained in medium containing lactose or xylose. Strains ATCC 8677, ATCC 8739, and ATCC 11775 were particularly sensitive to inhibition by low concentrations of ethanol. Strains ATCC 9637 and ATCC 11775 were the most resistant to low pH although all strains grew for at least 2 to 4 doublings at pH 4.0 except ATCC 23227. All strains grew at 45° C. with limited growth at higher temperatures; none could be subcultured above 45° C. All strains grew in media containing 20% glucose, 20% lactose, or 12% xylose.

zation (Silhavy, T. J. and J. R. Beckwith [1985] Microbiol. Rev. 49:398–418). Cells were also tested using the Biolog EC plates (Biolog, Inc., Hayward, Calif.) according to the directions of the manufacturer. The Biolog plates were rapid and convenient, detecting NADH production (conversion of a tetrazolium salt to the insoluble formazan) as a measure of substrate utilization. Both methods were in complete agreement for the 13 sugars examined.

All strains tested utilized glucose, fructose, galactose, mannose, arabinose, lactose, glucuronic acid, and galacturonic acid. Strain 11775 did not utilize xylose. Maltose and maltotriose were not used by ATCC 11303 and ATCC 23227. All strains exhibited a weak positive reaction with cellobiose. Only strain ATCC 9637 utilized sucrose. The results of the sugar utilization studies are shown in Table 5.

TABLE 4

Growth of *E. coli* in Luria broth containing 100 g/l glucose under chemical and physical stresses.

| Stress | Growth of *E. coli* strains (ATCC numbers) | | | | | | | |
|---|---|---|---|---|---|---|---|---|
| | 8677 | 8739 | 9637 | 11303 | 11775 | 14948 | 15224 | 23227 |
| NaCl (g/l) | | | | | | | | |
| 50 | + | ++ | ++ | ++ | ++ | ++ | ++ | ++ |
| 60 | 0 | + | ++ | ++ | + | ++ | + | ++ |
| 70 | 0 | 0 | + | + | 0 | + | + | + |
| Ethanol (% by vol.) | | | | | | | | |
| 3.8 | ++ | ++ | ++ | ++ | ++ | ++ | ++ | ++ |
| 5.0 | ++ | ++ | + | + | + | + | + | + |
| 6.3 | 0 | ++ | + | + | + | + | + | 0 |
| 7.5 | 0 | + | + | 0 | 0 | + | 0 | 0 |
| 8.8 | 0 | 0 | 0 | 0 | 0 | 0 | 0 | 0 |
| Acidity | | | | | | | | |
| pH 4.50 | ++ | ++ | ++ | ++ | ++ | ++ | ++ | ++ |
| pH 4.25 | ++ | ++ | ++ | + | ++ | ++ | ++ | + |
| pH 4.00 | + | + | ++ | + | ++ | + | + | 0 |
| pH 3.75 | 0 | 0 | + | 0 | + | 0 | 0 | 0 |
| Temperature (°C.) | | | | | | | | |
| 45 | ++ | ++ | ++ | ++ | + | ++ | ++ | ++ |
| 47 | + | + | + | + | + | + | + | + |
| 49 | 0 | 0 | + | + | 0 | 0 | + | + |

0 = less than two doublings in O.D. 550 nm
+ = two to four doublings
++ = over four doublings Example 10—Sugar Utilization of Additional Strains Sugar utilization was tested in two ways. Strains which developed red colonies on MacConkey agar supplemented with 2% carbohydrate were scored positive for sugar utili-

TABLE 5

Growth of *E. coli* strains harboring pLOI297 and pLOI308-11.

| | | Final O.D. 550 nm of *E. coli* strains (ATCC numbers) | | | | | | | |
|---|---|---|---|---|---|---|---|---|---|
| Sugar | Plasmid | 8677 | 8739 | 9637 | 11303 | 11775 | 14949 | 15224 | 23227 |
| Glucose | none | 4.0 | 3.7 | 6.1 | 6.0 | 4.7 | 5.6 | 7.0 | 6.6 |
| Glucose | pLOI297 | 10.0 | 10.5 | 10.5 | 10.0 | 9.5 | — | 9.5 | 10.2 |
| Glucose | pLOI308-11 | 9.8 | 9.5 | 11.4 | 11.2 | — | 9.3 | 10.9 | 11.4 |
| Lactose | none | 4.3 | 3.8 | 7.5 | 6.0 | 4.5 | 6.1 | 7.0 | 6.4 |
| Lactose | pLOI297 | 13.0 | 6.8 | 11.6 | 10.9 | 7.6 | — | 10.5 | 7.0 |
| Lactose | pLOI308-11 | 10.0 | 10.0 | 11.5 | 11.0 | — | 7.3 | 10.0 | 10.0 |
| Xylose | none | 4.1 | 3.7 | 7.7 | 7.3 | 4.9 | 5.9 | 7.2 | 7.0 |
| Xylose | pLOI297 | 8.1 | 10.6 | 10.8 | 10.6 | 4.7 | — | 11.0 | 11.0 |
| Xylose | pLOI308-11 | 10.0 | 6.8 | 11.4 | 8.5 | — | 11.4 | 10.6 | 12.0 |

Dashed lines indicate no data available.

Example 11—Genetic Alteration of Additional Strains

Two new plasmids were constructed using standard methods (Maniatis, T., E. F. Fritsch, and J. Sambrook [1982] Molecular Cloning: A Laboratory Manual. Cold Spring Harbor Laboratory, Cold Spring Harbor, N.Y.) which contained resistance genes for ampicillin and tetracycline as selectable markers. The ethanol production operon (pet-operon) containing a cryptic *Z. mobilis* promoter, pyruvate decarboxylase, alcohol dehydrogenase and transcriptional terminator was removed as a 5.2 kb EcoRI fragment from pLOI308-10 (Ingram and Conway [1988], supra) and inserted into the EcoRI site of pBR322 to produce pLOI308-11. The plasmid pLOI297 was constructed by inserting the 2.6 kb EcoRI fragment from pCOS2EMBL (Poustka, A., H. R. Rackwitz, A.-M. Firschauf, and H. Lehrach [1984] Proc. Natl. Acad. Sci. USA 81:4129–4133) containing the tetracycline resistance gene in to the SalI site of pLOI295 (Ingram et al. [1987], supra). Cohesive ends were removed by treatment with the Klenow fragment of *E. coli* DNA polymerase (Maniatis et al., supra), prior to the ligation.

Plasmids were introduced into the different strains of *E. coli* by transformation using the calcium chloride procedure of Mandel and Higa (Mandel, M., and A. Higa [1970] J. Mol. Biol. 53:159–162). Selections were made on solid medium containing 2% glucose and tetracycline. Plasmid stability is expressed as the percentage of cells retaining antibiotic markers after 25 generations of growth in the absence of antibiotic selection.

Recombinant strains harboring plasmids with the genes for ethanol production grew as unusually large colonies which became yellow after 24 to 48 hours on solid medium containing a fermentable sugar. In liquid medium, the final cell densities of these recombinants were twice to three times higher than that of the control lacking plasmid. No transformants were obtained after several attempts from ATCC 14948 with pLOI297 or from ATCC 11775 with pLOI308-11. Strain ATCC 11775 did not utilize xylose and recombinants of this strain did not grow to higher densities than the control with xylose as the fermentable sugar, although increased growth was observed with lactose and glucose.

Plasmid stability was examined after growth in medium containing glucose for 25 generations (Table 6. Both plasmids contained the same replicons and were maintained well in all strains except ATCC 8677 and ATCC 8739.

TABLE 6

Stability of pLOI297 and pLOI308-11 after 25 generations of growth with glucose in the absence of antibiotic selection.

| | Cells retaining plasmid | |
|---|---|---|
| ATCC Strain | pLOI297 | pLOI308-11 |
| 8677 | 75 | 85 |
| 8739 | 44 | 47 |
| 9637 | 100 | 90 |
| 11303 | 98 | 98 |
| 11775 | 100 | — |
| 14948 | — | 97 |
| 15224 | 99 | 100 |
| 23227 | 91 | 100 |

Dashed lines indicate no data available.

Example 12—Expression of Pyruvate Decarboxylase Activity in Genetically Altered Strains Pyruvate decarboxylase activity was measured as previously described (Conway et al. [1987], supra; Neale et al. [1987], supra) except that cells were harvested at an O.D. of 4.0, approximately half maximal growth.

The expression of *Z. mobilis* pyruvate decarboxylase activity was examined after growth in the presence of tetracycline (Table 7. With pLOI297, *Z. mobilis* genes are expressed under the control of the *E. coli* lac promoter; pLOI308-11 utilizes a cryptic *Z. mobilis* promoter for expression of pet-operon. Strains ATCC 11303(pLOI297), ATCC 11775(pLOI297) and ATCC 15224(pLOI297) contained the highest levels of activity.

TABLE 7

Expression of *Z. mobilis* pyruvate decarboxylase in *E. coli* strains harboring pLOI297 and pLOI308-11 during growth with glucose.

| | Pyruvate decarboxylase activity[a] | |
|---|---|---|
| ATCC Strain | pLOI297 | pLOI308-11 |
| 8677 | 5.7 | 6.0 |
| 8739 | 0.8 | 1.4 |
| 9637 | 1.1 | 1.4 |
| 11303 | 16.7 | 2.1 |
| 11775 | 17.1 | —[b] |
| 14948 | —[b] | 2.5 |
| 15224 | 16.3 | 1.8 |

TABLE 7-continued

Expression of *Z. mobilis* pyruvate decarboxylase in *E. coli* strains harboring pLOI297 and pLOI308-11 during growth with glucose.

| ATCC Strain | Pyruvate decarboxylase activity[a] | |
|---|---|---|
| | pLOI297 | pLOI308-11 |
| 23227 | 2.3 | 1.7 |

[a] Activity in I.U./mg cell protein.
[b] Dashed lines indicate no data available.

Example 13—Ethanol Production by Genetically Altered Strains

Luria broth was modified for fermentation experiments by the inclusion of potassium phosphate buffer (pH 7.0) at a final concentration of 0.2M. Phosphate buffer, complex medium components, and sugars were autoclaved separately and mixed after cooling. Tetracycline was included at a concentration of 10 mg/liter. Inocula were grown from freshly isolated colonies for 24 hours, washed in the fermentation medium to be tested, and added to an initial O.D. 550 nm of approximately 1.0. Fermentations were carried out at 30° C. or 37° C. in 100 ml volumetric flasks containing 80 ml of broth, fitted with rubber septa and 25 gauge needles to allow gas escape. Fermentation flasks were immersed in a temperature-controlled water bath and stirred by a magnetic stirrer at 100 rpm.

Ethanol concentration was measured by gas chromatography as previously described (Dombek, K. M. and L. O. Ingram [1985] Appl. Environ. Microbiol. 51:197–200) and is expressed as percentage by volume. The conversion efficiency was calculated based upon sugar added, assuming that 100% efficiency results in the production of 12.75 ml of ethanol (10.2 g) per 20 g of glucose or xylose and 13.5 ml of ethanol (10.8 g) per 20 g of lactose.

All genetically engineered strains of *E. coli* produced significant amounts of ethanol from sugars (Table 8). Preliminary experiments with strain ATCC 15244(pLOI297) indicated that higher levels of ethanol were produced in medium containing 0.2M potassium phosphate buffer (pH 7.0). It is anticipated that similar or superior results would be obtained using an automated pH adjustment in place of this buffer. With 15% glucose, higher ethanol levels were produced at 30° C. than at 37° C. after 48 hours. The fermentation of lactose and xylose were examined only at the lower temperature, 30° C. In general, higher levels of ethanol were produced by strains harboring pLOI297 than with pLOI308-11. Strains ATCC 11303(pLOI297), ATCC 11775(pLOI297) and ATCC 15224(pLOI297) produced the highest levels of ethanol after 48 hours from 15% glucose, 5.8% to 6.9% by volume. Most strains were less tolerant of xylose in initial experiments and comparisons of fermentation were carried out using 8% xylose. Strains ATCC 9637(pLOI297), ATCC 11303(pLOI297), and ATCC 15224(pLOI297) produced the highest levels of ethanol (4.8% to 5.2%) from 8% xylose after 72 hours. All strains grew well in 15% lactose. Strains ATCC 11303(pLOI297) and ATCC 15224(pLOI297) produced the highest levels of ethanol from lactose after 48 hours, 6.1% and 5.6%, respectively.

TABLE 8

Ethanol produced in batch fermentation from glucose (48 hours), xylose (72 hours), and lactose (48 hours) by *E. coli* strains harboring pLOI297 and pLOI308-11.

| Carbohydrate | Plasmid | Ethanol (%, v/v) produced by *E. coli* strains (ATCC numbers) | | | | | | | |
|---|---|---|---|---|---|---|---|---|---|
| | | 8677 | 8739 | 9637 | 11303 | 11775 | 14948 | 15224 | 23227 |
| 15% glucose | pLOI297[a] | 2.4 | 4.7 | 4.2 | 4.3 | 4.8 | — | 4.8 | 0.9 |
| 15% glucose | pLOI308-11[a] | 3.6 | 1.4 | 2.1 | 1.3 | — | 3.4 | 2.8 | 1.3 |
| 15% glucose | pLOI297[b] | 3.2 | 4.7 | 4.1 | 5.8 | 6.9 | — | 6.1 | 3.1 |
| 15% glucose | pLOI308-11[b] | 5.8 | 5.0 | 3.5 | 1.5 | — | 3.8 | 3.0 | 3.2 |
| 15% lactose | pLOI297[b] | 2.3 | 4.4 | 5.3 | 6.1 | 4.5 | — | 5.6 | 3.7 |
| 15% lactose | pLOI309-11[b] | 2.3 | 2.1 | 3.4 | 0.9 | — | 2.9 | 2.7 | 3.0 |
| 8% xylose | pLOI297[b] | 0.9 | 4.1 | 4.8 | 5.2 | — | — | 4.8 | 1.2 |
| 8% xylose | pLOI308-11[b] | 2.0 | 2.8 | 2.8 | 1.2 | — | 2.0 | 3.5 | 1.0 |

Dashed lines indicate no data available.
[a] Incubated at 37° C.
[b] Inculated at 30° C.

Based upon these comparative studies, strains ATCC 11303(pLOI297) and ATCC 15224(pLOI297) appeared to be the best constructs for ethanol production. The time course of growth and ethanol production were examined with both strains in 12% glucose, 12% lactose, and 8% xylose (FIG. 1). Cell mass increased approximately 10-fold, reaching a final density of 3.6 g dry weight/liter. With xylose, cell mass increased at half the rate observed with glucose or lactose. Ethanol production and growth were approximately linear for the three sugars until the concentration of ethanol reached 5%.

To compute the conversion efficiency of sugar to ethanol, final ethanol concentrations after 120 hours were averaged from three sets of experiments (Table 6). The final concentration of ethanol in cultures grown with 12% glucose was 7.2% (by vol.), representing 94% of theoretical yield from glucose. With 12% lactose, the final ethanol concentration was 6.5%, 80% of the theoretical yield from lactose. With 8% xylose, we consistently obtained yields of 100% and higher. These high yields during slower growth with xylose may reflect the conversion of pyruvate from the catabolism of complex nutrients into ethanol, in addition to pyruvate from glucose.

The rate of ethanol production was computed from the graphs in FIG. 1 and are summarized in Table 9. Volumetric productivity of ethanol ranged from 1.4 g/liter per hour for glucose to 0.64 g/liter per hour for xylose. Specific productivity of ethanol was highest during the initial growth period for each of the three sugars. The highest productivity was obtained with glucose, 2.1 g ethanol/g cell dry weight per hour. The highest yield of ethanol per g of sugar was obtained with xylose, exceeding the maximal theoretical yield for sugar alone.

TABLE 9

Averaged kinetic parameters for ethanol production by ATCC 11303(pLOI297) and ATCC 15224(pLOI297).

| Sugar | Volumetric[a] Productivity | Specific[b] Productivity | Yield[c] | Efficiency[d] | Ethanol[e] |
|---|---|---|---|---|---|
| 12% glucose | 1.4 | 2.1 | 0.48 | 95% | 58 |
| 12% lactose | 1.3 | 2.0 | 0.43 | 80% | 52 |
| 8% xylose | 0.6 | 1.3 | 0.52 | 102% | 42 |

[a] g ethanol/liter per hour
[b] g ethanol/g cell dry weight per hour
[c] g ethanol/g sugar
[d] ethanol produced/theoretical maximum from sugar substrate × 100
[e] final ethanol concentration in g/liter Experiments were conducted with ATCC 11303(pLOI297) to examine ethanol production from arabinose, galactose, and mannose. Ethanol concentrations of 3% to 4% were obtained after 48 hours at 30° C. but were not investigated further. These sugars were metabolized by pathways similar to those for glucose and xylose and would be expected to produce analogous yields (Lin, E. C. C. [1987] "Dissimilatory pathways for sugars, polyols, and carboxylates," In F. C. Neidhardt, J. L. Ingraham, K. B. Low, B. Magasanik, and M. Schaechter [eds], *Escherichia coli* and *Salmonella typhimurium*, Vol. 1, pp. 244–284. American Society for Microbiology, Washington, D.C.).

Example 14—Ethanol Production from Hosts Other than *E. coli*

The great similarity in pathways between various organisms makes it predictable that a variety of hosts can be transformed with genes which then confer upon the transformed host the ability to produce ethanol as a fermentation product. When hosts are transformed with the adh and pdc genes, as described herein, it is fully predictable that appropriate expression vectors can be utilized to achieve expression. Once expression is achieved, the production of ethanol is highly predictable because of the uniformity of this pathway across various potential hosts.

Example 15—Ethanol Production in Transformed Klebsiella

The Klebsiella strain used in this study was previously designated as *Klebsiella pneumoniae* strain M5A1 (Mahl, M. C., P. W. Wilson, M. A. Fife, W. H. Ewing [1965] J. Bacteriol. 89:1482–1487). This strain, a dinitrogen-fixing organism, was originally identified as *Aerobacter aerogenes* but renamed based upon antigenic properties. Since new taxonomic criteria for *Klebsiella pneumoniae* were defined in the 8th edition of Bergy's Manual, the speciation of this new strain was investigated further. Strain M5A1 grew at 10 C in glucose minimal medium but failed to produce gas from lactose at 44.5 C. This strain was indole positive and utilized both m-hydroxybenzoate and gentisate as sole sources of carbon for growth at both 30 C and 37 C. Based upon these tests, M5A1 was designated *K. oxytoca*. Strains were subcultured on Luria agar plates lacking added sugar unless they harbored plasmids encoding *Z. mobilis* genes. Recombinants containing adhB and pdc require a fermentable carbohydrate for survival and were maintained on plates containing 2% glucose or xylose. Antibiotic concentrations were as follows: ampicillin, 50 μg/ml; chloramphenicol, 40 μg/ml; and tetracycline, 12.5 μg/ml. Expression of *Z. mobilis* adhII in recombinants was screened using aldehyde indicator plates. *Escherichia coli* strain TC4 was used as the host for all plasmid constructions.

Since M5A1 is relatively resistant to penicillin and its derivatives, we have constructed *E. coli* shuttle vectors carrying the cat (Cm$^r$) or tet (Tc$^r$) genes. A tet gene was added to pLOI276 containing *Z. mobilis* pdc by inserting a 2.6-kilobase pair EcoRI fragment from pcos2EMBL (Poustka, A., H. R. Rackwitz, A. -M. Frischauf, B. Hohn, H. Lehrach [1984] Proc. Natl. Acad. Sci. USA 81:4129–4133) into the SalI site of pLOI276. Cohesive ends were removed by treatment with the Klenow fragment of *E. coli* DNA polymerase before ligation. The resulting construct was confirmed by restriction analysis and designated pLOI560.

Preliminary studies indicated that *E. coli* B (ATCC 11303) harbored cryptic low copy number plasmids. A new and useful vector was constructed in vivo by integrating the *Z. mobilis* pdc and adhB along with cat into these plasmids. This was done by isolating a 4.6-kilobase pair, promoterless PstI fragment containing pdc, adhB, and cat from pLOI510. No replication functions are present on this fragment. After circularizing by self-ligation, these fragments were transformed into *E. coli* B with selection for Cm$^r$ on Luria agar plates containing 2% glucose. Transformants were tested on aldehyde indicator plates and dark red clones were selected for high level expression of the adhB gene. Plasmid preparations from these strains were tested for their ability to transfer antibiotic resistance and *Z. mobilis* genes into *E. coli* TC4 by transformation. All recombinants were sensitive to ampicillin, indicating a lack of the pUC18 fragment containing bla and the colE1 replicon. One of these, pLOI555 (8.4 kilobase pair), produced the most intensely red colonies on aldehyde indicator plates, conferred excellent ethanol production ability to *E. coli*, and appeared to be present in low copy number based upon yields from small scale plasmid isolations. This plasmid, as well as pLOI297 and pLOI560, were used to transform *K. oxytoca* M5A1 with selection for Cm$^r$.

Three plasmid constructs containing the *Z. mobilis* gene encoding PDC were transformed into M5A1 (Table 10). The levels of PDC were 8-fold higher in the two pUC-based constructs (pLOI297 and pLOI560) than with pLOI555. Assuming a maximum specific activity for pure PDC of 100 U, this enzyme comprises over 25% of the cytoplasmic protein in M5A1(pLOI297) and M5A1(pLOI560) and 3.6% in M5A1 (pLOI555).

TABLE 10

Plasmid stability and pdc expression in recombinant strains of M5A1

| Plasmid | PDC activity after 24 hours (U/mg protein) | Percentage retaining traits[a,b] (number of generations) | |
|---|---|---|---|
| pLOI555 | 3.6 | 100 (38.5) | 98 (68.5) |
| pLOI297 | 28 | 52 (38.6) | 10 (68.6) |
| pLOI560 | 27 | 97 (32.9) | 0 (62.9) |

[a] Cells were sampled at two times during cultivation.
[b] Both the aldehyde trait and antibiotic resistance were lost concurrently.

The expression of *Z. mobilis* genes in M5A1 was further confirmed in SDS-PAGE gels. Bands which contain PDC and ADHII were easily identified by comparison with the native strain. The band containing PDC is much larger in pUC-based recombinants than in M5A1(pLOI555), consistent with measurements of enzymatic activity. Although ADHII is less abundant than PDC, relative expression of this Z. mobilis gene is also higher in M5A1(pLOI297) than in M5A1(pLOI555). No band corresponding to ADHII was evident in M5A1(pLOI560) which contains only the Z. mobilis pdc gene.

The copy number of pLOI555 was estimated to be less than 1/10 that of the two other constructs based on yields in small scale plasmid preparations. Although this estimate is only approximate, it is clear that the high levels of PDC present in the pUC-based constructs are due in part to higher copy number.

Cells harboring pLOI555, pLOI297, or pLOI560 were serially transferred in Luria broth containing 10% glucose without antibiotics for more than 60 generations at 30 C. Appropriate dilutions of cultures were plated on Luria agar containing 2% glucose without antibiotics. Colonies were tested on aldehyde indicator plates for the retention of the ethanol production genes from Z. mobilis and for resistance to appropriate antibiotics.

Excessive instability of Z. mobilis genes in pBR322-based vectors was reported previously for Klebsiella planticola (Tolan, J. S., R. K. Finn [1987] Appl. Environ. Microbiol. 53:2039–2044) and would not be acceptable for industrial processes. Recombinants harboring pLOI555 were very stable with 98% of the population retaining both the antibiotic resistance gene and the genes from Z. mobilis. Although only adhB expression is detected by aldehyde indicator plates, these recombinants also retained the large colony phenotype indicative of expression of both pdc and adhB.

Fermentations were carried out in Luria broth containing 10% (w/v) glucose or xylose at 30 C, pH 6.0, 100 rpm agitation. Inocula were grown overnight at 30 C from isolated colonies in unshaken flasks. Fermentations were inoculated to an initial O.D.$_{550nm}$ of 1.0 (330 mg dry weight of cells/liter). A Bausch and Lomb Spectronic 70 spectrophotometer was used to monitor growth.

Ethanol concentrations were determined by gas-liquid chromatography. Conversion efficiencies were corrected for volume changes caused by the addition of base and assumed that all sugars had been metabolized. The maximum theoretical yield of ethanol from xylose and glucose was calculated to be 0.51 g ethanol per gram of sugar with the balance as carbon dioxide. Volumetric productivities were estimated from the most active periods and represent maximum values. All fermentation data in tables and in figures are averages from two or more batch fermentations.

Table 11 shows the effects of Z. mobilis PDC+ADHII on ethanol production from glucose and xylose respectively to the native strain M5A1.M5A1(pLOI555) was clearly the best construct for ethanol production with maximum volumetric productivities of 2.1 g/liter per hour for both glucose and xylose. With either sugar, this recombinant produced approximately 37 g ethanol/liter after 30 hours. Fermentation of these sugars was essentially completed after 48 hours with 45 g ethanol/liter.

TABLE 11

| | | | | Ethanol production from glucose and xylose by reccombinant strains of M5A1[a] | | | | | |
|---|---|---|---|---|---|---|---|---|---|
| | | Base (mmol/g | Time[d] | Ethanol yield | | Theoretical | VP (g/liter | 30-h ethanol | Cell yield |
| Plasmid | Genes[b] | of sugar)[c] | (hr) | g/l | g/g of sugar | yield (%) | per hour)[e] | (g/liter) | (g/g sugar) |
| Glucose | | | | | | | | | |
| no plasmid | | 1.0 | 48 | 15 | 0.16 | 31 | 1.1 | 15 | 0.044 |
| pLOI560 | pdc | 0.8 | 72 | 44 | 0.46 | 90 | 1.1 | 15 | 0.018 |
| pLOI297 | pdc adhB | 0.7 | 72 | 50 | 0.52 | 102 | 1.3 | 24 | 0.020 |
| pLOI555 | pdc adhB | 1.0 | 48 | 48 | 0.50 | 98 | 2.1 | 43 | 0.040 |
| Xylose | | | | | | | | | |
| no plasmid | | 1.9 | 96 | 14 | 0.16 | 31 | 0.5 | 7 | 0.044 |
| pLOI560 | pdc | 0.7 | 96 | 37 | 0.38 | 75 | 1.2 | 5 | 0.025 |
| pLOI297 | pdc adhB | 0.9 | 96 | 37 | 0.39 | 76 | 1.0 | 12 | 0.024 |
| pLOI555 | pdc adhB | 1.1 | 48 | 46 | 0.48 | 94 | 2.0 | 37 | 0.054 |

[a]Calculations are based on total sugar added initially.
[b]Genes indicated are from Z. mobilis.
[c]Amount of base consumed to maintain a pH of 6.0 during fermentation.
[d]Time of maximum ethanol concentration.
[e]VP, maximum volumetric productivity during batch fermentation.

As with ethanol production, the growth of M5A1(pLOI555) was clearly superior. Growth of this recombinant was almost equivalent to that of the parental strain. However, unlike the parental strain, cell density progressively declined after reaching a maximum at 15 hours. This decline may reflect a reduction in refractility as ethanol accumulated since lysis was not evident. Without the addition of base to control pH, recombinants containing pdc+adhB grew to over twice the density of the parent organism due to a reduced rate of acid production (higher proportion of neutral fermentation products) as observed previously with E. coli.

The maximal volumetric productivities (2.1 g ethanol/liter per hour) are almost double that of E. coli recombinants while maintaining similarly high efficiencies and final ethanol concentrations. Unlike E. coli, M5A1(pLOI555) ferments xylose and glucose at equivalent rates. Plasmid pLOI555 was stably maintained in M5A1 in the absence of antibiotic selection. Since the range of substrates for M5A1 is equivalent to that of E. coli, M5A1 recombinants offer a distinct and unexpected advantage for ethanol production.

Example 16—Fermentation of Cellobiose to Ethanol by ethanologenic recombinants of Erwinia and of Klebsiella This example illustrates the fermentation of an oligosaccharide, cellobiose, using ethanologenic recombinants of Erwinia and Klebsiella.

The Erwinia used in this example was a typical strain of *Erwinia carotovora*. The Erwinia was transformed using the plasmid pLOI555 described above in Example 15. The plasmid pLOI555 was inserted into the Erwinia using a Biorad Electroporation unit and following the procedures of Ito et al. [1988] Ag. and Biol. Chem. 52(1): 293–4 (voltage= 2.0 kV, capacitance= 25 µF, and resistance= 100 ohms). High numbers of transformants, i.e., more than 100,000 per µg of plasmid DNA, were recovered.

The Klebsiella used in this example was *Klebsiella oxytoca* M5A1 strain P2, which was obtained as described below in Example 18.

Figure 6:
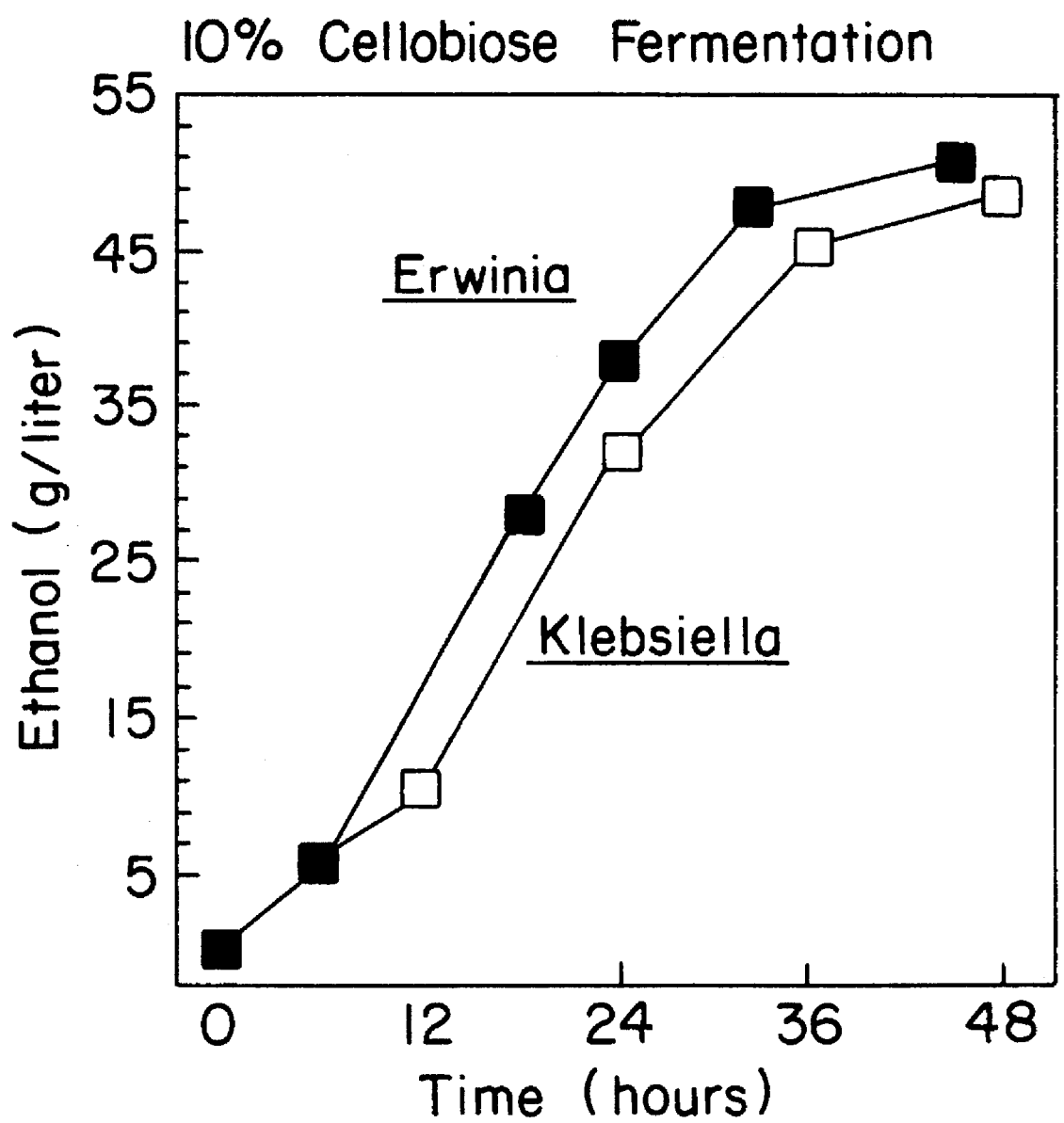
FIG. 6 illustrates the concentration of ethanol produced from fermentation of cellobiose by ethanologenic recombinants of Erwinia and of Klebsiella.

The fermentations were conducted as in Example 15, using 10% cellobiose in Luria broth (pH 6, 30° C.) and 100 rpm agitation. The concentration of ethanol produced by the Erwinia and *Klebsiella oxytoca* was 1.113 molar and 1.065 molar, respectively. The results are provided in FIG. 6 in g/L of ethanol produced. Symbols: ■, Erwinia; □, Klebsiella.

Example 17—Fermentation of Polymeric Feedstocks to Ethanol by a Single, Genetically Engineered Microorganism Summary of Example: This example illustrates a two-stage process for fermenting polymeric feedstocks to ethanol by a single microorganism which has been genetically engineered to produce ethanol as a primary fermentation product and to produce xylanase intracellularly. Specifically, the truncated xylanase gene (xynZ) from the thermophilic bacterium, *C. thermocellum*, was fused with the N-terminus of lacZ to eliminate secretory signals. This hybrid gene was expressed at high levels in the *E. coli* KO11 and *K. oxytoca* M5A1 (pLOI555) discussed above. Large amounts of xylanase accumulated as an intracellular product during ethanol production. Cells containing xylanase were harvested at the end of fermentation and added to a xylan solution at elevated temperature, thereby releasing xylanase for saccharification. After cooling, the hydrolysate was fermented to ethanol with the same organism thereby replenishing the supply of xylanase for a subsequent saccharification.

Organism and growth conditions: Bacterial strains and plasmids used in this example are listed in Table 12.

TABLE 12

| Bacteria strains and plasmids used | | |
|---|---|---|
| Bacteria/plasmid | Characteristics | Source or reference |
| *E. coli* DH5α | lacZM15,recA | Bethesda Rsrch Lab |
| *E. coli* KO11 | frd, Cm$^r$, Ipet[a] | Ohta et al.[c] |
| *K. oxytoca* M5A1(pLOI555) | Cm$^r$,pet[b] | Example 15, supra |
| pCT1202 | Ap$^r$,xynZ$^+$ | Grepinet et al.[d] |
| pLOI1001 | Ap$^r$,xylB$^+$ | Utt et al.[e] |
| pLOI2000 | Ap$^r$,xylB$^+$ | this example |
| pLOI2001 | Ap$^r$,lacZ::xynZ$^+$ | this example |
| pLOI2002 | Ap$^r$,lacZ::xynZ$^+$ | this example |
| pLOI2003 | Ap$^r$,lacZ::xynZ$^+$,xylB$^+$ | this example |

[a]Ipet refers to the integration of *Z. mobilis* pdc and adhB genes into the chromosome.
[b]pet refers to the presence of *Z. mobilis* pdc and adhB genes on plasmid pLOI555.
[c]Ohta et al. [1991] Appl. Environ. Microbiol. 57:893–900.

TABLE 12-continued

| Bacteria strains and plasmids used | | |
|---|---|---|
| Bacteria/plasmid | Characteristics | Source or reference |

[d]Grepinet et al. [1988] J. Bacteriol. 170:4582–4588.
[e]Utt et al. [1991] Appl. Environ. Microbiol. 57:1227–1234.

Strains were grown in Luria broth supplemented with 50 g xylose/liter. Transformants of *E. coli* were selected on Luria agar plates containing 50 mg ampicillin/liter or 40 mg chloramphenicol/liter. Transformants of *K. oxytoca* M5A1 were selected on Luria agar containing 1000 mg ampicillin/liter or 40 mg chloramphenicol/liter.

Recombinant clones were screened for xylanase activity by using microtitre plates which contained 4-methylumbelliferyl-β-D-cellobiopyranoside (100 mg/liter) (Millet [1985] FEMS Microbiol. Lett. 29: 145–149). Similarly, expression of the *Butyrivibrio fibrisolvens* xylB gene encoding both xylosidase and arabinosidase activities was screened by incorporating 4-methylumbelliferyl-α-L-arabinofuranoside (20 mg/liter) into solid medium (Utt et al. [1991] Appl. Environ. Microbiol. 57: 1227–1234). Hydrolysis of these substrates by positive clones produced a fluorescent product (umbelliferone) which was readily detected under 340 nm ultra violet light.

Genetic procedures and recombinant techniques: Plasmid preparation, digestion with restriction enzymes, ligation, transformation, and gel electrophoresis were carried out using standard procedures. *E. coli* strain DH5α was used as the host for all plasmid constructions. Polymerase chain reactions were performed with the TempCycler Model 50 (Coy Laboratory Product Inc., Ann Arbor, Mich.) and a GeneAmp kit (Perkin Elmer Cetus, Norwalk, Conn.) containing Taq polymerase. Amplification reactions contained 2 mM each dNTP, 100 pmol each primer, 20 ng template, and 2.5 U Taq polymerase in 100 µl total volumes. Products were isolated after 30 cycles of amplification (1 minute at 94° C., 2 minutes at 47° C. and 1 minute at 72° C.; final extension for 3 minutes at 72° C.).

Determination of enzymatic activities: Xylanase, xylopyranosidase, and arabinofuranosidase activities were measured in recombinants which had been grown overnight at 30° C. Cells were harvested by centrifuguation (7000 × g, 10 minutes) and washed twice with phosphocitrate buffer (50 mM potassium phosphate and 12.5 mM citric acid, pH 6.3) for the determination of xylanase activity or with phosphate buffer (5 mM sodium phosphate buffer containing 10 mM 2-mercaptoethanol, pH 6.8) for the measurement of xylosidase and arabinosidase activities. Cells were disrupted by two passages through a French pressure cell at 20,000 psi. The resulting lysate was centrifuged (13,000× g for 30 minutes, 4° C.) to remove cell debris.

Xylosidase and arabinofuranosidase activities were assayed as described previously (Utt, supra.). Xylanase was measured by the same procedure but using p-nitro-β-D-cellobioside as the substrate. Xylanase activity was also estimated by measuring the release of reducing sugars (Bergmeyer (ed) [1983] Methods of enzymatic analysis, Vol. II, 3rd edition, p 151–2, Verlag Chemie, Weinheim, Germany) from the hydrolysis of birchwood xylan (Sigma Chemical Company, St. Louis, Mo.). All activities are reported as millimicromoles of product liberated per minute. Protein concentration was determined by the method of Bradford (Bradford [1976] Anal. Biochem. 72: 248–254).

Separation of xylooligosaccharides by thin layer chromatography: A mixture of xylooligosaccharides was prepared by the partial hydrolysis of 0.5% birchwood xylan with trifluoracetic acid (Domer [1988] Meth. Enzymol. 160: 176–180). The solution was concentrated 10-fold under vacuum at room temperature and 1 μliter samples used as a standard. Xylooligosaccharides were separated at room temperature by single development on unactivated Whatman silica gel 150A plates (Whatman Inc., Clifton, N.J.) using a solvent composed of acetone, ethylacetate, and acetic acid (2:1:1, respectively). After drying, oligosaccharides were visualized with naphthylethylenediamine reagent as described by Bounias (Bounias [1980] Anal. Biochem. 106:291–295).

Fermentation experiments: Inocula for fermentations were prepared from freshly isolated colonies by overnight growth in unshaken flasks (30° C.). Fermentations were inoculated to an initial O.D. at 550 nm of either 0.1 or 0.3 and incubated at 30° C. in stirred, pH-stats (350 ml working volume, pH 6.0). (Beall et al. [1991] Biotechnol. Bioengin. 38: 296–303.; Ohta et al. [1991] Appl. Environ. Microbiol. 57: 893–900; and Ohta et al. [1991] Appl. Environ. Microbiol. 57:2810–2815.) Chloramphenicol or chloramphenicol and ampicillin were included in fermentation broths.

Xylan was fermented by a two stage process in which xylan degradation was carried out at elevated temperature followed by fermentation at 30° C. For the degradation of xylan, cells from 350-ml fermentations were harvested by centrifugation (7,000× g, 10 minutes) after 48 hours, resuspended in an equal volume of fresh Luria broth containing 4% xylan (pH 6.0), and incubated at 60° C. for 65 hours. After cooling to 30° C., hydrolysates were inoculated with recombinant organisms to provide an initial O.D. of 0.3 at 550 nm.

Samples were removed at various times to monitor xylooligosaccharides (thin layer chromatography), cell growth (O.D. at 550 nm), and ethanol. Ethanol was measured by gas liquid chromatography (Dombek et al. [1985] Appl. Environ. Microbiol. 51:197–200).

Construction of recombinant plasmids for the hydrolysis of xylan: At least two activities are required for the hydrolysis of unsubstituted xylan, i.e., an endolytic xylanase and xylosidase. Three plasmids were constructed for use in xylan fermentations in which the xynZ (xylanase) gene from the thermophile, Clostridium thermocellum (Grepinet et al. [1988] J. Bacteriol. 170: 4582–4588), and the xylB (xylosidase and arabinosidase) gene from Butyrivibrio fibrisolvens (Utt, supra.) were expressed singly and in combination as an operon (FIGS. 7A, 7B and 7C).

Figures 7A, 7B, 7C:
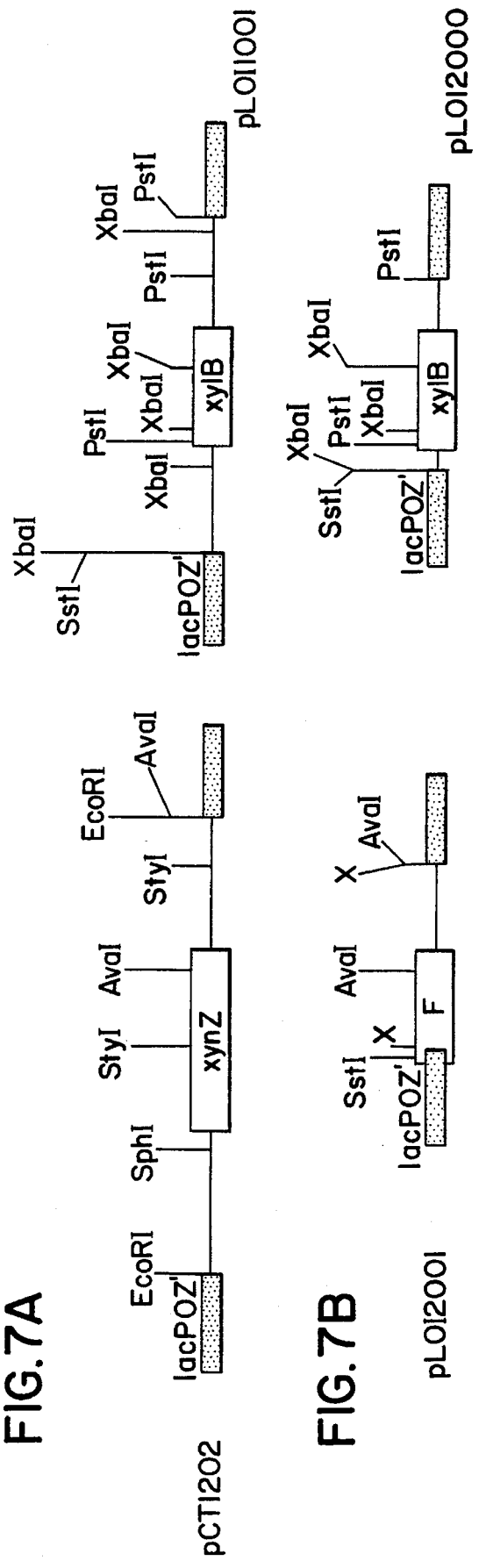
FIGS. 7A, 7B and 7C illustrate the construction of recombinant plasmids containing xynZ and xylB.

FIGS. 7A, 7B, and 7C illustrate the construction of recombinant plasmids containing xynZ and xylB. Coding regions are boxed. C. thermocellum and B. fibrisolvens DNA are represented by thin lines. The thick line denotes vector DNA. Sites of blunt-ended ligation are marked by an "X." An "F" labels the coding region for the in-frame lacZ::xynZ fusion.

The xylB gene was subcloned into the XbaI to PstI region of the polylinker in pUC18 by inserting two fragments from pLOI1001, a 0.3 kilobase-pair (kbp) XbaI to PstI fragment containing the amino terminus with ribosomal-binding site and a 2.4 kbp PstI fragment containing the remainder of the coding region and translational terminator. The resulting plasmid, pLOI2000, expressed the xylB gene from the lac promoter.

Previous studies by Grepinet et al., supra, have shown that xylanase expression was elevated in lacZ fusions in which a large segment encoding the secretion signal sequence and amino terminus of the processed xylanase had been deleted. A very similar lacZ::xynZ fusion was constructed by blunt-ended ligation of the Klenow-treated 2.4 kbp StyI fragment from pCT1202 containing the amino-truncated xynZ gene into the Klenow-treated PstI site of pUC18. Both reading frames were aligned in the resulting plasmid, pLOI2001.

It was necessary to remove the putative transcriptional terminator 30 bp downstream from the coding region of lacZ::zynZ and add a new SstI site to the 3'-end of the fusion gene prior to constructing a plasmid from which genes encoding both xylanase and xylosidase were expressed. These modifications were made by using polymerase chain reaction. Plasmid pLOI2001 was used as the template with 5'-GAATTCGAGCTCGGTAC-3' as a primer for the 5'-end and 5'-GGGAGCTCCGGCATCATTATCTG-3' as a primer for the 3'-end (includes a new SstI site). After SstI digestion, this fragment was inserted into the SstI polylinker sites of pUC18 and pLOI2000 to construct pLOI2001 and pLOI2003, respectively.

Expression of enzymes involved in xylan degradation: The expression of xylanase, xylosidase, and arabinosidase activities were initially examined in stationary phase cells of the host organism used for constructions, strain DH5α (Table 13). Xylanase (xynZ) activity was reduced by 60% in clones harboring pLOI2003 which contains xylB downstream as compared to pLOI2001 which contains xynZ alone. However, xylosidase and arabinosidase (xylB) activities were similar in clones harboring pLOI2000 containing xylB alone and pLOI2003 containing an upstream xynZ gene.

TABLE 13

Specific activities of recombinant enzymes for xylan degradation

| Strain and plasmid | Specific activity (mU/mg) | | | |
|---|---|---|---|---|
| | xylosidase | arabinosidase | xylanase[a] | xylanase[b] |
| E. coli DH5α | 0 | 0 | 0 | 0 |
| pLOI2000 | 1.2 | 2.2 | 0 | 0 |
| pLOI2001 | 0 | 0 | 1.4 | 124 |
| pLOI2003 | 1.5 | 2.5 | 0.5 | 48 |
| E. coli KO11 | 0 | 0 | 0 | 0 |
| pLOI2001 | 0 | 0 | 0.4 | 38 |
| pLOI2003 | 1.3 | 2.4 | 0.3 | 25 |
| pLOI2003[c] | 1.1 | 1.9 | 0.3 | 47 |
| pLOI2003[c,d] | nd | nd | 0.8 | 93 |
| K. oxytoca M5A1 (pLOI555) & pLOI2001 | 49 | 0 | 0.4 | 39 |
| pLOI2003 | 56 | 2.6 | 0.2 | 24 |
| pLOI2001[c] | 30 | 0 | 0.7 | 0 |
| pLOI2001[c,d] | nd | nd | 1.8 | 144 |
| pLOI2003[c] | 38 | 2.9 | 0.4 | 58 |
| pLOI2003[c,d] | nd | nd | 0.8 | 144 |

Unless indicated otherwise: cells were grown in shake flasks containing Luria broth with 5% xylose and harvested after 20 hours (stationary phase); xylosidase and arabinosidase activities were determined at 30° C.; and xylanase activities were measured at 45° C.
[a]Xylanase activities were measured using p-nitrophenyl-β-D-cellobioside as a substrate.
[b]Xylanase activities were measured using 0.5% birchwood xylan as a substrate.
[c]Cells were harvested from pH-stats (8% xylose in Luria broth, pH 6.0) at the end of fermentation.
[d]Xylanase activities were determined at 60° C.

The plasmids pLOI2001 and pLOI2003 were transformed into the ethanologenic strain of E. coli KO11, in which the genes for ethanol production are integrated into the chromosome. Expression was compared in stationary phase cells from shake flasks and in cells from a pH-stat at the end of fermentation (Table 13). Xylosidase, arabinosidase, and xylanase activities were equivalent to those observed with DH5α. Again, xylanase activity was reduced in pLOI2003 in which xylB was present downstream.

Expression was also examined in *K. oxytoca* strain M5A1 harboring pLOI555 containing genes from the *Z. mobilis* ethanol pathway. Although the type of replicon present in pLOI555 is unknown, it appeared quite stable in the presence of a second plasmid constructed from pUC18. Expression of arabinosidase and xylosidase activities were roughly equivalent to that observed in *E. coli*. An abundant native xylosidase was discovered in M5A1. Xylosidase activities were somewhat higher in cells from shake flasks as compared to cells from pH-stats while xylanase activities followed the opposite trend.

Under the assay conditions used, arabinosidase activity was 1.5 to 1.7 times higher than xylosidase activity confirming previous reports (Utt et al., supra). Xylanase activity measured at 47° C. was approximately half that measured 60° C., the optimal temperature for the native enzyme (Grepinet et al., supra). Based on the data presented, specific activities computed from reducing sugar assays for the xylanase fusion are approximately 100-fold higher than estimates based on the hydrolysis of p-nitrophenyl-β-D-cellobioside indicating a strong preference for native substrate.

Hydrolysis of xylan at elevated temperature by recombinant clones: Strain KO11(pLOI2003) was grown in a pH-stat containing 8% xylose and tested as a source of enzyme for xylan hydrolysis. Cells were resuspended in an equal volume of fresh Luria broth containing 4% xylan and incubated at 45° C., the maximal temperature at which *B. fibrisolvens* xylosidase is stable, and 60° C. and the optimal temperature for *C. thermocellum* xylanase. Although xylanase and xylosidase were produced as intracellular products, initial experiments indicated that these enzymes were readily released into the medium by incubation at 45° and 60° C. Samples were removed at various times and digestion products analyzed by thin layer chromatography (FIGS. 8A and 8B).

Figure 8B:
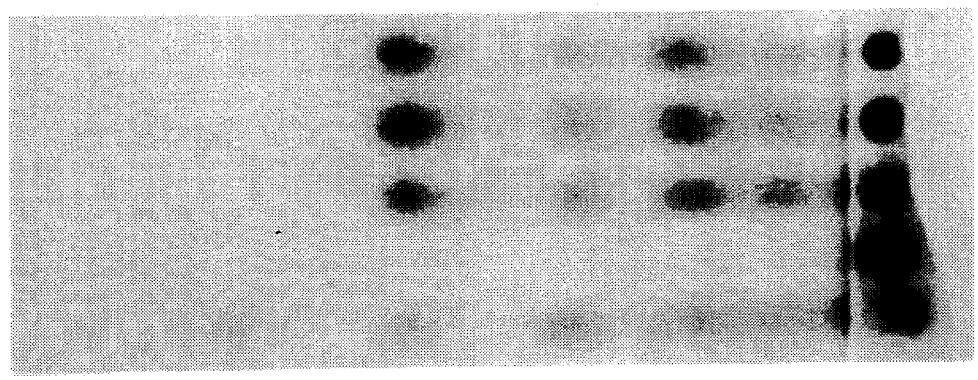
FIGS. 8A and 8B comprise thin layer chromatographic analysis of xylan hydrolysis using *E. coli* strain KO11(pLOI2003) incubated at 45° C.
Figure 8A:
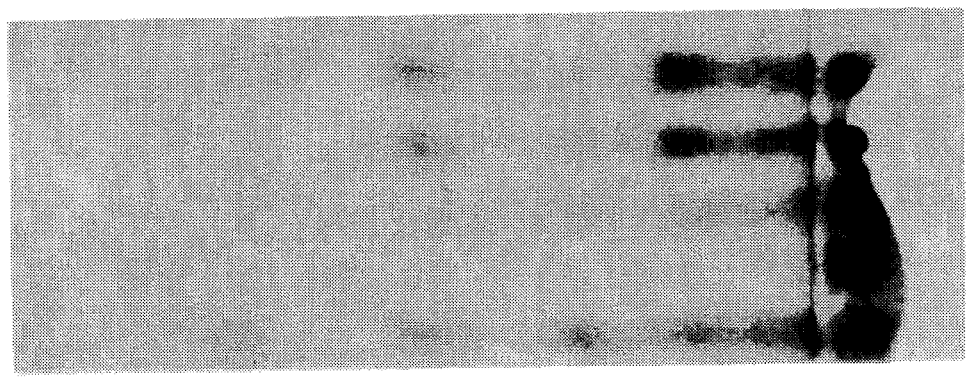

FIGS. 8A and 8B show thin layer chromatographic analysis of xylan hydrolysis using *E. coli* strain KO11(pLOI2003) incubated at 45° C. (FIG. 8A) or 60° C. (FIG. 8B) in Luria broth (pH 6.0) containing 4% birchwood xylan. A sample size of 1 μliter was applied to each lane. Incubation times are given in hours beneath each lane. An acid hydrolystate of xylan was used as a standard in the first lane (S).

Xylose, xylobiose, xylotriose, and xylotetrose were clearly resolved with xylobiose being the dominant product. Monomeric xylose accumulated slowly. A comparison of the extent of digestion after 24 and 48 hours clearly shows that less hydrolysis occurred at 45° C. than at 60° C. despite the instability of xylosidase at 60° C.

Although xylan digestion was incomplete even after 65 hours at 60° C., xylanase remained quite active and was readily detected with 4-methyl-umbelliferyl-β-D-cellobioside as a substrate. Xylosidase was rapidly inactivated at this temperature. No further change in thin layer profiles of xylan hydrolysate were observed after the addition of cell lysates containing both enzymes and incubation at 60° C. for another 24 hours. Thus, the xylooligosaccharide products appear to be near limit digestion products of Sigma birchwood xylan. Oxidation products or substitutions may block complete digestion of this commercial preparation.

Utilization of xylan hydrolysis products by recombinant strains of *E. coli* and *K. oxytoca:* Small scale experiments were conducted to evaluate the extent to which xylooligosaccharides could be metabolized by *E. coli* KO11(pLOI2003) and *K. oxytoca* strain M5A1(pLOI555). These strains were inoculated into 1 ml of xylan hydrolysate (60° C. for 65 hours; supernatant after removal of cell debris by centrifugation) and incubated for 48 hours at 30° C. without agitation. Samples were removed and analyzed by thin layer chromatography (FIGS. 9A and 9B).

Figure 9B:
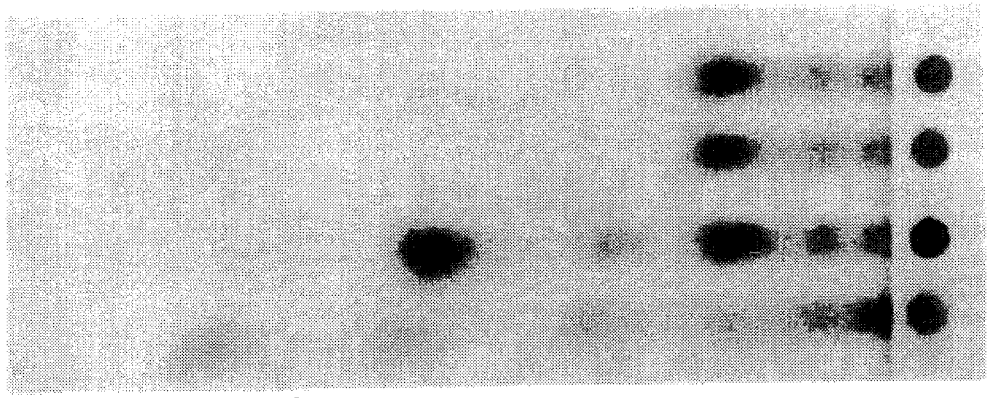
FIGS. 9A and 9B illustrate the utilization of xylooligosaccharides for growth by recombinant *E. coli* KO11 (FIG. 9A) and *K. oxytoca* M5A1 (FIG. 9B).
Figure 9A:
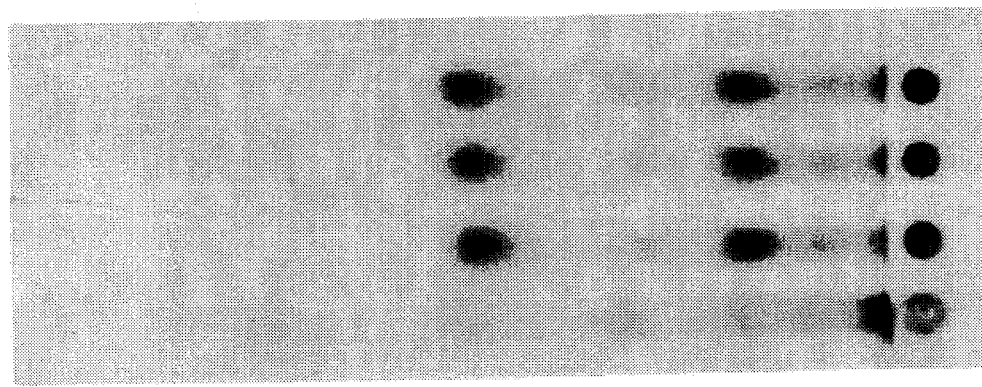

FIGS. 9A and 9B show the utilization of xylooligosaccharides for growth by recombinant *E. coli* KO11 (FIG. 9A) and *K. oxytoxa* M5A1 (FIG. 9B). Xylan (4%) was hydrolyzed for 65 hours by incubation with *E. coli* strain KO11(pLOI2003) in Luria broth (pH 6.0), centrifuged, and sterilized by filtration. Samples were inoculated and incubated at 30° C. to allow growth. Samples were removed at 24 hours intervals as indicated beneath each lane and analyzed by thin layer chromatography. A mixture of xylooligosaccharides was used as a standard in the first lane (S).

Only xylose was metabolized by the recombinant *E. coli* despite the presence of active *B. fibrisolvens* xylosidase. Xylose, xylobiose and xylotriose were all completely consumed by the ethanologenic *K. oxytoca*. Based upon these results, derivatives of *K. oxytoca* were selected as being superior for further studies of xylan conversion to ethanol.

Figure 10A:
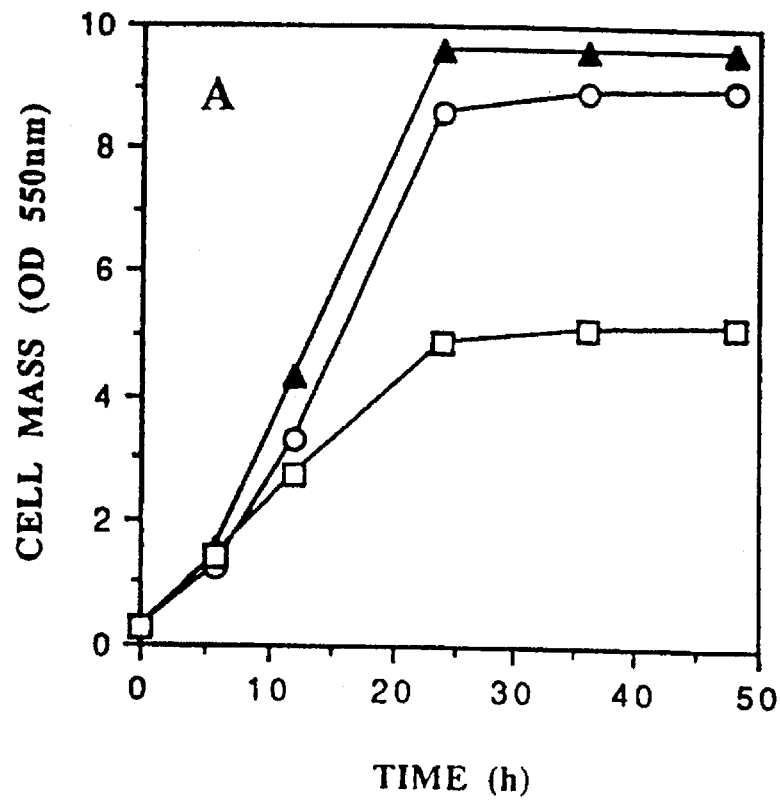
FIGS. 10A and 10B illustrate the conversion of xylose and xylan hydrolysate to ethanol by recombinant *K. oxytoca* M5A1.
Figure 10B:
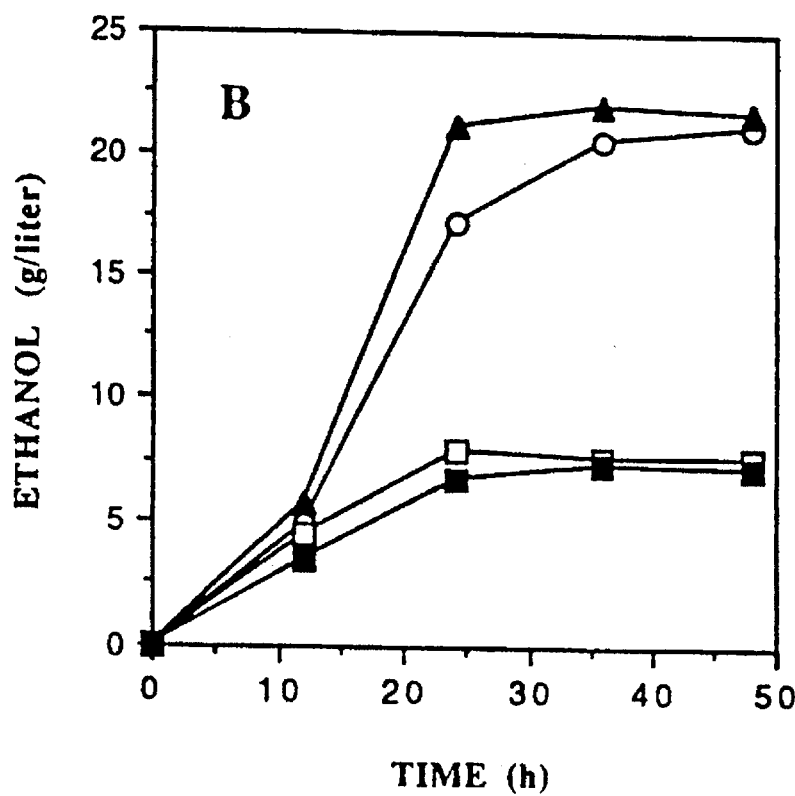

Fermentation of xylose and xylan by derivatives of *K. oxytoca* strain M5A1: Fermentation of xylan was carried out as a two-stage process in which cells harvested from a previous fermentation were resuspended in Luria broth containing 4% xylan for saccharification (60° C. for 65 hours). Saccharified xylan was inoculated and fermented at 30° C. (pH 6.0). Parallel experiments were conducted in which the cell debris had been removed by centrifugation before inoculation. Fermentations were also conducted with 4.47% xylose (equivalent to the xylose content of 4% xylan) for comparison (FIGS. 10A and 10B). The data from those fermentations is provided below in Table 14.

FIGS. 10A and 10B show the conversion of xylose and xylan hydrolysate to ethanol by recombinant *K. oxytoca* M5A1. Xylan was hydrolyzed for 65 hours at 60° C. using cells from a previous fermentation as the source of enzymes. FIG. 10A shows the growth of the cell mass, and FIG. 10B shows the ethanol production. Symbols: ▲, fermentation of 4.47% xylose by M5A1(pLOI555); ○, fermentation of 4.47% xylose by M5A1(pLOI555 and pLOI2001); ■, fermentation of 4% xylan hydrolysate containing cell debris from saccharification by M5A1(pLOI555 and pLOI2001); □, fermentation of 4% xylan hydrolysate after centrifugation to remove cell debris by M5A1(pLOI555 and pLOI2001).

TABLE 14

Ethanol production from xylose and xylan by recombinant strains of *K. oxytoca* M5A1(pLOI555)[a]

| Substrate and second plasmid | Base (mM/g of sugar)[b] | Time[c] (h) | Ethanol Yield g/liter | g/g of substrate | Theoretical yield (%)[d] | VP (g/liter/h)[e] | Cell Yield (g/g of sugar) |
|---|---|---|---|---|---|---|---|
| Xylose (4.47%) | | | | | | | |
| pLOI555 alone | 1.2 | 36 | 22.6 | 0.51 | 99 | 1.29 | 0.07 |

TABLE 14-continued

Ethanol production from xylose and xylan by recombinant
strains of *K. oxytoca* M5A1(pLOI555)[a]

| Substrate and second plasmid | Base (mM/g of sugar)[b] | Time[c] (h) | Ethanol Yield | | | | Cell Yield |
| --- | --- | --- | --- | --- | --- | --- | --- |
| | | | g/liter | g/g of substrate | Theoretical yield (%)[d] | VP (g/liter/h)[e] | (g/g of sugar) |
| with pLOI2001 | 1.5 | 48 | 21.7 | 0.49 | 95 | 1.02 | 0.08 |
| with pLOI2003 | 1.3 | 36 | 20.6 | 0.47 | 91 | 0.83 | 0.07 |
| Xylan (4.0%) | | | | | | | |
| with pLOI2001[f] | 0.7 | 24 | 7.7 | 0.19 | 34 | 0.37 | 0.04 |
| with pLOI2003[f] | 1.3 | 36 | 7.7 | 0.19 | 34 | 0.31 | 0.04 |
| with pLOI2001[g] | 1.3 | 60 | 7.8 | 0.20 | 34 | 0.28 | nd |
| with pLOI2003[g] | 1.1 | 60 | 7.9 | 0.20 | 35 | 0.30 | nd |

[a]Calculations are based on total substrate added.
[b]Amount of base consumed to maintain a pH of 6.0 during fermentation.
[c]Time required to reach maximal ethanol concentration.
[d]Theoretical yield on a weight basis is 0.51 for xylose and 0.56 for xylan.
[e]VP, maximum volumetric productivity during batch fermentation.
[f]Hydrolysate after debris from saccharification was removed by centrifugation.
[g]Hydrolysate containing debris from saccharification.

It is seen that M5A1(pLOI555) produced ethanol very efficiently. Xylose fermentation was essentially completed after 24 hours with 93% of the maximal theoretical yield. Both growth and ethanol production from xylose were reduced by the simultaneous presence of a second plasmid, either pLOI2001 or pLOI2003. Required fermentation times with pLOI2001 increased to approximately 36 hours with 91% of theoretical yield. This decrease in ethanol productivity from monomeric sugar reflects the additional burden imposed by the recombinant enzymes.

Xylan hydrolysis (60° C. for 65 hours) was carried out with M5A1(pLOI555) containing either the hybrid xylanase gene (pLOI2001) or the xylosidase and hybrid xylanase gene (pLOI2003). Thin layer profiles of these hydrolysates appeared identical to those of KO11(pLOI2003), shown in FIGS. 9A and 9B. No differences were found in the extent of xylan hydrolysis between the two M5A1 derivatives.

Growth and ethanol production were measured in these hydrolysates after inoculation with the respective organism used in saccharification (FIGS. 10A and 10B). Growth in clarified hydrolysate was only half that observe with equivalent levels of xylose monomer. Fermentations were essentially complete after 24 hours and appeared slightly faster in clarified hydrolysates. Ethanol yields from xylan were approximately ⅓ of maximal theoretical values, 7.7 to 7.9 g/liter.

Xylooligosaccharides in fermentation broth were monitored by thin layer chromatography. The profiles at the end of fermentation were identical to that shown in FIG. 9B (48 hours). Xylose, xylobiose, and xylotriose were completely metabolized with xylotetrose and longer oligomers remaining.

Discussion: It is thus seen that highly engineered strains of *K. oxytoca* M5A1 can be used both as a source of enzyme for polymer hydrolysis and for ethanol production from xylan. The presence of a native, intracellular xylosidase and the ability to transport and metabolize xylooligosaccharides have not been previously reported for this organism. *E. coli* isolates from nature have been previously described which utilize a phosphotransferase system for cellobiose and an intracellular phosphocellobiase (Hall et al. [1987] J. Bacteriol. 169: 2713–2717; Kricker et al. [1987] Genetics 115: 419–429). Analogous systems may function in *K. oxytoca* M5A1 for xylobiose and xylotriose metabolism. The presence of transport systems and enzymes for the metabolism of xylose monomers, dimers and trimers in *K. oxytoca* M5A1 offers considerable advantage over *E. coli*-based or *S. cerevisiase*-based systems for further development of biomass to ethanol processes.

Many of the previous problems in the genetic engineering of single organisms for polymer degradation and ethanol production are eliminated by using a two-staged process with thermostable enzymes being produced as intracellular products during fermentation. Synthesis of proteins destined to be secreted at high levels often adversely affect normal cellular processes. This problem should be minimized by using N-truncated enzymes in which the secretory signal has been deleted for intracellular expression. Since hydrolysis time is a limiting factor in conversion, high levels of hydrolytic enzymes would be most advantageous at the very beginning of the conversion process to maximize early release of sugars for rapid fermentation. In secretory-based processes, enzyme levels are initially low, accumulating to reach maximal levels near the end of fermentation. However, by using the cells from previous fermentations as a source of enzymes one achieves near maximal levels initially. Although the use of thermostable enzymes for hydrolysis offers additional process advantages for minimizing contamination and may provide higher rates of hydrolysis, a primary advantage is the simplicity of release of intracellular enzymes from harvested cells.

Ethanol tolerance is frequently a problem in native organisms which degrade cellulose and xylan. Such organisms typically produce less than 20 grams of ethanol per liter. (See Taillez et al. [1989] Appl. Environ. Microbiol. 55: 203–06.) Although high level ethanol production from xylan thus far has not been achieved, M5A1(pLOI555) is capable of producing at least 48 g ethanol/liter from 100 g/liter xylose (approximately 95% of maximal theoretical yield).

The overall yield of ethanol from birchwood xylan was lower than anticipated and is believed to be primarily due to incomplete xylan hydrolysis. Undegraded xylooligosaccharides remained after the 65 hours saccharification period. Although the level of xylanase produced by our constructs was below that produced by optimal xylanase fusion constructs reported by Grepinet et al., supra, enzyme level per se did not appear limiting. Xylan (40 g/liter; approximately 0.3 moles of anhydroxylose) should be completely degraded into xylobiose equivalents after 24 hours by hydrolysis a rate of 105 μmoles/min. Cell yields from fermentation were approximately 4.5 g cell protein/liter with a xylanase activity of 144 μmoles/min per g cell protein providing a total activity of 648 μmoles/min. Xylooligosaccharides remained, however, even after 65 hours despite the persistence of active xylanase. These levels of xylooligosaccharides were unchanged by the addition of fresh enzyme and further incubation for 24 hours. Competitive inhibition of hydrolysis by xylooligosaccharides may contribute to incomplete digestion and was tested, in part, by hydrolysis at 45° C., a temperature at which xylanase remained active as did the native enzymes in M5A1 which metabolized xylose, xylobiose, and xylotriose. The oligosaccharide profile under these conditions was identical to that observed after fermentation by M5A1 strains with equivalent levels of the xylotetrose and longer oligosaccharides remaining undigested (data not shown). These oligosaccharides appear to be limit digestion products although the nature of the substitutents limiting digestion remains unknown. According to manufacturer, the birchwood xylan is 99% xylose. While not wishing to be bound to any particular theory, the present inventors speculate that this product may contain oxidized residues generated during storage or substitutions which have survived base extraction and purification (Chesson et al. [1983] J. Sci. Food Agric. 34: 1330–1340).

Fermentative ethanol production in the U.S. is approximately 1 billion gallons (3.8 billion liters) per year (Lynd et al. Science 251:1318–1323). Microorganisms such as the genetically engineered *K. oxytoca*, *E. coli*, *S. cerevisiae*, or *Z. mobilis* could be used to produce a variety of enzymes as coproducts with ethanol. At a minimal cell yield of 2 grams of protein/liter of beer, the diversion of 5% of cell protein would produce at least 3,800,000 kg of enzymes as co-products. These enzymes need not be limited to depolymerization of substrates for fermentation but could also include other enzymes for large markets such as the detergent industry, the food industry, the pulping of wood, and the development of new biocatalyst-based industries for novel chemicals. Providing large markets develop, the value of such enzymes could well exceed current values of ethanol itself.

Example 18—Ethanol Production from Cellobiose, Amorphous Cellulose, and Crystalline Cellulose by Recombinant *Klebsiella oxytoca* containing Chromosomally Integrated *Z. mobilis* Genes for Ethanol Production and Plasmids Expressing Thermostable Cellulase genes from *Clostridium thermocellum*

Summary of Example: In this experiment, the *Z. mobilis* genes for ethanol production have been integrated into the chromosome of *Klebsiella oxytoca* strain M5A1. The best of these constructs, strain P2, produced ethanol efficiently from cellobiose in addition to monomeric sugars. Utilization of cellobiose and cellotriose by this strain eliminated the requirement for external β-glucosidase and reduced the amount of commercial cellulase needed to ferment SOLKA FLOC SW40 (primarily crystalline cellulose). The addition of plasmids encoding endoglucanases from *Clostridium thermocellum* resulted in the intracellular accumulation of thermostable enzymes as co-products with ethanol during fermentation. The best of these, strain P2(pCT603T) containing celD, was used to hydrolyze amorphous cellulose to cellobiose and produce ethanol in a two stage process. Strain P2(pCT603T) was also tested in combination with commercial cellulases. Pretreatment of SOLKA FLOC SW40 at 60° C. with endoglucanse D reduced the amount of commercial cellulase required to ferment SOLKA FLOC by up to 80%. The stimulatory effect of the endoglucanase D pretreatment may result from the hydrolysis of amorphous regions, exposing additional sites for attack by fungal cellulases. Since endoglucanse D functions as part of a complex in *C. thermocellum*, it is possible that this enzyme may complex with fungal enzymes or bind cellulose to produce a more open structure for hydrolysis.

Example 17 demonstrated the advantage of accumulating the *Clostridium thermocellum* xylanase intracellularly in *K. oxytoca* M5A1 as a co-product with ethanol. In this example, the present inventors have integrated the genes for ethanol production into *K. oxytoca* strain M5A1 and demonstrated that the resulting organism can efficiently convert cellobiose to ethanol. This organism appears capable of transporting and metabolizing both cellobiose and cellotriose, eliminating the need for heterologous β-glucosidase. Plasmids added to this integrated construct allowed the production of thermostable endoglucanses as co-products with ethanol, reducing the requirement for commercial cellulases during the fermentation of cellulose.

Organisms and growth conditions: Table 15 lists the new organisms and plasmids used in this study. Strains harboring ethanologenic genes were maintained on Luria agar containing 2% glucose (3); other strains were maintained on Luria agar lacking added sugar. Unless noted otherwise, chloramphenicol (20 μg/ml), tetracycline (6 μg/ml), and ampicillin (50 μg/ml) were used for selection. Typically, *E. coli* strains were grown at 37° C. and *K. oxytoca* strains grown at 30° C. Expression of the ethanologenic operon from *Z. mobilis* was monitored by the rate of color formation on aldehyde indicator plate (Conway et al. [1987] J. Bacteriol. 169:2591–2597). Colonies were screened for cellulase activity by incubating for 1 to 2 hours at 55° C. on Luria agar containing carboxymethyl cellulose followed by staining with Congo Red (Wood et al. [1988] Meth. Enzymol. 160:59–74).

TABLE 15

Bacteria strains and plasmids used in this study

| Bacteria strains/plasmid | Characteristics reference | Source or |
|---|---|---|
| strains | | |
| *K. oxytoca* M5A1(pLOI555) | Cm$^r$,pet$^b$ | Example 15 |
| S1 | Cm$^r$,Ipet$^a$ | this example |
| S2 | Cm$^r$,Ipet$^a$ | this example |
| S3 | Cm$^r$,Ipet$^a$ | this example |
| P1 | Cm$^r$,Ipet$^a$ | this example |
| P2 | Cm$^r$,Ipet$^a$ | this example |
| B1 | Cm$^r$,Ipet$^a$ | this example |
| plasmids | | |
| pCOS2EMBL | Tc$^r$ | Poustka et al.$^c$ |
| pLOI510 | Cm$^r$pet$^b$ | Ohta et al.$^d$ |
| pCT105 | Ap$^r$ celA$^+$ | Cornet et al.$^e$ |
| pCT207 | Ap$^r$ celB$^+$ | Jeffries$^f$ |
| pCT301 | Ap$^r$ Tc$^r$ celC$^+$ | Petre et al.$^g$ |
| pCT603 | Ap$^r$ Tc$^r$ celD$^+$ | Joliff et al.$^h$ |
| pCT105T | Ap$^r$ Tc$^r$ celA$^+$ | this example |
| pCT207T | Ap$^r$ Tc$^r$ celB$^+$ | this example |
| pCT603T | Ap$^r$ Tc$^r$ celD$^+$ | this example |

$^a$Ipet refers to the integration of *Z. mobilis* pdc and adhB genes into the chromosome.
$^b$pet refers to presence of *Z. mobilis* pdc and adhB genes on plasmid pLOI555.
$^c$Poustka et al. [1984] Proc. Natl. Acad. Sci. USA 81:4129–4133.

TABLE 15-continued

Bacteria strains and plasmids used in this study

| Bacteria strains/plasmid | Characteristics reference | Source or |
|---|---|---|

[d]Ohta et al. [1991] Appl. Environ. Microbiol. 57:2810–2815.
[e]Cornet et al. [1983] Bio/Technology 1:589–594.
[f]Jeffries, in J.F. Kennedy et al. (ed.), Wood and Cellulosics: Industrial utilization, biotechnology, structure and properties. John Wiley & Sons, New York (1988).
[g]Petre et al. [1986] Biochimie 68:687–695.
[h]Joliff et al. [1986] Bio/Technology 4:896–900.

Genetic methods and plasmid construction: Standard genetic procedures were used. Integration of pet genes into strain M5A1 was obtained by transforming cells with circularized DNA (lacking all replication functions) containing three essential elements: 1) *E. coli* pfl gene or M5A1 DNA; 2) the *Z. mobilis* pet genes; 3) the cat gene for selection. Recombinants were initially selected using 20 µg chloramphenicol/ml and expressed low levels of *Z. mobilis* enzymes. As with *E. coli* (Ohta et al. [1991] Appl. Environ. Microbiol. 57: 893–900), expression was boosted by direct selection of mutants with resistance to 600 µg chloramphenicol/ml. A single clone expressing high level resistance was retained for each independent integration event.

Tetracycline resistance was added to plasmids containing celA (pCT105), celB (pCT207), and celD (pCT603). Plasmids pCT105 and pCT207 were digested with BamHI followed by treatment with the Klenow fragment of *E. coli* DNA polymerase to create blunt ends. Plasmid pBR322 was digested with EcoRI and similarly treated to produce blunt ends. All three plasmids were then digested with SalI. The resulting small fragment from pBR322 containing the 5'-end of tet was ligated to the larger fragments from pCT105 and pCT207 to reform a functional tet gene (previously inactivated by insertion of *C. thermocellum* DNA), denoted pCT105T and pCT207T, respectively. A 2.5 kilobase pair (kbp) EcoRI fragment from pCOS2EMBL (Poustka et al., supra) containing the complete gene was inserted into the unique EcoRI in pCT603 to produce pCT603T. No modification of pCT301 was needed since this plasmid contained a functional tet gene in addition to celC. All cellulase-containing plasmids were transformed into recombinant *K. oxytoca* with selection for tetracycline resistance.

Cellulase activity: Endoglucanase activity was determined in cells plus broth and in broth alone at 60° C. with p-nitrophenyl-β-D-cellobioside as a substrate (Petre et al., supra). Endoglucanase D activity was also estimated as the release of reducing sugars from amorphous cellulose. Amorphous cellulose (acid swollen and base swollen) were prepared from SOLKA FLOC SW40 as previously described for Avicel (Wood [1988] Meth. Enzymol. 160:19–25). Reducing sugars were measured by using the Nelson-Somogyi method (Bergmeyer et al. [1983] pp 151–152, in Bergmeyer H. U. (ed), Methods of enzymatic analysis, vol. II, 3rd edition, Verlag Chemie, Weinheim, Germany). Initial concentrations of amorphous cellulose were estimated as total carbohydrate by the phenolsulfuric acid method (Wood [1988] Meth. Enzymol. 160:87– 116).

Endoglucanase activities were also compared among ethanologenic cel[+] recombinants by overlaying 18 mm×150 mm culture tubes containing approximately 15 ml of Luria broth solidified with 10% low viscosity carboxymethyl cellulose (Sigma Chemical Company, St. Louis, Mo.) with 2 ml of stationary phase culture. After 48 hours of incubation at 55° C., the extent of liquefaction was determined by inversion.

Products of cellulose digestion were analyzed by thin layer chromatography as described previously for xylosides and xylan digestion (Dorner et al. [1988] Meth. Enzymol. 160:355–362). Glucose, cellobiose, and cellotriose were separated from oligomers. Cellobiose and glucose served as standards.

Fermentation experiments: Fermentations were carried out in 500-ml Fleakers which served as pH stats (350 ml working volume) essentially as described previously (Beall et al., supra). Luria broth containing either 10% glucose or 10% cellobiose was tested at 30° C., pH 6.0, 100 rpm. Inocula for fermentations were grown at 30° C. overnight in unshaken, 250-ml flasks containing 50 ml of Luria broth (4% glucose). After mixing, cell densities were measured at 550 nm and used to calculate the volume required to provide an initial density of 0.32 mg cell dry weight/ml (O.D. 550 nm of 1.0). Cells were harvested from this volume by centrifugation and resuspended in a portion of the broth from each respective pH-stat to start fermentation.

Sugars were sterilized separately by filtration. Cellulose fermentations contained 50 g/liter SOLKA FLOC SW40 (James River Corporation, Saddle Brook, N.J.) and were carried out at 35° C. Cellulose was sterilized by autoclaving as a dry powder. For investigations of cellulose fermentation using commercial enzymes, CYTOLASE or MULTIFECT, was added at the time of inoculation.

Samples were removed for the determination of cell mass (O.D. 550 nm) and ethanol (gas liquid chromatography; Beall et al., supra). Ethanol concentrations are expressed as g/liter. Ethanol yields were corrected for dilution by the addition of base during fermentation and computed on the basis of total sugar or cellulose initially present. No corrections were made for residual carbohydrates. Maximum theoretical yields from glycolysis and fermentation are 0.51 g ethanol/g glucose, 0.536 g ethanol/g cellobiose, and 0.56 g ethanol/g cellulose. Except as indicated, results presented are an average of 2 or more fermentations.

Commercial cellulases: Two commercial cellulases were investigated, CYTOLASE M104 and MULTIFECT CL (Genencor International, Rolling Meadows, Ill.). Both were supplied as liquids, presumably broths from mutant *Trichoderma longibranchiatum* with proprietary amendments. Both are described as containing a mixture of pectinases, cellulases, and hemicellulases. These enzyme preparations are currently optimized for food processing.

Chromosomal integration of *Z. mobilis* pet genes into M5A1: Three approaches were used to integrate pet genes into the chromosome of M5A1 (Orsdov [1984] p. 461–465, in N. R. Kreig and J. G. Holt (ed.), Bergey's manual of systematic bacteriology, vol. 1. The Williams and Wilkins Co., Baltimore). Since *K. oxytoca* and *E. coli* are closely related, the *E. coli* pfl gene was used a potential source of homologous DNA to promote recombination analogous to the method used for *E. coli* (Ohta et al. Appl. Environ. Microbiol. 57:893–900). SalI fragments of 8.6 kbp were purified from pLOI510 which contained pet genes and cat within the pfl gene of *E. coli*. This fragment (lacking genes involved in replication) was circularized by ligation and transformed into M5A1 to allow direct selection for integration. A shorter 5 kbp PstI fragment containing only a small amount of flanking *E. coli* pfl was used in a similar manner. In the third approach, homologous *K. oxytoca* M5A1 DNA (2 kbp random Sau3A fragments) was ligated to a 4.6 kbp BamHI fragment containing only the pet genes with cat (no *E. coli* DNA) and used for transformation. Integrated strains were recovered from all three approaches by selection on Luria broth plates containing 2% glucose and 20 μg Cm/ml. Three integrated clones were recovered with the SalI fragment, two with the PstI fragment and one with the BamHI fragment.

After overnight growth in liquid culture, 0.1 ml of stationary phase cells was spread on plates containing 600 μg Cm/ml and 2% glucose to select for high level expression. Single large colonies were retained from each independent integration event and named according to the restriction site used for construction, i.e., S1, S2, S3, P1, P2, and B1. These clones were tested for the presence of plasmids by transformation of miniscreen DNA and for expression of pet genes on aldehyde indicator plates (Table 16). Putative integrated strains found to contain plasmid-borne cat genes were discarded after digesting miniscreen DNA to confirm the presence of pLOI510 (presumably a low level contaminant of gel-purified fragments). The parent organism and M5A1(pLOI555), an excellent ethanol producer, were included as negative and positive controls, respectively. Two clones expressed the ethanol genes at levels nearly equivalent to that of that of M5A1(pLOI555), strains B1 and P2.

TABLE 16

Fermentation of 10% glucose (48 hours) by strains of M5A1 containing integrated pet genes.

| Strain[a] | Base (mM/liter) | Cell Mass[b] (g/liter) | Ethanol (g/liter) | Aldehyde[c] Plates | Plasmid[d] |
|---|---|---|---|---|---|
| M5A1 | 108 | 3.2 | 15 | – | – |
| M5A1(pLOI555) | 91 | 5.1 | 45 | ++++ | + |
| S1 | 120 | 2.9 | 37 | + | – |
| S2 | 171 | 3.2 | 44 | ++ | – |
| S3 | 97 | 2.4 | 37 | ++ | – |
| P1 | 120 | 2.0 | 38 | ++ | – |
| P2 | 91 | 3.7 | 44 | +++ | – |
| B1 | 63 | 4.0 | 47 | ++++ | – |

[a]Values reported are from a single experiment although many were reproduced and averaged in subsequent investigations.
[b]Cell mass was calculated from the maximal O.D. at 550 nm (approx. 0.32 g dry weight/liter per O.D. unit).

TABLE 16-continued

Fermentation of 10% glucose (48 hours) by strains of M5A1 containing integrated pet genes.

| Strain[a] | Base (mM/liter) | Cell Mass[b] (g/liter) | Ethanol (g/liter) | Aldehyde[c] Plates | Plasmid[d] |
|---|---|---|---|---|---|

[c]Comparative rate of color development on aldehyde indicator plates at 30° C. was used as a relative measure of expression from the pet operon.
[d]Small scale preparations of DNA were examined on agarose submarine gels and tested for their ability to transfer antibiotic resistance to *E. coli* DH5α during transformation.

Comparison of glucose fermentation by integrated strains to M5A1(pLOI555): After 48 hours, high levels of ethanol equivalent to M5A1(pLOI555) were produced by 4 strains containing pet integrations (Table 16). The two which produced the lowest levels of acidic co-products also grew to the highest densities. These strains, P2 and B1, were selected for further investigation.

Fermentation of glucose and cellobiose by strains P2 and B1. Strains P2 and B1 were investigated for their ability to ferment 10% glucose and 10% cellobiose (Table 17). During glucose fermentation (FIG. 11A), both integrated strains produced 3 times more ethanol than the parent organism, M5A1, but were slightly inferior to M5A1(pLOI555) (plasmid-borne pet genes) in yield, and in volumetric productivity. Unexpectedly, integration and high level expression of pet genes in strain B1 was accompanied by a loss of ability to ferment cellobiose. Strain P2, however, grew well and produced ethanol from cellobiose (FIG. 11B) with 96% of the maximum theoretical yield.

Figure 11A:
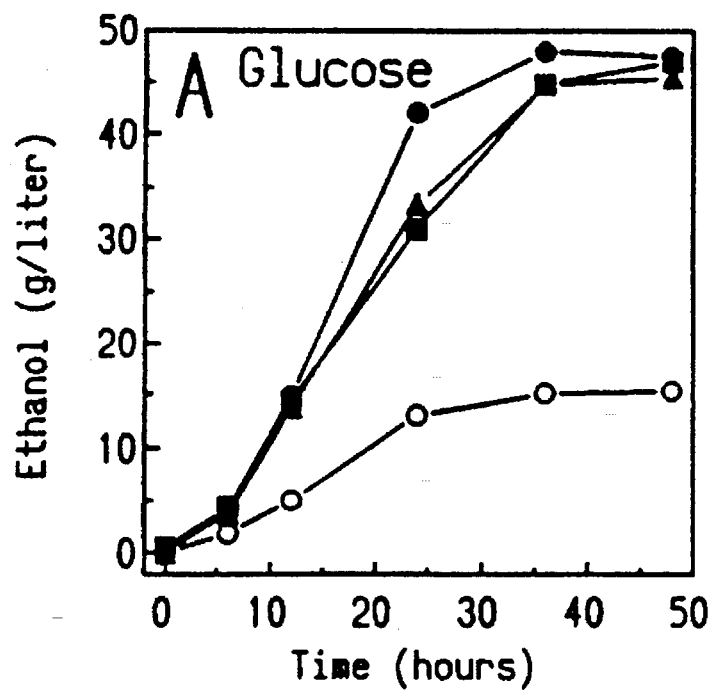
FIGS. 11A and 11B illustrate the ethanol production by recombinant strains of *K. oxytoca* M5A1.
Figure 11B:
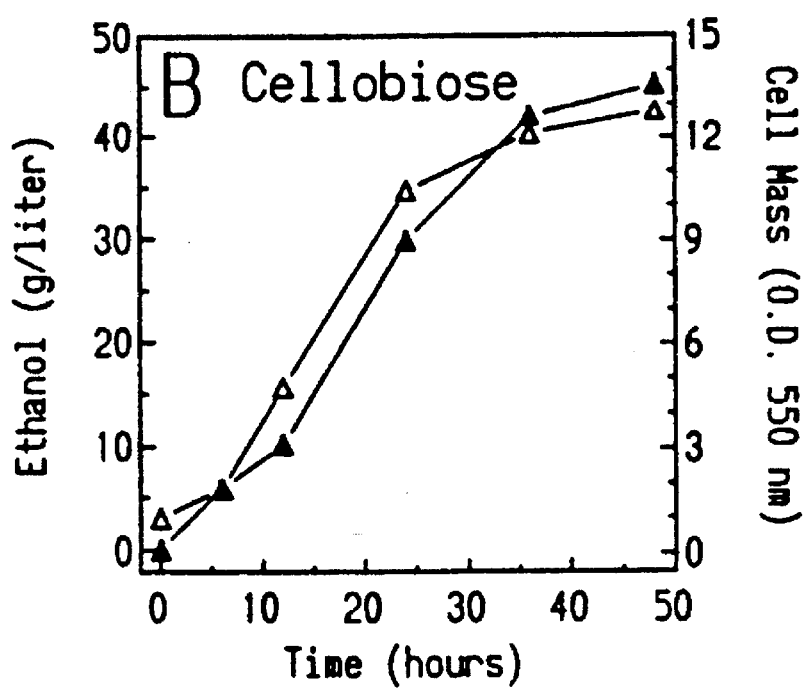

FIGS. 11A and 11B thus illustrate the ethanol production by recombinant strains of *K. oxytoca* M5A1. FIG. 11A illustrates the production from glucose (100 g/liter). Symbols: ●, strain M5A1(pLOI555); ▲, strain P2 containing integrated pet genes; ■, strain B1 containing integrated pet genes; ○, M5A1 control. FIG. 11B illustrates the production from cellobiose (100 g/liter) fermentation by strain P2. Symbols: ▲, ethanol; △, cell mass.

TABLE 17

Ethanol production by recombinant strains of *K. oxytoca* M5A1 and by *E. coli* KO11.

| Organism[a] | Substrate | Additives[b] | Volumetric Productivity (g/liter/h) | Max. EtOH (g/liter) | Yield (g/g S) | % Theoretical[c] Yield |
|---|---|---|---|---|---|---|
| M5A1 | 10% glucose | none | 0.72 | 16.2 | 0.17 | 33 |
| M5A1(PLOI555) | " | " | 2.1 | 48.0 | 0.50 | 99 |
| P2 | " | | 1.6 | 46.4 | 0.46 | 90 |
| B1 | " | " | 1.5 | 47.6 | 0.49 | 96 |
| P2 | 10% cellobiose | " | 1.5 | 45.2 | 0.49 | 96 |
| B1 | " | " | 0.1 | 1.2 | 0.01 | 2 |
| P2(pCT1057) | 10% glucose | " | 0.13 | 16.0 | 0.17 | 33 |
| P2(pCT301) | " | " | 0.58 | 19.4 | 0.20 | 40 |
| P2(pCT603T) | " | " | 0.83 | 30.0 | 0.32 | 62 |
| P2 | none | " | 0.04 | 1.0 | — | — |
| P2 | none | 10% CYTOLASE | 0.12 | 4.7 | — | — |
| P2 | none | 10% MULTIFECT | 0.06 | 5.2 | — | — |
| P2 | 5% SOLKA FLOC SW40 | no enzyme | 0.05 | 2.0 | 0.04 | 8 |
| P2(pCT603T)[f] | " | 1.0% CYTOLASE | 0.09 | 17.4 | 0.36 | 65 |

TABLE 17-continued

Ethanol production by recombinant strains of *K. oxytoca* M5A1 and by *E. coli* KO11.

| Organism[a] | Substrate | Additives[b] | Volumetric Productivity (g/liter/h) | Max. EtOH (g/liter) | Yield (g/g S) | % Theoretical[e] Yield |
|---|---|---|---|---|---|---|
| P2(pCT603T)[c] | " | 1.0% MULTIFECT | 0.16 | 17.4 | 0.36 | 65 |
| P2 | 5% SOLKA FLOC SW40 | 0.1% CYTOLASE | 0.08 | 2.3 | 0.07 | 12 |
| P2 | " | 0.5% CYTOLASE | 0.13 | 7.0 | 0.14 | 26 |
| P2 | " | 1.0% CYTOLASE | 0.18 | 8.7 | 0.18 | 32 |
| P2 | " | 5.0% CYTOLASE | 0.52 | 16.9 | 0.36 | 64 |
| P2 | " | 10% CYTOLASE | 0.50 | 16.3 | 0.35 | 62 |
| P2 | 5% SOLKA FLOC SW40 | 0.1% MULTIFECT | 0.08 | 3.3 | 0.07 | 12 |
| P2 | " | 0.5% Mutifect | 0.18 | 5.9 | 0.13 | 23 |
| P2 | " | 1.0% MULTIFECT | 0.36 | 10.4 | 0.23 | 41 |
| P2 | " | 5.0% MULTIFECT | 0.76 | 23.8 | 0.51 | 92 |
| P2 | " | 10% MULTIFECT | 0.86 | 32.5 | 0.69 | 123 |
| KO11 | 5% SOLKA FLOC SW40 | 0.1% CYTOLASE | 0.05 | 1.8 | 0.04 | 7 |
| KO11 | " | 0.5% CYTOLASE | 0.08 | 5.1 | 0.11 | 19 |
| KO11 | " | 1.0% CYTOLASE | 0.13 | 6.2 | 0.13 | 23 |
| KO11 | " | 5.0% CYTOLASE | 0.51 | 14.7 | 0.31 | 56 |
| KO11 | " | 10% CYTOLASE | 0.32 | 8.0 | 0.17 | 30 |
| KO11 | 5% SOLKA FLOC SW40 | 0.1% MULTIFECT | 0.06 | 2.2 | 0.05 | 8 |
| KO11 | " | 0.5% MULTIFECT | 0.08 | 2.7 | 0.06 | 10 |
| KO11 | " | 1.0% MULTIFECT | 0.18 | 5.6 | 0.12 | 21 |
| KO11 | " | 5.0% MULTIFECT | 0.43 | 20.6 | 0.43 | 76 |
| KO11 | " | 10% MULTIFECT | 0.84 | 30.7 | 0.63 | 112 |

[a]Glucose and cellobiose fermentations were carried out at 30° C.; other fermentations were carried out at 35° C.
[b]Enzymes were added at the time of inoculation.
[c]Computed for the time period between 6 and 24 hours.
[d]Corrected for dilution by the addition of base during fermentation. S (substrate) refers to glucose, cellobiose or SOLKA FLOC SW40.
[e]Based on a maximum theoretical yield of 51 g ethanol/100 g glucose, 53.5 g ethanol/100 g cellobiose, and 28 g ethanol/50 g cellulose. Values were not corrected for residual substrate.

TABLE 17-continued

Ethanol production by recombinant strains of K. oxytoca M5A1 and by E. coli KO11.

| Organism[a] | Substrate | Additives[b] | Volumetric Productivity (g/liter/h) | Max. EtOH (g/liter) | Yield (g/g S) | % Theoretical[c] Yield |
|---|---|---|---|---|---|---|

[f]SOLKA FLOC SW40 was predigested at 60° C. for 12 h by using cells harvested from a prior fermentation as a source of C. thermocellum celD. After cooling to 35° C., broth was inoculation and 1 ml of commercial cellulase/100 ml fermentation volume added to start the fermentation.

Comparison of crystalline cellulose fermentation (SOLKA FLOC SW40) by recombinant K. oxytoca M5A1 to E. coli in the presence of different concentrations of commercial cellulases: In contrast to ethanologenic E. coli which utilize only glucose, recombinant K. oxytoca P2 can ferment cellobiose and do not require exogenous β-glucosidase during cellulose fermentation. To examine the extent to which cellobiose utilization improves ethanol production from cellulose using commercial enzymes, fermentations were conducted with 50 g SOLKA FLOC SW40 as a substrate in the presence of either CYTOLASE or MULTIFECT concentrations from 0 to 10% (FIG. 12; Table 17). These preparations contain a mixture of fungal enzymes which include endoglucanases, exoglucanases, and β-glucosidases.

Figure 12:
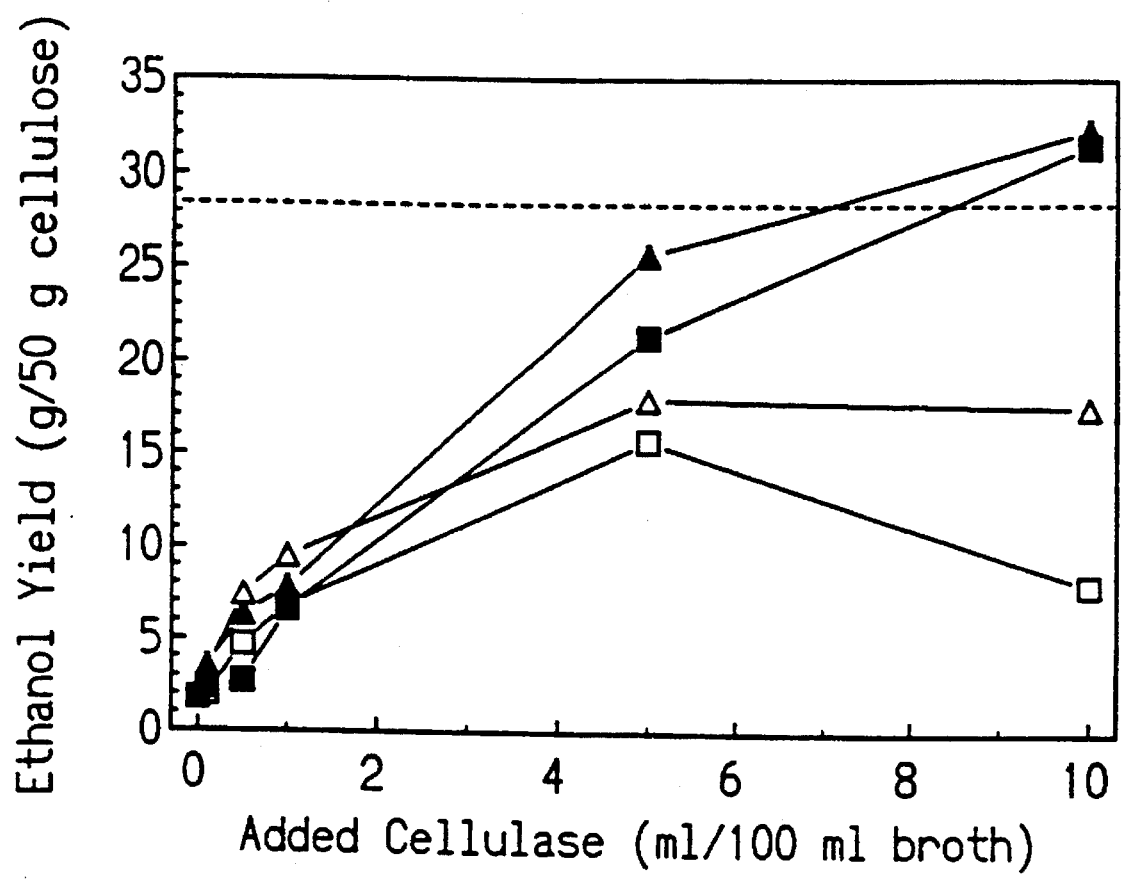
FIG. 12 illustrates the effect of commercial cellulase additions on ethanol yield from 50 g SOLKA FLOC SW40/liter after 120 hours.

FIG. 12 thus illustrates the effect of commercial cellulase additions on ethanol yield from 50 g SOLKA FLOC SW40/liter after 120 hours. The dotted line indicates the maximum amount of ethanol which can be made from only the added cellulose. The higher levels of ethanol are attributed primarily to additional substrate added as proprietary amendments in the MULTIFECT CL preparation. Symbols: ▲, fermented with K. oxytoca P2 and MULTIFECT; ■, fermented with strain E. coli KO11 and MULTIFECT; Δ, fermented with K. oxytoca P2 and CYTOLASE; □, fermented with E. coli KO11 and CYTOLASE.

At low concentrations, CYTOLASE appeared more efficient although some toxicity was associated with higher concentrations of this enzyme preparation. In all cases, the performance of the integrated strain of K. oxytoca was superior to E. coli KO11 despite the presence of β-glucosidase in commercial preparations of cellulase. Together, these results suggest that β-glucosidase activity commercial cellulase preparations may not be saturating relative to the other cellulase activities.

With the highest concentration of MULTIFECT, yields exceeding the theoretical maximum from 50 g cellulose/l were observed. The source of this additional ethanol was investigated by conducting fermentations in Luria broth without added carbohydrate or enzymes and in Luria broth containing 10% CYTOLASE or 10% MULTIFECT but lacking added carbohydrate. Approximately 1 g ethanol/liter was produced from Luria broth alone and 5 g ethanol/liter from Luria broth containing 10% added cellulase. Thus with fermentations containing 10% MULTIFECT, approximately 4 g ethanol/liter can be attributed to the fermentation of commercial additives or enzyme stabilizing agents. It is likely that proportionate amounts of ethanol are also produced from lower concentrations of cellulases. Correcting for ethanol which could have been produced from Luria broth constituents and 10% MULTIFECT, ethanol yields from cellulose are approximately 94% of the theoretical maximum.

Expression of C. thermocellum cellulases in strain P2: Cellobiose can be fermented by strain P2 and is the dominant product from cellulose digestion by endoglucanases and exoglucanases. Although neither enzyme is made by our organism, integration of the pet genes into the chromosome facilitates the inclusion of plasmids encoding heterologous genes to provide these enzymes as co-products during fermentation. The expression of four endoglucanases from the thermophile, Clostridium thermocellum, was investigated after the addition of tetracycline resistance for selection (Table 18). The celD gene has been expressed at very high levels in E. coli and was expressed at high levels in strain P2. Most of the endoglucanase activity produced from these genes was retained within the cells although Klebsiella strains are known have protein secretion systems and the possibility of partial secretion was not eliminated.

A qualitative comparison of effectiveness in liquefaction of CMC was conducted in culture tubes during 48 hours incubation at 55° C. Consistent with activity measurements, recombinant cells harboring celD (pCT603T) were most effective followed by celC (pCT301). Strain P2 harboring celB (pCT207T) grew very poorly and was not tested further. CelA (pCT105T) recombinants caused little liquefaction.

The effects of producing heterologous gene products on fermentation performance were also investigated. Addition of plasmids expressing any one of the cel genes decreased the final cell density in 10% glucose fermentations by 10%–30% and decreased ethanol yield (Table 18). Expression of the celD gene was the least harmful with an ethanol yield of 0.32 g ethanol per gram of glucose, 62% of the theoretical maximum. Assays were conducted at 60° C. using p-nitrophenyl-β-D-cellobioside as the substrate. Units are μmoles hydrolyzed per min per ml of fermentation broth containing cells or broth after cells had been removed by centrifugation.

TABLE 18

Expression of C. thermocellum endoglucanases genes in strain P2.

| | | Activity (U/ml) | | |
|---|---|---|---|---|
| Gene | Plasmid | cells + broth | broth | % cell-associated |
| control | none | 0.2 | — | — |
| celA | pCT105T | 2.3 | 0.4 | 83 |
| celB | pCT207T | 17 | 0.8 | 95 |
| celC | pCT301 | 41 | 6.2 | 85 |
| celD | pCT603T | 49 | 13 | 73 |

Hydrolysis and fermentation of amorphous cellulose by strain P2 expressing celD. Although the celD gene product will not hydrolyze crystalline cellulose, this enzyme has been previously shown to hydrolyze amorphous cellulose (Bèguin et al., Joliff et al., supra). Strain P2(pCT603T) expressing this gene was tested for its ability to convert amorphous cellulose to ethanol. Phosphoric acid swollen and base swollen (sodium hydroxide) SOLKA FLOC SW40 were tested in a two-stage batch process using the cells of P2(pCT603T) from a prior glucose fermentation as a source of endoglucanase D and the same organism to produce ethanol.

The first step consisted of incubating 3 ml of Luria broth containing 76 mg/ml acid swollen cellulose or 32 mg/ml base swollen cellulose at 60° C. (pH 6.0) for 72 hours using cells harvested from an equivalent volume from a prior glucose fermentation. Heating to 60° C. inactivated cells to release endoglucanase D and provided a near optimal temperature for activity. The release of reducing sugars was measured during hydrolysis. Although substrate concentrations were different, acid swollen cellulose was hydrolyzed at twice the rate of base swollen cellulose to produce 240 µmolar and 60 µmolar cellobiose equivalents, respectively, after 24 hours. The acid swollen cellulose became quite viscous making sampling difficult. After 72 hours, 110 µmolar cellobiose equivalents were present in the digestion of base swollen cellulose. These yields reflect the near complete hydrolysis of both acid swollen and base swollen cellulose.

Figure 13C:
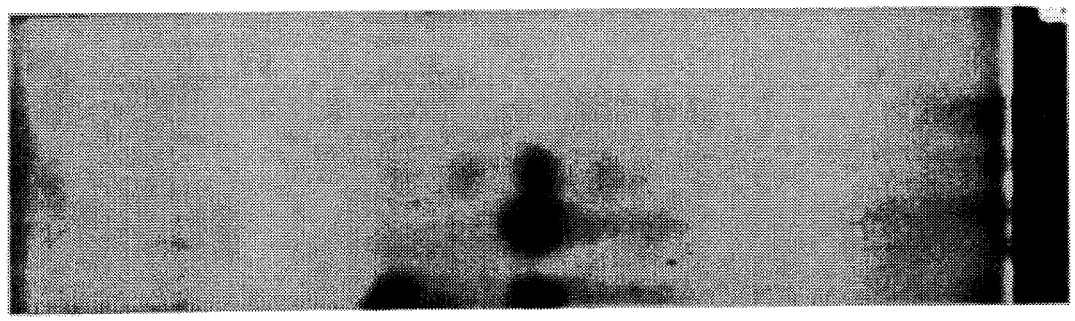
FIGS. 13A, B and C comprise the thin layer chromatographic analyses of cellulose hydrolysis and fermentation by P2(pCT603T) of acid swollen cellulose (FIG. 13A), base swollen cellulose (FIG. 13B), and crystalline cellulose (FIG. 13C).
Figure 13B:
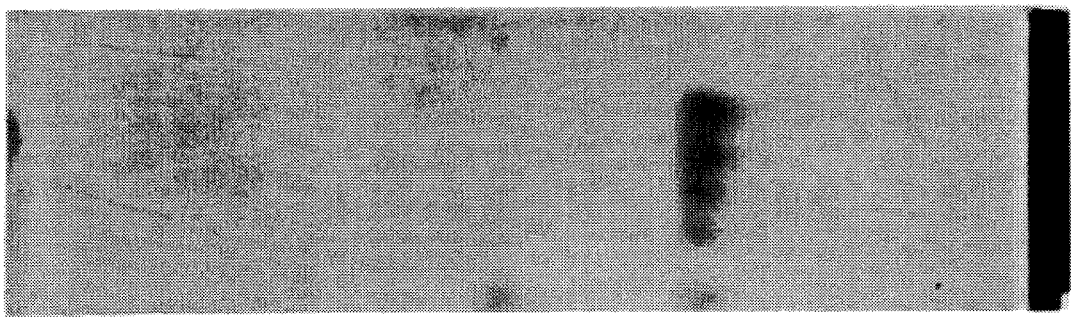
Figure 13A:
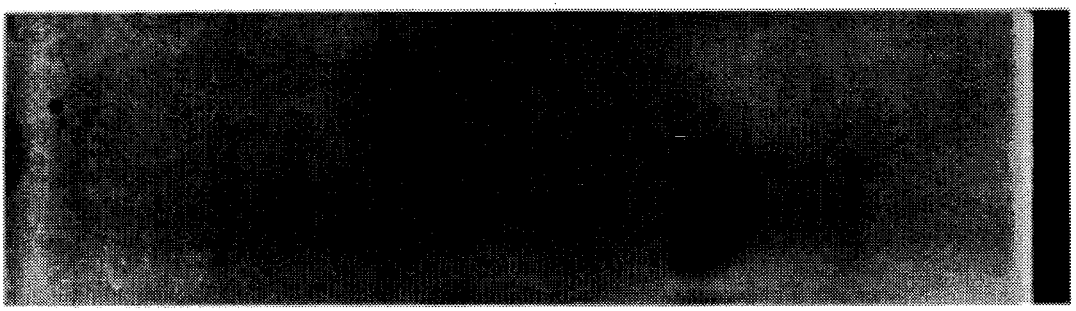

FIGS. 13A, B and C comprise the thin layer chromatographic analyses of cellulose hydrolysis and fermentation by P2(pCT603T). Acid swollen cellulose (FIG. 13A), base swollen cellulose (FIG. 13B), and crystalline cellulose (FIG. 13C; SOLKA FLOC SW40) were tested. Cellobiose and glucose were used as standards in lane 1 of each chromatogram. In FIGS. 13A and B, lanes 2 through 6 represent samples removed at various times during hydrolysis of amorphous cellulose (0, 6, 12, 24, 48 and 72 hours, respectively); lane 7 represents broth analyzed in lane 6 after fermentation for 24 hours at 30° C. with strain P2(pCT603T).

FIG. 13C comprises the thin layer chromatographic analysis of crystalline cellulose (SOLKA FLOC SW40) fermentation with 1% MULTIFECT and P2(pCT603T) expressing C. thermocellum celD. The lane compositions are as follows: 2, SOLKA FLOC suspension immediately prior to digestion; 3, broth after 24 hours of digestion at 60° C. with endoglucanase D supplied by P2(pCT603T) from a prior fermentation; 4, broth shown in lane 3 after fermentation for 24 hours at 35° C. by P2(pCT603T); 5, after an additional 24 hours of fermentation by P2(pCT603T) at 35° C. (total fermentation, 48 hours).

Thus, lanes 2–6 in FIGS. 13A and 13B reveal the cellulose digestion products at various times from acid swollen and base swollen cellulose, respectively. Cellobiose is the dominant product in both with a small amount of glucose. Low levels of cellotriose also were present in digests of acid swollen cellulose. After cooling to 35° C., these broths were inoculated with 50 µliter of P2(pCT603T) and allowed to ferment without agitation or pH control for 24 hours. Glucose, cellobiose, and cellotriose were removed completely during this period (FIG. 13 A & B, lane 7) with the production of approximately 5 g ethanol/liter. For base swollen cellulose, 0.16 g ethanol/g cellulose was produced. Although the fall in pH probably served to limit the extent of ethanol production, this ethanol yield is equivalent to 27% of the theoretical maximum.

Partial replacement of commercial cellulase by endogenous production of C. thermocellum endoglucanase: Although P2(pCT603T) does not require externally added β-glucosidase and can provide endoglucanase D which will hydrolyze amorphous cellulose, additional activities are required to hydrolyze crystalline cellulose. The ability of this strain to partially replace the requirement for commercial cellulase was tested in a two stage fermentation process. Cells harvested from a prior glucose fermentation were resuspended in an equivalent volume of Luria broth containing 50 g SOLKA FLOC SW40/liter and incubated at 60° C. for 24 hours. After cooling to 35° C., these fermentations were inoculated with the same organism along with 1% commercial cellulase. Similar results were obtained for both CYTOLASE and MULTIFECT with the production of 17.4 g ethanol/liter, 65% of the maximum theoretical yield (Table 17).

Figure 14:
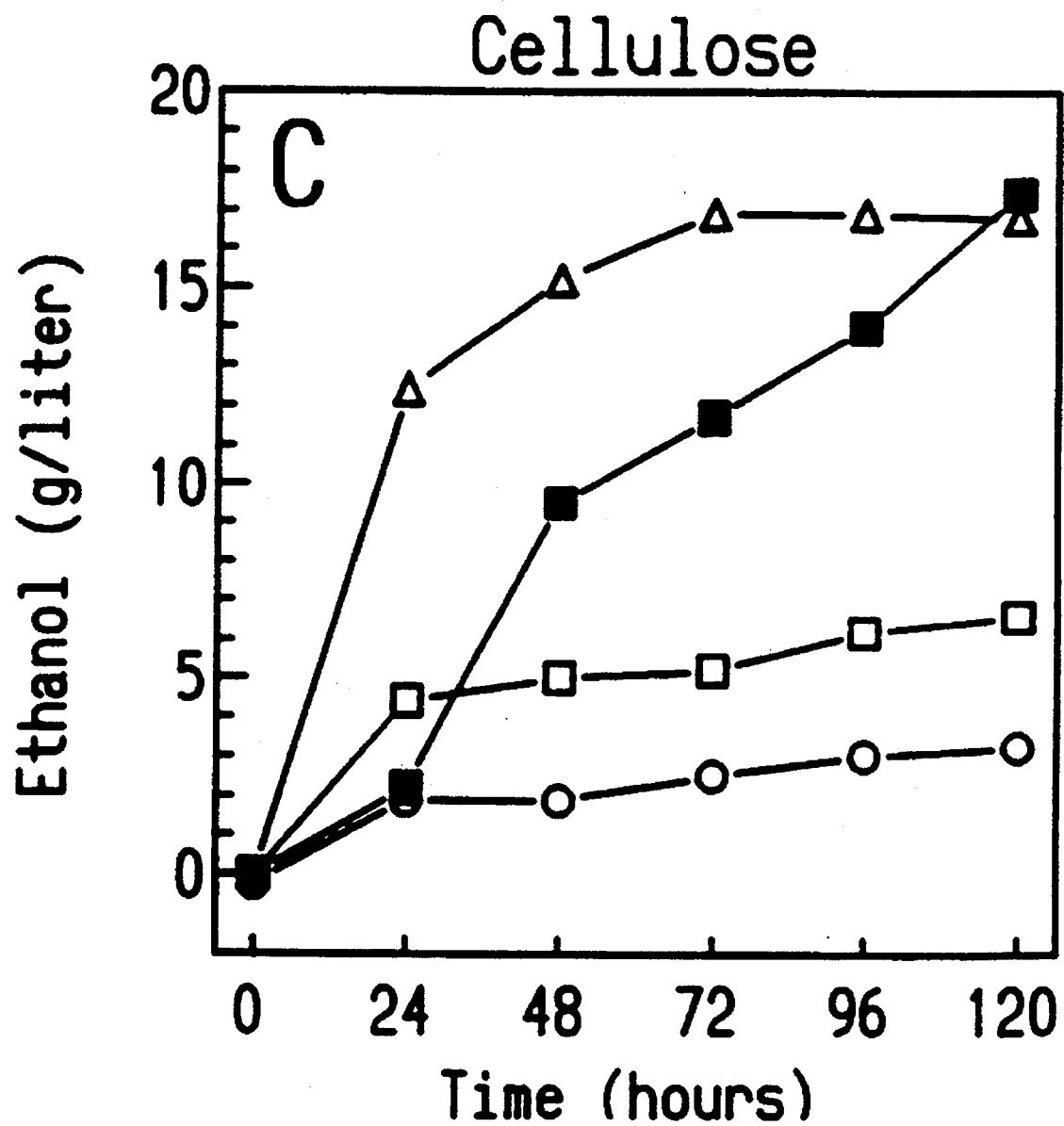
FIG. 14 illustrates the enhancing effect on ethanol production of pretreatment with the celD gene product and using 1% cellulase, which provides an ethanol yield equivalent to that of 5% CYTOLASE.

As illustrated in FIG. 14 for CYTOLASE, pretreatment with the celD gene product greatly enhanced the ethanol production using 1% cellulase, providing an ethanol yield equivalent to that of 5% CYTOLASE. In FIG. 14, cellulose (50 g SOLKA FLOC SW40/liter) was incompletely saccharified with CYTOLASE and endoglucanase D and fermented by strains P2 and P2(pCT603T). Symbols: Δ, 5 ml CYTOLASE added per 100 ml broth at time of inoculation and fermented with P2; □, 1 ml CYTOLASE added per 100 ml broth at time of inoculation and fermented with P2; ○, 0.1 ml CYTOLASE added per 100 ml broth at time of inoculation and fermented with P2; ■, SOLKA FLOC predigested at 60° C. for 12 hours by using P2(pCT603T) cells harvested from a prior fermentation as a source of C. thermocellum endoglucanase D and fermented. After cooling to 35° C., 1 ml of commercial cellulase/100 ml fermentation broth and P2(pCT603T) were added to start the fermentation.

FIG. 13C shows a thin layer chromatogram of samples from different stages of a parallel two step fermentation with MULTIFECT. Again, glucose, cellobiose, and cellotriose were completely metabolized. Thus the amount of commercial cellulase needed for saccharification was reduced by up to 80% after pretreatment with recombinant endoglucanase D produced as a co-product with ethanol in a prior fermentation.

Discussion: It is known that hydrolysis of cellobiose to monomeric sugar by β-glucosidase often limits cellulose digestion by fungal broths. The activity of β-glucosidase is typically the least abundant and least stable of the enzyme cadre required for efficient cellulose hydrolysis. The accumulation of cellobiose as a product of cellulase action acts as a competitive inhibitor of further depolymerization (Eriksson et al. [1990] Microbial and enzymatic degradation of wood and wood components. Springer-Verlag, New York; Jeffries, supra). K. oxytoca P2 is the first organism reported to rapidly and efficiently convert cellobiose to high levels of ethanol.

This organism appears to have the capacity to actively transport cellobiose and cellotriose, minimizing cellobiose accumulation and eliminating the requirement for further depolymerization by external enzymes. Although transport systems for cellobiose have not been investigated in K. oxytoca (Al [1989] J. Biotechnol. 12:79–86), the closely related organism E. coli contains genes which encode phosphotransferase components and phosphoglucosidase for cellobiose metabolism which are cryptic in most laboratory strains but function in nature (Hall et al. J. Bacteriol. 169:2713–2717; Kricker et al. [1987] Genetics 115:419–429). It is likely that similar genes function in K. oxytoca (Al, supra).

Integration of the pet genes for ethanol production into the chromosome facilitated the production of plasmid-borne, recombinant proteins as co-products with ethanol. Although cellulase genes from C. thermocellum were used as an example, other more valuable recombinant products could also be made such as lipases, proteinases, glycohydrolases, animal hormones, and biomedical products. The production of *C. thermocellum* cellulases by strain P2 as a co-product was accompanied by an unexpected decrease in the efficiency of fermentation. The basis for this decreased efficiency is unknown although the present inventors have made similar observations with ethanologenic *E. coli* containing the pullulanase gene from *Thermoanaerobium brockii* and with multi-plasmid ethanologenic constructs of *K. oxytoca* expressing the *C. thermocellum* xylanase gene.

The foregoing example with *K. oxytoca* thus forms the basis for an improved process to convert cellulose into ethanol. It is known that cellobiose and cellotriose are inhibitors of endoglucanase and exoglucanase, and that β-glucosidase is responsible for converting those oligomers into glucose monomers. Ethanologenic recombinants such as strain P2, however, do not require depolymerization of sugars for metabolism, eliminating the need for β-glucosidase and reducing end-product inhibition of cellulases by cellobiose and cellotriose. A further advantage is the reduction in potential contaminants since fewer organisms are able to metabolize cellobiose or cellotriose as compared to monomeric glucose. Based upon comparisons with *E. coli* KO11, which lack cellobiose utilization, the transport and metabolism of cellobiose exhibited by *K. oxytoca* P2 decreased the requirement for commercial enzymes during cellulose fermentation.

The requirement for commercial cellulases was further reduced by using supplemental endoglucanase produced as a co-product during fermentation. In this regard, thermostable enzymes appear particularly useful since they can be readily harvested within cells after fermentation and released in active form simply by heating to the temperature at which they function best. Pretreatment of SOLKA FLOC SW40 with endoglucanase D from a prior fermentation dramatically increased the effectiveness of Genencor cellulases. Since endoglucanase D is active only on amorphous regions of cellulose (Bèguin et al., supra), the beneficial effect of this pretreatment may result from the creation of new sites for attack by commercial cellulases. In *C. thermocellum*, endoglucanase D is part of a cellulase complex (Bèguin et al., supra). It is possible that this enzyme may also complex with fungal enzymes or bind cellulose and facilitate an opening of cellulose structure for hydrolysis.

The best construct for cellulose fermentation to ethanol, P2(pCT603T), is not as effective as native *C. thermocellum* (Tailliez et al. [1989] Appl. Environ. Microbiol. 55:203–211). Unlike *C. thermocellum*, *K. oxytoca* P2(pCT603T) lacks a complete cellulase system. However, in combination with 1% commercial CYTOLASE or MULTIFECT, P2(pCT603) produced higher yields and final concentrations of ethanol at 35° C. than the ethanol-tolerant *C. thermocellum* mutants at 65° C. Further genetic improvements or process improvements may be desirable.

Example 19—Ethanol Production from Starch by Recombinant *Escherichia coli* containing Chromosomally Integrated *Z. mobilis* Genes for Ethanol Production and Plasmids Expressing Thermostable Genes for Saccharification Summary of Example: Ethanologenic strains of *E. coli* have been developed which can express thermostable enzymes for starch saccharification as intracellular products. These enzymes can be harvested within cells at the end of fermentation and liberated by heating to the temperature at which they exhibit maximal activity (60° C. to 70° C.). Organisms such as these could be used to supply enzymes for yeast-based fermentations while producing a small amount of ethanol as a co-product.

In this example, advantage is taken of the absence of a protein secretion system in *E. coli* by developing ethanologenic strains which express genes encoding thermostable α-amylase and pullulanase as intracellular products. Thermostable enzymes are harvested within cells at the end of fermentation and are released for starch saccharification simply by heating to the temperature at which these enzymes exhibit near optimal activity.

Organisms and growth conditions: All ethanol fermentations were conducted in Luria broth with added carbohydrate using *E. coli* strain KO11 (Ohta et al., 1991). Plasmids were added to this strain as indicated.

Plasmid construction: Two plasmids, pLOI140 and pLOI141 (FIGS. 15A and B), were constructed which contained the α-amylase gene from *Bacillus stearothermophilus* (Mielenz et al. [1985] U.S. Pat. No. 4,493,893) and the pullulanase gene from *Thermoanaerobium brockii* (Coleman et al. [1986] U.S. Pat. No. 4,612,287; Coleman et al. [1987] J. Bacteriol. 169:4302–4307) using standard methods. A 5.4 kilobase pair (kbp) HindIII fragment from pWL625Amy (ATCC 31,791) containing the amylase gene was inserted into a HindIII site of pCPC902 (Coleman et al. [1986] supra.) after partial digestion. Comparison of constructs on Luria agar containing starch and pullulan-red indicated that insertions at only one site allowed retention of high level expression for both genes, pLOI568. A 2.5 kbp EcoRI fragment from pCOS2EMBL (Poustka et al. [1984] Proc. Natl. Acad. Sci. USA 81:4129–4133) containing a tetracycline gene was added to pLOI568 after partial digestion with EcoRI to produce pLOI140 and pLOI141. The final plasmids contained a pBR322 replicon and were quite stable in strain KO11, being retained by 96% of the cells after 48 generations without antibiotic selection.

Figure 15A:
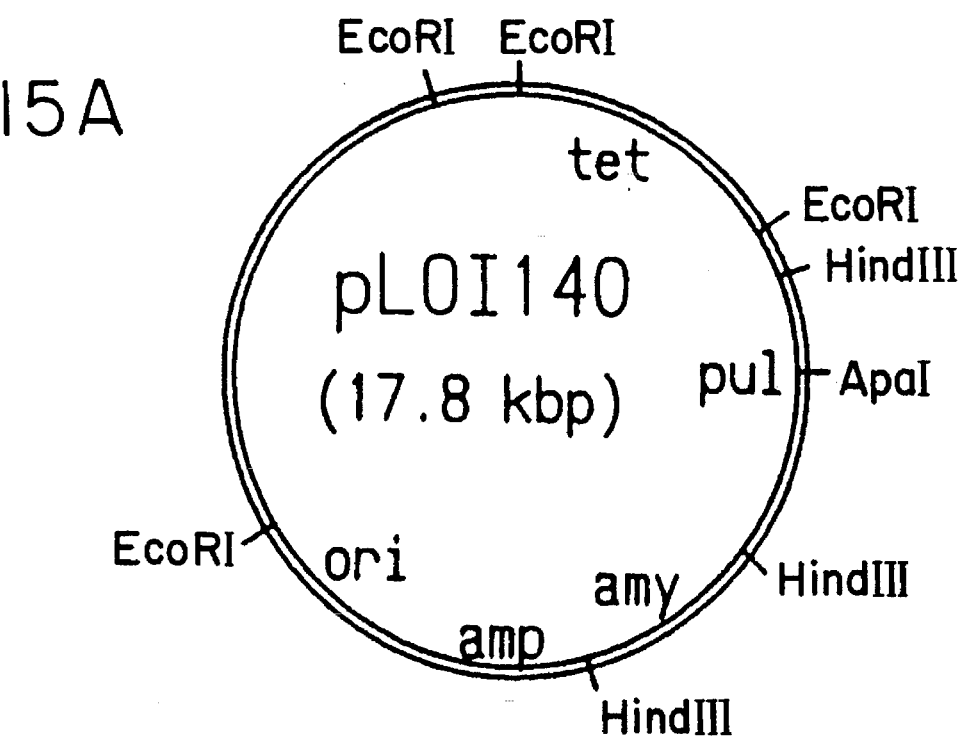
FIG. 15 illustrates the construction of plasmids pLOI140 and pLOI141, which comprise the α-amylase gene from *Bacillus stearothermophilus* and the pullulanase gene from *Thermoanaerobium brockii*.
Figure 15B:
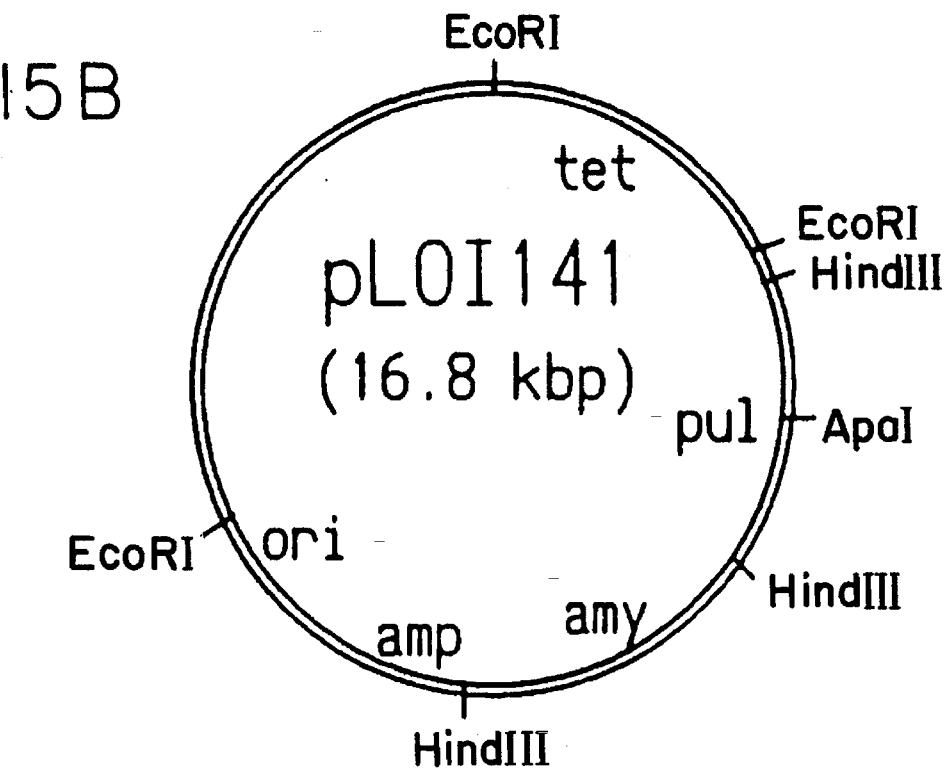

FIGS. 15A and B utilize the following abbreviations: amy, gene encoding *Bacillus stearothermophilus* α-amylase; pul, gene encoding *Thermoanaerobium brockii* pullulanase; tet, tetracycline resistance gene; amp, ampicillin resistance gene; ori, colE1 replicon.

Fermentation and analyses: Fermentations were carried out in 500-ml Fleakers which served as pH stats (350 ml working volume) essentially as described previously (Beall et al., supra). Media consisted of Luria broth containing 10% glucose, 5% glucose, 10% maltose, 5% maltose, or 4.5% starch (30° C., pH 6.0, 100 rpm). Fermentations were inoculated to an initial cell density of 0.03 mg dry weight/ml. Sugars were sterilized separately by filtration. Starch was not sterilized.

Cell mass was measured as O.D. 550 nm (approximately 0.32 g cell dry weight/liter at 1 O.D.). Total saccharifying activity was measured at 60° C. as the release of reducing sugars (Bergmeyer et al., supra). Ethanol was determined by gas liquid chromatography (Dombek et al., supra). Ethanol concentrations were expressed as g/liter. Ethanol yields were corrected for dilution by the addition of base during fermentations and were computed on the basis of total sugar or starch without correction for unused carbohydrate. Maximum theoretical yields from fermentation are approximately 0.51 g ethanol/g glucose, 0.53 g ethanol/g maltose, and 0.56 g ethanol/g starch. Results were based on an average of 2 or more fermentations.

Fermentation of starch: For starch fermentations, KO11(pLOI140) or KO11(pLOI141) cells were harvested from a prior 10% glucose fermentation after 72 hours and stored frozen. These cells were resuspended in 25 ml of Luria broth adjusted to pH 6.0. Starch (15.75 g) was suspended in 325 ml of Luria broth adjusted to pH 6.0. One-half of the cell suspension was added to the starch suspension, incubated in a boiling water bath with stirring until it reach 70° C., and held at 70° C. for 5 minutes. This mixture was cooled to 60° C. Remaining cells were added and incubation continued for 24 hours at 60° C. Heating inactivated recombinant *E. coli* and released thermostable enzymes for starch hydrolysis. The saccharified starch was cooled to 30° C. and adjusted to a volume of 350 ml with sterile distilled water.

An inoculum was grown overnight in 5% glucose, harvested by centrifugation, and used to start the fermentation (0.03 g cell dry weight of live cells/liter). Samples were removed for ethanol determination and for analysis by thin layer chromatography.

Glucose, maltose, maltotriose, and maltotetrose were separated by using unactivated, Whatman silica gel 150A plates (Whatman Inc., Clifton, N.J.). Samples of 1 μliter containing 5 to 50 μg saccharide were applied and separated at room temperature by a single development in acetone, ethyl acetate, and acetic acid (2:1:1, respectively) to which 2% water was added immediately prior to use. Dried plates were stained as described by Bounias [1980] Anal. Biochem. 106:291–295. Starch and sugars were obtained from the Sigma Chemical Company, St. Louis, Mo.

Fermentation of glucose and maltose by recombinant strains of *E. coli*: The fermentation of glucose and maltose by KO11 was examined. The results are graphically illustrated in FIGS. 16A and B, which reflect ethanol production and cell mass, respectively. The symbols used in the figures are as follows: ●, strain KO11 with 10% glucose; Δ, strain KO11(pLOI140) with 10% glucose; □, strain KO11(pLOI141) with 10% glucose; ○, strain KO11 with 5% maltose (results with 5% and 10% maltose were identical).

Although the utilization of maltose by *E. coli* has been well-studied in aerobic cultures, growth and ethanol production from maltose were much slower than glucose reaching less than 25% of the maximal theoretical yield (53.5 g ethanol/liter) from 10% maltose and 50% of the maximal theoretical yield (26.8 g ethanol/liter) from 5% maltose. Since similar results were observed with both concentrations of maltose, it is unlikely that slower growth and fermentation result from direct maltose toxicity. The slower fermentation of maltose as compared to glucose may result from other limitations such as saccharide transport, glucose phosphorylation, etc.

Figure 16A:
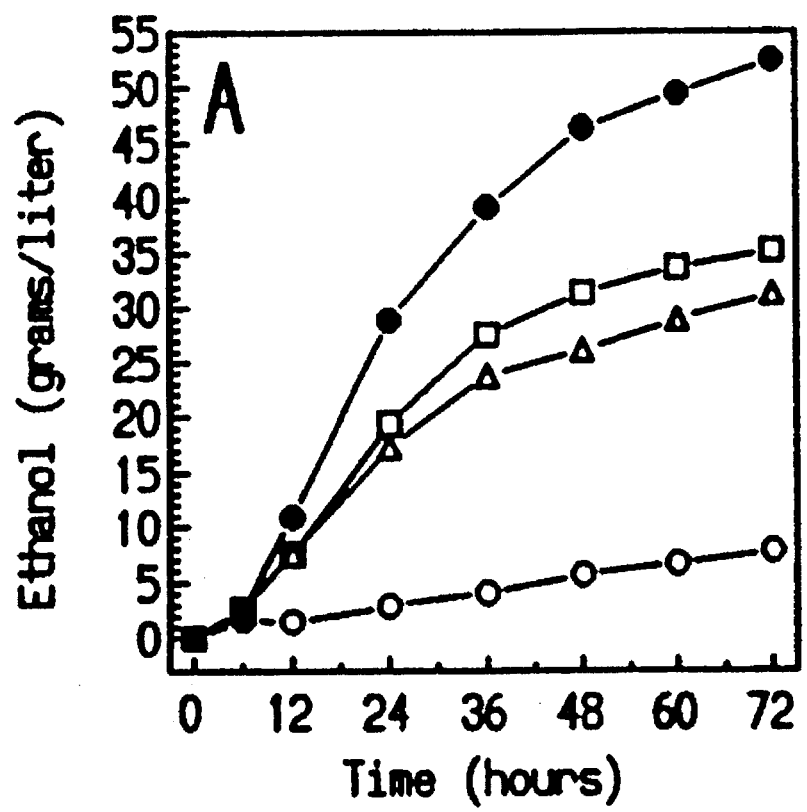
FIG. 16A and B illustrate ethanol production and cell mass, respectively, for the fermentation of glucose and maltose by KO11.
Figure 16B:
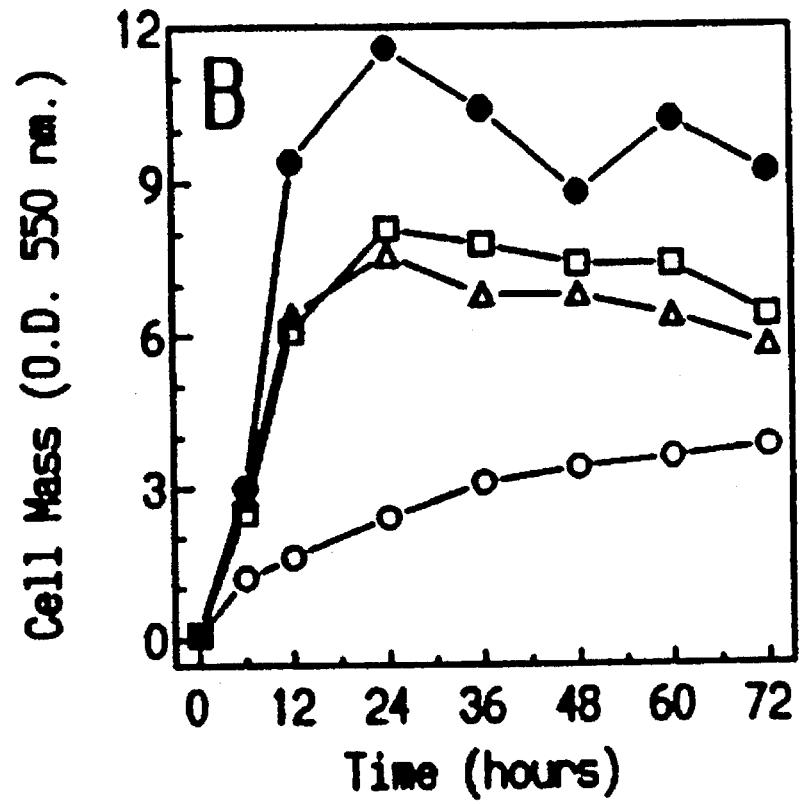

As seen in FIGS. 16A and B, the addition of plasmids pLOI140 and pLOI141 encoding α-amylase and pullulanase to strain *E. coli* KO11 decreased the rates of growth and ethanol production from glucose. Final cell yields and ethanol yields after 72 hours were reduced by approximately ⅓.

Expression of enzymes for saccharification: Total saccharifying activities produced by KO11(pLOI140) and KO11(pLOI141) were measured at the end of fermentation (72 hours) as the release of reducing sugars using a suspension of potato starch in Luria broth (pH 6.0) as the substrate (70° C.). Similar activity was observed with both strains, 30 μmoles reducing sugar/ml of culture per minute. Over 90% of this activity was intracellular but was readily released upon heating to 70° C.

Fermentation of starch: KO11(pLOI140) and KO11(pLOI141) were tested in a two-step process in which the enzymes for saccharification and ethanol production involved a single organism. Cells were harvested from a prior fermentation with 10% glucose, resuspended, and used as a source of enzymes to hydrolyze an equal volume of cold, 4.5% starch suspension (Luria broth, pH 6.0). Half of the harvested cells were added and the mixture rapidly heated to 70° C. in a water bath for approximately 5 minutes. This mixture was shifted to 60° C. and the balance of the cells added to facilitate hydrolysis. Corn, potato, rice, and wheat starch were tested and all behaved similarly. The starch suspension remained liquid throughout heating and hydrolysis in contrast to controls with KO11 lacking starch genes which solidified completely within 3 minutes of heating.

After incubation for 24 h at 60° C., the Luria broth containing hydrolyzed starch was cooled to 30° C. and inoculated to start fermentation (pH 6.0, 100 rpm, inoculum of 0.03 g cell dry wt/liter) as previously described (Beall et al., 1991, supra). Ethanol was produced at a similar rate from all types of starch, 0.26 to 0.28 g ethanol/liter during the initial 24 hours. Final ethanol yields were 0.35 to 0.37 g ethanol/gram of starch as compared to a theoretical maximum of 0.56 g ethanol/g starch. The results of the starch fermentation are provided in FIG. 17.

Figure 17:
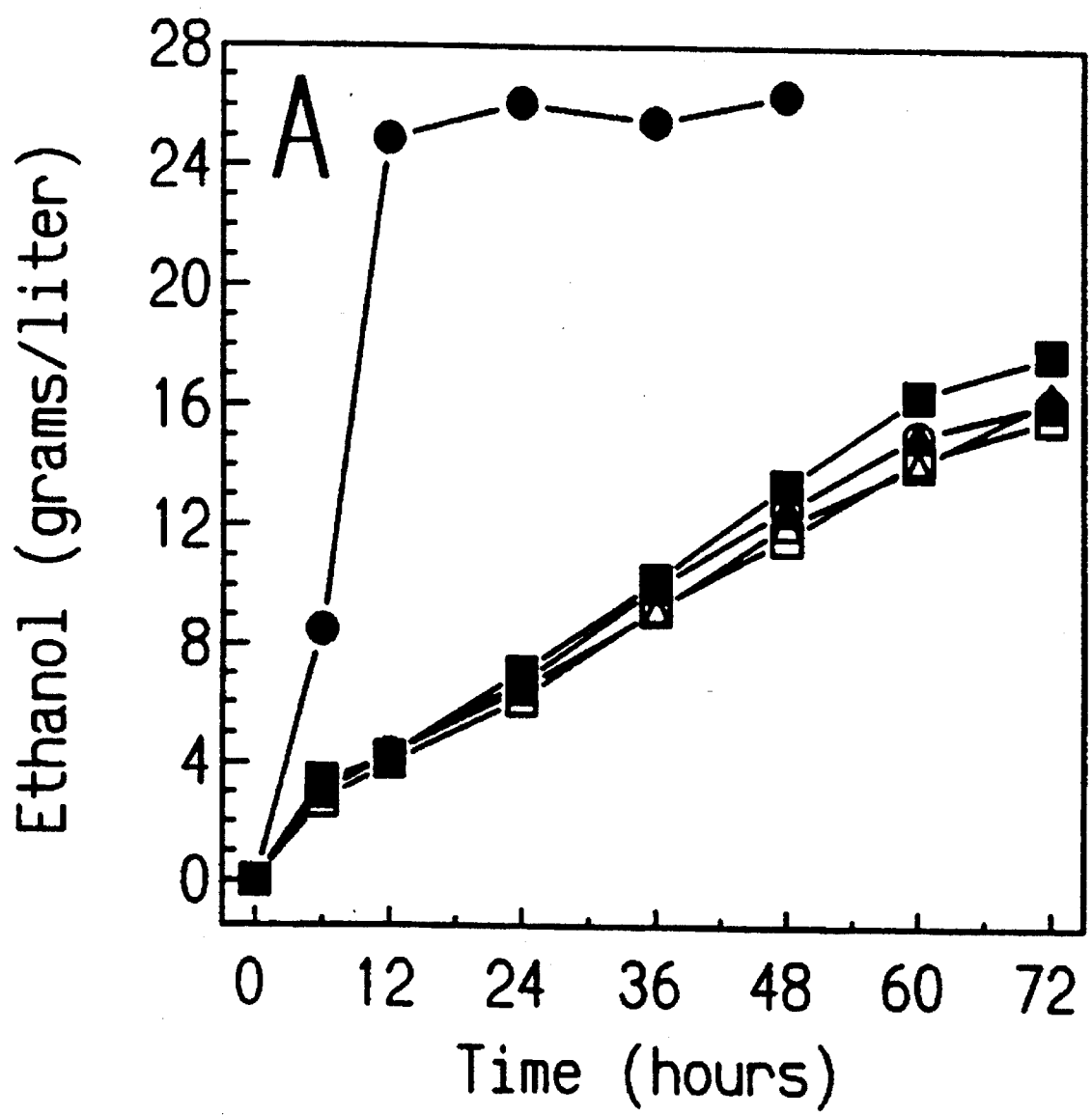
FIG. 17 illustrates the results of the starch fermentation by recombinant *E. coli* strains KO11(pLOI140) and KO11(pLOI141). (Since the results for both strains were essentially identical, only the data for KO11(pLOI141) is shown.)

Since the data for KO11(pLOI140) and KO11(pLOI141) were essentially identical, only the data for KO11(pLOI141) is shown in FIG. 17. The symbols used in FIG. 17 are as follows: Δ, corn starch (S-4126); □, potato starch (S-2004); ○, rice starch (S-7260); ▲, wheat starch (S-5127); ■, corn starch with 2 mM CaCl$_2$; ●, KO11 with 5% glucose as a control.

Figure 18:
FIG. 18 comprises the thin layer chromatographic analysis of corn starch fermentation by KO11(pLOI141) during fermentation (72 hours).

Samples were removed at different stages of this two-step process with corn starch and analyzed by thin layer chromatography (FIG. 18). After 24 hours, glucose, maltose, maltotriose, maltotetrose, and longer oligosaccharides are evident as hydrolysis products. Glucose, maltose, and maltotriose were utilized by KO11(pLOI141) during fermentation (72 hours).

FIG. 18 comprises the thin layer chromatographic analysis of corn starch fermentation. Maltose and glucose served as standards. Glucose through maltotetrose are labeled G1 through G4, respectively. The lanes were as follows: 1, glucose and maltose as standards; 2, broth after 24 hours saccharification at 60° C.; 3, broth shown in lane 2 after fermentation for 72 hours.

Starch-degrading enzymes are frequently stabilized by the presence of calcium ions. Fermentation experiments conducted with corn starch in Luria broth containing 2 mM calcium chloride resulted in slightly faster fermentation and a higher yield, 0.29 g ethanol/liter per hour and 0.40 g ethanol/g starch, respectively. As compared to conventional starch fermentations with yeasts and enzymes, the recombinant *E. coli* fermentation was slower and produced a lower final ethanol concentration. The overall ethanol yield from starch using this two-step process with a single organism was 85% that of current commercial processes using yeasts and supplemental enzymes (approximately 0.47 g ethanol/g starch).

Conclusions: While further improvements may be desirable, this example demonstrates that ethanologenic fermentations with recombinant *E. coli* could be used to produce part of the enzymes needed for starch saccharification. Enzyme production would be quite simple with no requirement for aeration. The thermostable bacterial enzymes funtion optimally at the same pH (approximately 6.0) as *E. coli*-based fermentation. With these organisms, residual starch in low value materials such as corn hulls could be used as a substrate and corn steep liquor as a source of complex nutrients. A process such as this may reduce the cost of enzymes for saccharification and increase ethanol yield from corn.

What is claimed is:

1. A method for producing ethanol from cellulose-containing biomass, comprising the steps of:
    A. contacting, in a first reaction vessel, said biomass with a polysaccharase such that cellulose in said biomass is broken down into simpler oligosaccharides and/or monosaccharides,
        wherein said contacting is carried out at a temperature of from about 40° C. to about 60° C. and a pH of from about 4.5 to about 5.0;
    B. producing from said first reaction vessel a sugar solution comprising said simpler oligosaccharides and/or monosaccharides;
    C. introducing said sugar solution into a fermentor which comprises gram-negative enteric recombinant host microorganisms capable of fermenting said simpler oligosaccharides and/or monosaccharides into ethanol; and
    D. fermenting said simpler oligosaccharides and/or monosaccharides into ethanol at a temperature of from about 30° C. to about 35° C. and a pH of about 6.0,
        wherein said microorganism is capable of fermenting monosaccharides into ethanol, and comprises a recombinant host, other than *Escherichia coli*, comprising a first heterologous DNA coding for alcohol dehydrogenase and pyruvate decarboxylase, wherein said heterologous DNA is from *Zymomonas mobilis* and wherein said host expresses said heterologous DNA at a sufficient functional level so as to facilitate the production of ethanol as the primary fermentation product by said host,
        wherein said host also produces a polysaccharase, and said host further comprises a second heterologous DNA segment, the expression product of which is said polysaccharase.

2. A method according to claim 1, wherein a first stream from said fermentor is withdrawn and used to cool the sugar solution produced in Step B.

3. A method according to claim 2, wherein said first stream is introduced into said first vessel after cooling said sugar solution produced in Step B.

4. A method according to claim 1, wherein the sugar solution produced in Step B is passed through an ultrafiltration unit having an upper molecular weight cut-off ultrafiltration membrane to obtain an ultrafiltration product solution and a second solution,
    said ultrafiltration product solution comprising predominantly molecules having a molecular weight below the molecular weight cut-off of said ultrafiltration membrane, said product solution comprising at least some of said oligosaccharides and/or monosaccharides obtained from Step B, and
    said second solution comprising predominantly molecules having a molecular weight above the molecular weight cut-off of said ultrafiltration membrane.

5. A method according to claim 4, wherein said product solution predominantly comprises molecules having a molecular weight of less than about 25,000.

6. A method according to claim 4, wherein the ultrafiltration product solution is subjected to reverse osmosis to obtain a first stream comprising predominantly water and a second stream comprising at least some of the oligosaccharides and/or monosaccharides.

7. A method according to claim 6, wherein said stream comprising predominantly water is recycled to the first reaction vessel.

8. A method according to claim 1, wherein the sugar solution produced in Step B is subjected to reverse osmosis to obtain a first stream comprising predominantly water and a second stream comprising at least some of the oligosaccharides and/or monosaccharides.

9. A method according to claim 8, wherein said stream comprising predominantly water is recycled to the first reaction vessel.

10. A method according to claim 1, wherein the contacting in said first reaction vessel is carried out at a temperature of from about 50° C. to about 60° C.

11. A method according to claim 1, wherein the contacting in said first reaction vessel is carried out at a temperature of from about 50° C. to about 55° C.

12. A method according to claim 1, wherein enzymes which break down cellulose into simpler oligosaccharides and/or monosaccharides are added to said fermentor.

13. The method of claim 1, wherein said host is selected from the group consisting of Erwinia, Klebsiella and Xanthomonas.

14. The method of claim 13, wherein said host is selected from the group consisting of Erwinia and Klebsiella.

15. The method of claim 14, wherein said host is *Klebsiella oxytoca* M5A1(pLOI555), ATCC 68564, deposited Mar. 14, 1991.

16. The method of claim 1, wherein said host has been transformed with a plasmid comprising genes coding for alcohol dehydrogenase and pyruvate decarboxylase, wherein said host expresses said genes to produce alcohol dehydrogenase and pyruvate decarboxylase at a sufficient functional level to facilitate the production of ethanol as the primary fermentation product by said host.

17. The method of claim 16, wherein said plasmid comprises *Zymomonas mobilis* genes coding for alcohol dehydrogenase and pyruvate decarboxylase.

18. The method of claim 16, wherein said plasmid further comprises a lac promoter which directs the expression of said genes coding for alcohol dehydrogenase and pyruvate decarboxylase.

19. The method of claim 16, wherein said plasmid has been designated pLOI555.

20. The method of claim 1, wherein said polysaccharase is a cellulolytic enzyme.

21. The method of claim 20, wherein said polysaccharase is selected from the group consisting of an endoglucanase, cellobiohydrolase, β-glucosidase, and β-glucanase.

22. The method of claim 21, wherein polysaccharase is an expression product of a celD gene.

23. The method of claim 22, wherein said celD gene is derived from *Clostridium thermocellum*.

24. The method of claim 21, wherein said polysaccharase is at least partially secreted by said host.

25. The method of claim 21, wherein said polysaccharase is accumulated in said host.

26. A method for producing ethanol from cellulose-containing biomass, comprising the steps of:
    A. contacting, in a first reaction vessel, said biomass with a polysaccharase such that oligosaccharide in said biomass is broken down into simpler oligosaccharides and/or monosaccharides,
        wherein said contacting is carried out at a temperature of from about 40° C. to about 60° C. and a pH of from about 4.5 to about 5.0;

B. producing from said first reaction vessel a sugar solution comprising said simpler oligosaccharides and/or monosacchrides;

C. introducing said sugar solution into a fermentor which comprises gram-negative enteric recombinant host microorganisms capable of fermenting said simpler oligosaccharides and/or monosaccharides into ethanol; and D. fermenting said simpler oligosaccharides and/or monosaccharides into ethanol at a temperature of from about 30° C. to about 35° C. and a pH of about 6.0, wherein said microorganism is capable of fermenting both monosaccharides and oligosaccharides into ethanol, and said microorganism further comprises a recombinant host comprising first heterologous DNA from *Zymomonas mobilis* coding for alcohol dehydrogenase and pyruvate decarboxylase, respectively, wherein said host
  (A) further comprises genes coding for proteins which enable said host to transport and metabolize an oligosaccharide, and
  (B) expresses said genes and said heterologous DNA at a level such that ethanol is produced as the primary fermentation product by said host from the metabolism of said oligosaccharide, and
wherein said recombinant host also produces a polysaccharase, and said host further comprises a second heterologous DNA segment, the expression product of which is said polysaccharase.

27. The method of claim 26, wherein said recombinant host is selected from the group consisting of Erwinia and Klebsiella.

28. The method of claim 27, wherein said recombinant host is *Klebsiella oxytoca* M5A1(pLOI555), ATCC 68564, deposited Mar. 14, 1991.

29. The method of claim 26, wherein said oligosaccharide is selected from the group consisting of dimers and trimers.

30. The method of claim 26, wherein said polysaccharase is a cellulolytic enzyme.

31. The method of claim 30, wherein said polysaccharase comprises the expression product of a cellulase gene of *Cellulomonas fimi*, and said host secretes at least some of said polysaccharase.

32. The method of claim 26, wherein said polysaccharase is selected from the group consisting of an endoglucanase, cellobiohydrolase, β-glucosidase, β-glucanase and hemicellulase, arabinosidase.

33. The method of claim 32, wherein said polysaccharase is an expression product of a celD gene.

34. The method of claim 33, wherein said celD gene is derived from *Clostridium thermocellum*.

35. The method of claim 26, wherein said host further comprises an additional heterologous DNA segment, the expression product of which is a protein involved in the transport of mono- and/or oligosaccharides into the recombinant host.

36. The method of claim 26, wherein said polysaccharase is at least partially secreted by said host.

37. The method of claim 26, wherein said polysaccharase is accumulated in said host.

38. The method of claim 37, wherein said host further comprises an additional heterologous DNA segment, the expression product of which is an additional polysaccharase that is at least partially secreted by said host.

39. The method of claim 38, wherein said additional polysaccharase comprises the expression product of a cellulase gene of *Cellulomonas fimi*.

* * * * *